United States Patent
Kolkman et al.

(10) Patent No.: US 12,146,173 B2
(45) Date of Patent: Nov. 19, 2024

(54) SERINE PROTEASES

(71) Applicant: DANISCO US INC, Palo Alto, CA (US)

(72) Inventors: Marc Kolkman, Palo Alto, CA (US); Anja Hemmingsen Kellett-Smith, Århus C (DK); Rie Mejldal, Østbirk (DK); Lilia Maria Babe, Emerald Hills, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 17/854,595

(22) Filed: Jun. 30, 2022

(65) Prior Publication Data

US 2022/0333092 A1 Oct. 20, 2022

Related U.S. Application Data

(63) Continuation of application No. 16/752,708, filed on Jan. 27, 2020, now abandoned, which is a continuation of application No. 15/520,844, filed as application No. PCT/US2015/057492 on Oct. 27, 2015, now abandoned.

(60) Provisional application No. 62/069,174, filed on Oct. 27, 2014.

(51) Int. Cl.
*C12N 9/54* (2006.01)
*C11D 3/386* (2006.01)

(52) U.S. Cl.
CPC ............... *C12N 9/54* (2013.01); *C11D 3/386* (2013.01); *C12Y 304/21062* (2013.01); *C11D 2111/12* (2024.01); *C11D 2111/14* (2024.01)

(58) Field of Classification Search
CPC .......................... C12Y 304/21062; C12N 9/54
See application file for complete search history.

(56) References Cited

U.S. PATENT DOCUMENTS

2002/0155575 A1* 10/2002 Norregaard-Madsen .................. C11D 3/38681
435/222

FOREIGN PATENT DOCUMENTS

| DE | 102007032111 A1 | 1/2009 |
| JP | 2003325186 | 11/2003 |
| WO | 2005/052146 A2 | 6/2005 |

OTHER PUBLICATIONS

Database UniProt [Online] Oct. 14, 2015 (Oct. 14, 2015), "SubName: Full=Peptidase SB {EC0:0000313:EMBL:KMJ55807.1};", XP002753867, Uniprot Database Accession No. A0A0J5GN15.
Database UniProt [Online] Mar. 23, 2010 (Mar. 23, 2010), "SubName: Full=Extracellular alkaline serine protease {EC0:0000313:EMBL:ADC50469.1};", XP002753868, retrieved from Uniprot Database Accession No. D3FW37.
Database UniProt [Online] Jan. 22, 2014 (Jan. 22, 2014), "SubName: Full=Peptidase S8 {EC0:0000313:EMBL:ERN55058.1};", XP002753869, retrieved from Uniprot Database Accession No. U6STV3.
Database NCBI [Online] Jun. 11, 2014 (Jun. 11, 2014), "peptidase S8 [Bacillus aurantiacus]", XP002753870, Database Accession No. WP 026690432.
Database UniProt [Online] Apr. 1, 1993 (Apr. 1, 1993), "RecName: Full=Subtilisin Savinase; EC=3.4.21.62; AltName: Full=Alkaline protease;", XP002753871, retrieved from Uniprot Accession No. P29600.
Database Geneseq [Online] Jun. 15, 2007 (Jun. 15, 2007), "Bacillus sp strain KSM-LDI alkaline protease.", XP002753872, retrieved from EBI accession No. GSP:ADF53282 Database accession No. ADF53282.
Surfactants: the ubiquitous amphiphiles, Royal Society of Chemistry available from http://www.rsc.org/chemistryworld/issues/2003/july/amphiphiles.asp (Year:2014).
GenBank Accession No. WP_075683870, peptidase S8 [Bacillus pseudofirmus] Jan. 12, 2017.
PCT International Search Report and the Written Opinion—PCT/US2015/057492—mailed Mar. 2, 2016.

* cited by examiner

Primary Examiner — Tekchand Saidha

(57) ABSTRACT

The present disclosure relates to serine proteases and variants thereof. Compositions containing the serine proteases are suitable for use in cleaning fabrics and hard surfaces, as well as in a variety of industrial applications.

8 Claims, 13 Drawing Sheets
Specification includes a Sequence Listing.

|  |  | 301 |  |
|---|---|---|---|
| BspAP02013 | (282) | ---------- | SEQ ID NO:24 |
| BspM02866 | (282) | ---------- | SEQ ID NO:25 |
| BspZ00056 | (282) | ---------- | SEQ ID NO:26 |
| B-spLL01_WP_047973355.1 | (282) | ---------- | SEQ ID NO:27 |
| B_pseudofirmus_YP_003427361 | (282) | ---------- | SEQ ID NO:28 |
| B_marmarensis_WP_022626565_ERN55058.1 | (282) | ---------- | SEQ ID NO:29 |
| A_transvaaiensis_WP_026475840.1 | (286) | ---------- | SEQ ID NO:30 |
| B_aurantiacus_WP_026690432.1 | (282) | ---------- | SEQ ID NO:31 |
| H_halophilus_WP_027965007.1 | (282) | ---------- | SEQ ID NO:32 |
| B_akibai_WP_035661169.1 | (282) | ---------- | SEQ ID NO:33 |
| B_sp_BAD02409.1 | (299) | GNGKGNGRN | SEQ ID NO:34 |
| H_halophilus_WP_027963976.1 | (276) | ---------- | SEQ ID NO:35 |
| B_amyloliquefaciens_CAA24990 | (276) | ---------- | SEQ ID NO:36 |
| G_stearothermophilus_ABY25856 | (276) | ---------- | SEQ ID NO:37 |
| B_subtilis_BAN09118 | (276) | ---------- | SEQ ID NO:38 |
| B_pumilus_ADK11996 | (276) | ---------- | SEQ ID NO:39 |
| B_licheniformis_CAJ70731 | (275) | ---------- | SEQ ID NO:40 |
| B_sonorensis_WP_006636716 | (275) | ---------- | SEQ ID NO:41 |
| B_lentus_P29600 | (270) | ---------- | SEQ ID NO:42 |
| Bacillus_sp_BAD11988 | (276) | ---------- | SEQ ID NO:43 |
| B_sp_sprD_AAC43581 | (277) | ---------- | SEQ ID NO:44 |
| Bacillus_sp_SprC_AAC43580 | (276) | ---------- | SEQ ID NO:45 |
| B_sp_Sendai_BAA06157 | (270) | ---------- | SEQ ID NO:46 |
| Consensus | (301) |  | SEQ ID NO:47 |

FIG. 7E

| Chain | | |
|---|---|---|
| 1:B_pseudof | AQNVPWGIPRVQGTDAQNAGYTGNGVKVAILDTGIDRSHPDLTANVQGHSVFTDSANRDPFFDGDGHGTHVAGTVAAVNNDIGVVGVASEADLYAVKVLNNAGSG | |
| 2:BspAP2013 | AQTTPWGIPRVQGTAAQNAGYTGNGVKVAILDTGIDRNHPDLSANVKGGHSVFTDSANSDPFFDGDGHGTHVAGTVAAVNNDIGVIGVASEASLYAVKVLNNAGSG | |
| 3:BspZ56 | GQTVPWGIPHVQGTAAQDAGYTGAGLKVAILDTGIDRNHEDLFANVKGGHSVFTDSANSDPFYDADGHGTHVAGTVAAVDNDLGVVGVASQAELYAVKVLNNSGSG | |
| 4:BspM2866 | GQTVPWGIPHVQGTAAQDAGFTGAGLKVAILDTGIEASHEDLSANVKGGHSVFTDSANSDPFYDPNGHGTHVAGTVAAVDNDLGVIGVAPEADLYAVKVLSNAGSG | |
| 5:2ST1.A | AQSVPYGVSQIKAPALHSQGYTGSNVKVAVIDSGIDSSHPDL---KVAGGASMVPSETN---PFQDNNSHGTHVAGTVAALNNSIGVLGVAPSASLYAVKVLGADGSG | |
| 6:1JEA | AQSVPWGISRVQAPAAHNRGLTGSGVKVAVLDTGIST--HPDL--NIRGGASFVPGEPS---T--QDGNGHGTHVAGTIAALNNSIGVLGVAPSAELYAVKVLGASGSG | |

FIG. 9A

```
Chain        110       115       120       125       130       135       140       145       150       155       160       165       170       175       180       185       190       195       200       205       210
             |         |         |         |         |         |         |         |         |         |         |         |         |         |         |         |         |         |         |         |         |
1:B_pseudof  SYAGIAEGIEWSINNGMDIINMSLGGSQSSAILKEFSDLAYAEGLLIVVAAAGNSGNRGGNNDTVGYPAKYESVIAVAATDQNNQRATFSSTGPAVEISAPGAGIL 110       115       120       125       130       135       140       145       150       155       160       165       170       175       180       185       190       195       200       205       210
             |         |         |         |         |         |         |         |         |         |         |         |         |         |         |         |         |         |         |         |         |
2:BspAP2013  SYAGIAEGIEWAINNDIDIINMSLGGSQSSAILKQFSDLAYAEGLLVVAAAGNSGTRSGRNDTVGYPAKYDSVIAVAATDQNNQRATFSSTGPAVEISAPGVGIL 110       115       120       125       130       135       140       145       150       155       160       165       170       175       180       185       190       195       200       205       210
             |         |         |         |         |         |         |         |         |         |         |         |         |         |         |         |         |         |         |         |         |
3:BspZ56     SYAGIAEGIEWSINNGMDIINMSLGGSQSSILKQFSDLAYAEGLLVVAAAGNRGGNNDTVGYPAKYDSVIAVAAVDQNNNRATFSSTGPAVEISAPGVSIL 110       115       120       125       130       135       140       145       150       155       160       165       170       175       180       185       190       195       200       205       210
             |         |         |         |         |         |         |         |         |         |         |         |         |         |         |         |         |         |         |         |         |
4:BspM2866   SIAGIAEGIEWSIDNGMDIINMSLGASQGSSILEQFSNLAYDEGLLVVAAAGNSGNRGGNNNTVGYPAAYDSVIAVAAVDQNNNRATFSSTGPAVEISAPGVNVL 105       110       115       120       125       130       135       140       145       150       155       160       165       170       175       180       185       190       195       200       205
             |         |         |         |         |         |         |         |         |         |         |         |         |         |         |         |         |         |         |         |         |
5:2ST1.A     QYSWIINGIEWAIANNMDVINMSLGGPSGSAALKAAVDKAVASGVVVVAAAGNEGT-SGSSSTVGYPGKYPSVIAVGAVDSSNQRASFSSVGPELDVMAPGVSIQ 105       110       115       120       125       130       135       140       145       150       155       160       165       170       175       180       185       190       195       200
             |         |         |         |         |         |         |         |         |         |         |         |         |         |         |         |         |         |         |         |
6:1JEA       SVSSIAQGLEWAGNNGMHVANLSLGSPSPSATLEQAVNSATSRGVLVVAASGNSGA------GSISYPARYANAMAVGATDQNNNRASFSQYGAGLDIVAPGVNVQ
```

*FIG. 9B*

| Chain | | | | | | | | | | | | | | |
|---|---|---|---|---|---|---|---|---|---|---|---|---|---|---|
| | 215 | 220 | 225 | 230 | 235 | 240 | 245 | 250 | 255 | 260 | 265 | 270 | 275 | 280 |
1:B_pseudof  STTPNNNYASFNGTSMASPHVAGVAAQVWQAKPHLSNVELRNLLNDTALPLGGSNQFGNGLVQSMAAIQQ  SEQ ID NO:48

| | 215 | 220 | 225 | 230 | 235 | 240 | 245 | 250 | 255 | 260 | 265 | 270 | 275 | 280 |
|---|---|---|---|---|---|---|---|---|---|---|---|---|---|---|
2:BspAP2013  STTPNNNYVSFNGTSMASPHVAGVAAQVWQAKPHLSNIELRNLLNDTAIDLGSSTQYGNGLVQSLEAIQQ  SEQ ID NO:49

| | 215 | 220 | 225 | 230 | 235 | 240 | 245 | 250 | 255 | 260 | 265 | 270 | 275 | 280 |
|---|---|---|---|---|---|---|---|---|---|---|---|---|---|---|
3:BspZ56  STTPGNNYAAFNGTSMASPHVAGVAAQVWQAKPELSNVELRNLLNETAVNLGGSNQFGHGLVQSLDAIQH  SEQ ID NO:50

| | 215 | 220 | 225 | 230 | 235 | 240 | 245 | 250 | 255 | 260 | 265 | 270 | 275 | 280 |
|---|---|---|---|---|---|---|---|---|---|---|---|---|---|---|
4:BspM2866  STTPGNNYASYNGTSMASPHVAGVAAQVWQANPGLSNTELRQLLNDTAVNLGPAHQYGHGLVQSLDAINQ  SEQ ID NO:51

| | 210 | 215 | 220 | 225 | 230 | 235 | 240 | 245 | 250 | 255 | 260 | 265 | 270 | 275 |
|---|---|---|---|---|---|---|---|---|---|---|---|---|---|---|
5:2ST1.A  STLPGNKYGAYNGTSMASPHVAGAAALILSKHPNWINTQVRSSLENTTTKLGDSFYYGKGLINVQAAAQ  SEQ ID NO:52

| | 205 | 210 | 215 | 220 | 225 | 230 | 235 | 240 | 245 | 250 | 255 | 260 | 265 | 268 |
|---|---|---|---|---|---|---|---|---|---|---|---|---|---|---|
6:1JEA  STYPGSTYASLNGTSMATPHVAGAAALVKQKNPSWSNVQIRNHLKNTATSLGSTNLYGSGLVNAEAATR  SEQ ID NO:53

FIG. 9C

SERINE PROTEASES

The present disclosure relates to serine proteases cloned from *Bacillus* spp., and variants thereof. Compositions containing the serine proteases are suitable for use in cleaning fabrics and hard surfaces, as well as in a variety of industrial applications.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

The present compositions and methods relate to recombinant serine proteases cloned from *Bacillus* spp., and variants thereof. Compositions containing the serine proteases are suitable for use in cleaning fabrics and hard surfaces, as well as in a variety of industrial applications.

In some embodiments, the invention is a BspAP02013-clade of subtilisins. In some embodiments, the invention is a recombinant polypeptide or active fragment thereof of a BspAP02013-clade subtilisin. In some embodiments, the BspAP02013-clade of subtilisins comprises a subtilisin or recombinant polypeptide or active fragment thereof comprising a DTGIXXXHXDLXXXXXGGXSVFTDSXXXXXXXDXXGH (SEQ ID NO:11) motif, wherein the initial D is the active site Aspartic acid, the terminal H is the active site Histidine, and X is any amino acid ("Motif 1"); and an amino acid sequence having at least 80% amino acid sequence identity to an amino acid sequence of SEQ ID NO:3, 6, or 9. In other embodiments, the BspAP02013-clade of subtilisins comprises a subtilisin or recombinant polypeptide or active fragment thereof comprising a DTGIXXXHXDLX$_a$XXXXGGXSVFTDSXXXXXXXDX XGH (SEQ ID NO:12) motif, wherein the initial D is the active site Aspartic acid, the terminal H is the active site Histidine, X is any amino acid, and X$_a$ is T, S or F or X$_a$ is S or F ("Motif 2"); and an amino acid sequence having at least 80% amino acid sequence identity to an amino acid sequence of SEQ ID NO:3, 6, or 9. In still further embodiments, the BspAP02013-clade of subtilisins comprises a subtilisin or recombinant polypeptide or active fragment thereof comprising a DTGIXXXHXDLXXXXXGGXSVFT DSXXX$_b$XXXXDXXGH (SEQ ID NO:13) motif, wherein the initial D is the active site Aspartic acid, the terminal H is the active site Histidine, X is any amino acid, and X$_b$ is S or R or X$_b$ is S ("Motif 3"); and an amino acid sequence having at least 80% amino acid sequence identity to an amino acid sequence of SEQ ID NO:3, 6, or 9. In yet another embodiment, the BspAP02013-clade of subtilisins comprises a subtilisin or recombinant polypeptide or active fragment thereof comprising a DTGIXXXHXDL X$_a$XXXXGGXSVFTDSXXX$_b$XXXXDXXGH (SEQ ID NO:14) motif, wherein the initial D is the active site Aspartic acid; the terminal H is the active site Histidine; X is any amino acid; X$_a$ is T, S or F or X$_a$ is S or F; and X$_b$ is S or R or X$_b$ is S ("Motif 4"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXANVXGG XSVFTD-SANXDPFXDX XGH (SEQ ID NO:15) motif, wherein the initial D is the active site Aspartic acid and the terminal H is the active site Histidine, and X is any amino acid ("Motif 5"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGI XXXHXDLX$_a$ANVXGGXSVFTDSANXDPFXDXXGH (SEQ ID NO:20) motif, wherein the initial D is the active site Aspartic acid; the terminal H is the active site Histidine; X is any amino acid; and X$_a$ is S or F ("Motif 6"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXANVXGGXSVFTDSA NX$_b$DPFXDXXGH (SEQ ID NO:21) motif, wherein the initial D is the active site Aspartic acid and the terminal H is the active site Histidine, X is any amino acid, and X$_b$ is S ("Motif 7"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGI XXXHXDLXXXXXGGXSVFXDXXXXXXXDXXGH (SEQ ID NO:22) motif, wherein the initial D is the active site Aspartic acid and the terminal H is the active site Histidine, and X is any amino acid ("Motif 8"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXXNVXGGXSVFXDXXNXDPXXDX XGH (SEQ ID NO:23) motif, wherein the initial D is the active site Aspartic acid and the terminal H is the active site Histidine, and X is any amino acid ("Motif 9"); and an amino acid sequence having at least 80% amino acid sequence identity to an amino acid sequence of SEQ ID NO:3, 6, or 9.

In some embodiments, the recombinant polypeptide or active fragment thereof comprises an amino acid sequence having at least 70%, at least 75%, at least 80%, at least 85%, at least 90%, at least 95%, at least 99% amino acid sequence identity to an amino acid sequence of SEQ ID NO:3, 6 or 9. In some embodiments, the recombinant polypeptide has protease activity, or subtilisin activity, specifically casein hydrolysis activity. In some embodiments, the recombinant polypeptide retains at least 50% of its maximal protease activity at a pH range of 8 to 12. In some embodiments, the recombinant polypeptide retains at least 50% of its maximal protease activity at a temperature range of 55° C. to 75° C. In some embodiments, the recombinant polypeptide has cleaning activity in a detergent composition, including, for example, an automatic dish washing detergent and a laundry detergent.

In some embodiments, the invention is a composition comprising a surfactant and the recombinant polypeptide or active fragment thereof described herein. In some embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the composition is a detergent composition, such as a laundry detergent, a fabric softening detergent, a dishwashing detergent, and a hard-surface cleaning detergent. In some embodiments, the composition further comprises at least one calcium ion and/or zinc ion, at least one stabilizer, at least one bleaching agent, phosphate, or borate. In some embodiments the composition is phosphate-free and/or borate-free. In some embodiments, the composition is a granular, powder, solid, bar, liquid, tablet, gel, paste or unit dose composition. In some embodiments, the composition further comprising one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

Some embodiments are directed to a method of cleaning, comprising contacting a surface or an item with a recombinant polypeptide or active fragment thereof or a composition described herein. Other embodiments are directed to a method for producing the recombinant polypeptide or active fragment thereof comprising stably transforming a host cell with an expression vector comprising a polynucleotide encoding the recombinant polypeptide or active fragment thereof described herein.

BRIEF DESCRIPTION OF THE DRAWINGS

Figure 7B:
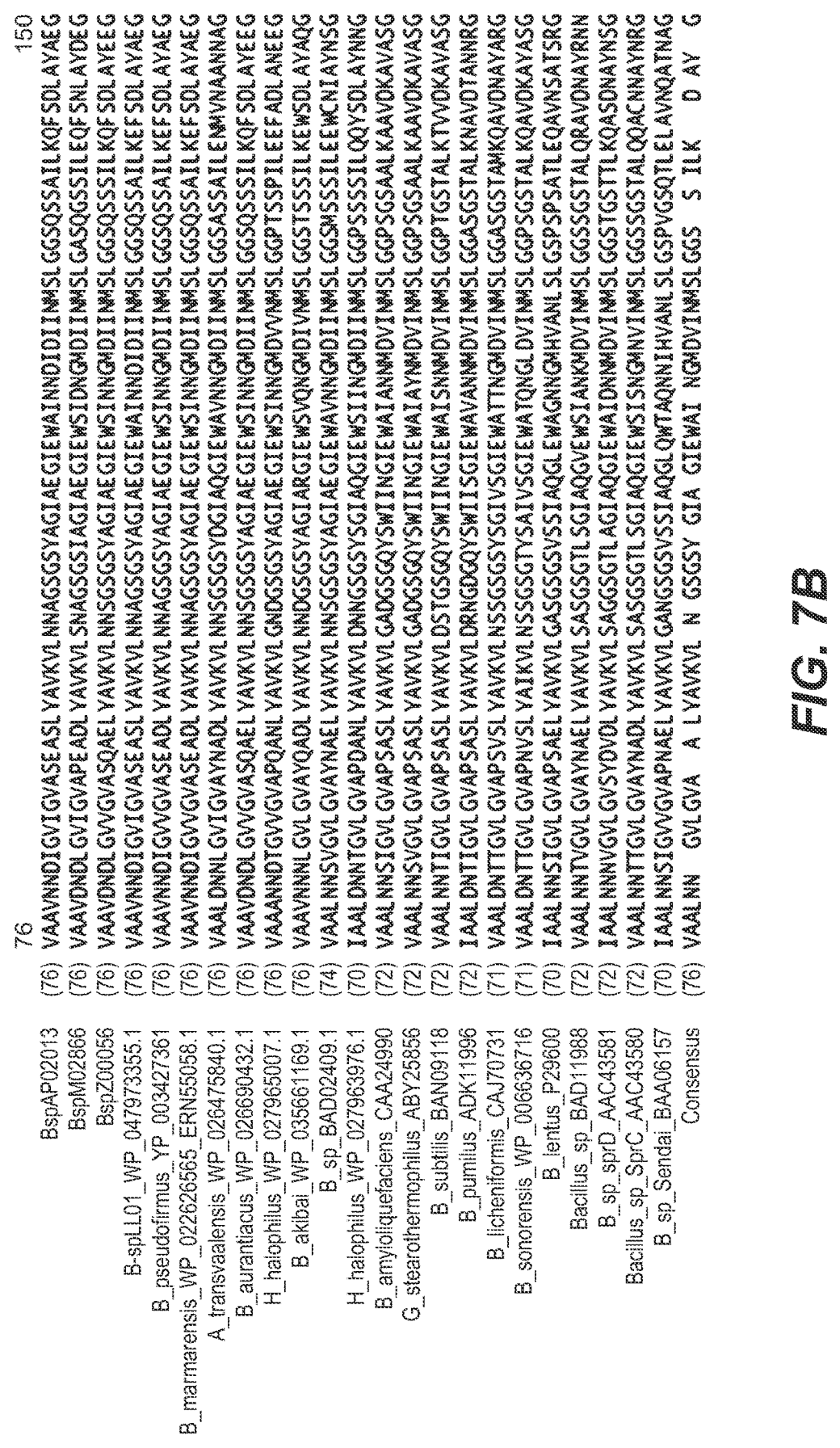
Figure 7C:
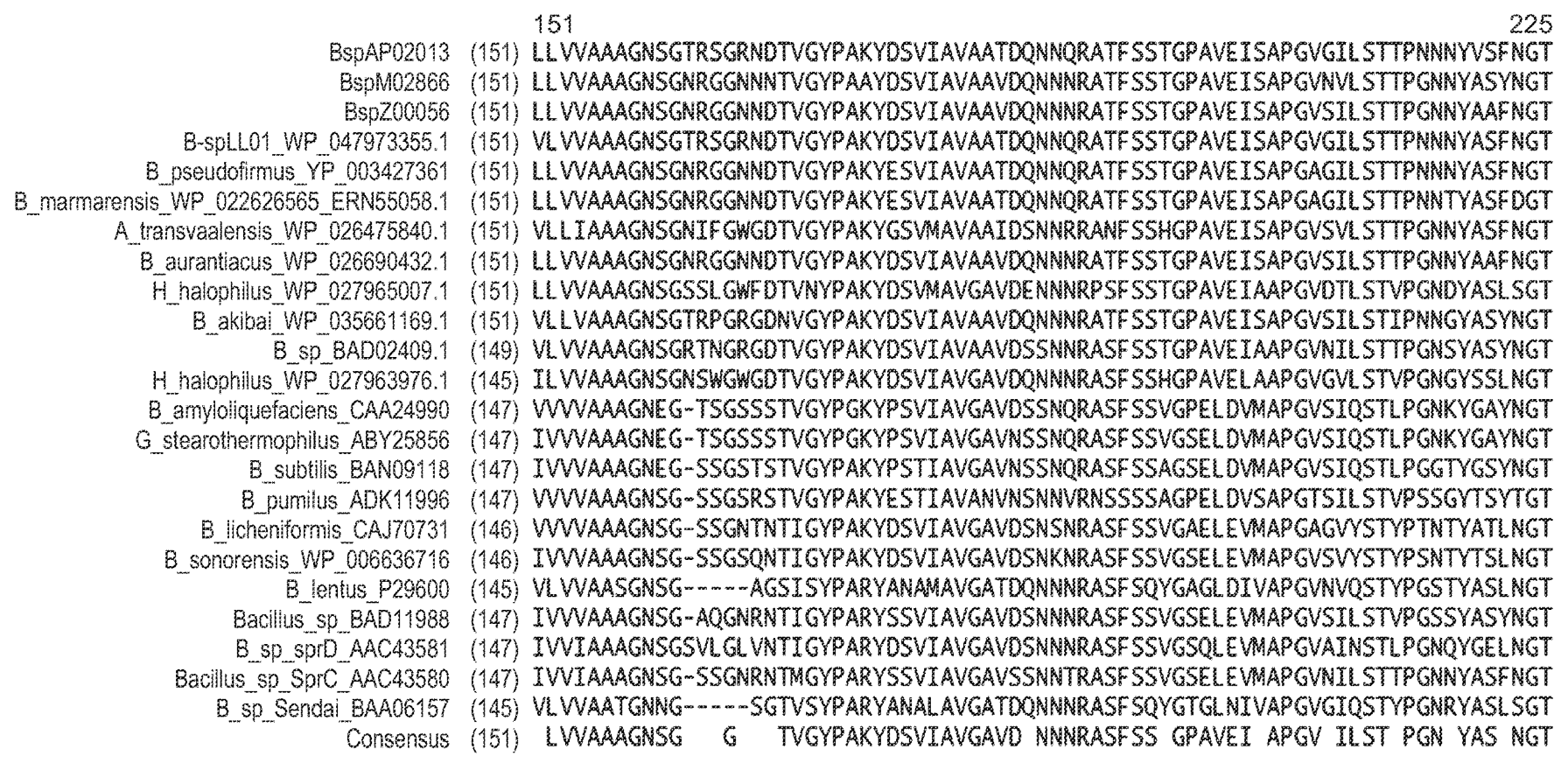

FIGS. 7A-7E provide CLUSTAL W (1.83) multiple sequence alignment of subtilisins including BspAP02013, BspM02866, and BspZ00056.

FIGS. 9A to 9C illustrate structural alignment of BspAP02013-clade subtilisins (1-4) with subtilisin BPN' from *B. amyloliquefaciens* (5) and the subtilisin from *B. lentus* (6), where the common motif is shown by a box.

Figure 1:
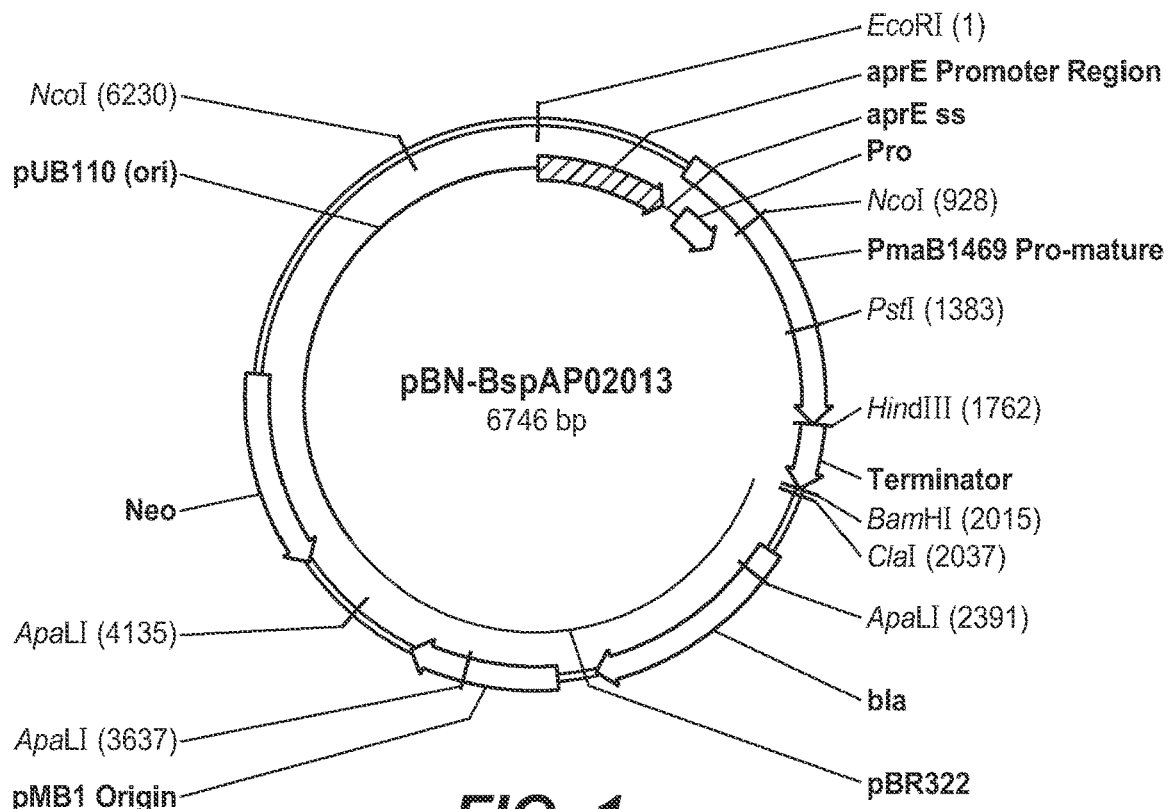
FIG. 1 provides a plasmid map for expression of BspAP02013 protease.

Described are compositions and methods relating to recombinant serine proteases from *Bacillus* species. The compositions and methods are based, in part, on the observation that recombinant BspAP02013, BspM02866, and BspZ00056, among others, have protease activity in the presence of a surfactant, in basic reaction conditions, and at elevated temperatures. These features of BspAP02013, BspM02866, and BspZ00056 make these proteases well suited for use in cleaning fabrics and hard surfaces, as well as in textile, leather and feather processing. The new proteases are also well suited to inclusion in compositions for protein degradation, including but not limited to laundry and dishwashing detergents.

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus Bacillus" includes all species within the genus "Bacillus," as known to those of skill in the art, including but not limited to B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii, and B. thuringiensis. It is recognized that the genus Bacillus continues to undergo taxonomical reorganization. Thus, it is intended that the genus include species that have been reclassified, including but not limited to such organisms as B. stearothermophilus, which is now named "Geobacillus stearothermophilus", or B. polymyxa, which is now "Paenibacillus polymyxa" The production of resistant endospores under stressful environmental conditions is considered the defining feature of the genus Bacillus, although this characteristic also applies to the recently named Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus, and Virgibacillus.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms described below and known in the art.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cut-off=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The present disclosure provides novel serine protease enzymes. The serine protease polypeptides of the present disclosure include isolated, recombinant, substantially pure, or non-naturally occurring polypeptides. In some embodiments, the polypeptides are useful in cleaning applications and can be incorporated into cleaning compositions that are useful in methods of cleaning an item or a surface in need thereof.

The BspAP02013-clade of subtilisins are characterized by two separate 2 amino acid residue insertions; Insertion 1 is after conserved positions HPDL at positions 39-42 and Insertion 2 is after position N56, wherein the amino acid positions are numbered by correspondence with the amino acid sequence of subtilisin BPN', wherein both insertions occur in the span of residues linking the catalytic aspartic acid (D32) and catalytic histidine (H68) that form part of the characteristic catalytic triad.

In some embodiments, the invention is a BspAP02013-clade of subtilisins. In some embodiments, the invention is a recombinant polypeptide or active fragment thereof of the BspAP02013-clade. In some embodiments, the BspAP02013-clade of subtilisins comprises a subtilisin or recombinant polypeptide or active fragment thereof comprising a DTGIXXXHXDLXXXXXGGXSVFTDSXXXXXXXDXXGH (SEQ ID NO:11) motif, wherein the initial D is the active site Aspartic acid, the terminal H is the active site Histidine, and X is any amino acid ("Motif 1"); and an amino acid sequence having at least 80% amino acid sequence identity to an amino acid sequence of SEQ ID NO:3, 6, or 9. In other embodiments, the BspAP02013-clade of subtilisins comprises a subtilisin or recombinant polypeptide or active fragment thereof comprising a DTGIXXXHXDLX$_a$XXXXGGXSVFTDSXXXXXXXDXXGH (SEQ ID NO:12) motif, wherein the initial D is the active site Aspartic acid, the terminal H is the active site Histidine, X is any amino acid, and X$_a$ is T, S or F or X$_a$ is S or F ("Motif 2"); and an amino acid sequence having at least 80% amino acid sequence identity to an amino acid sequence of SEQ ID NO:3, 6, or 9. In still further embodiments, the BspAP02013-clade of subtilisins comprises a subtilisin or recombinant polypeptide or active fragment thereof comprising a DTGIXXXHXDLXXXXXGGXSVFTDSXXX$_b$XXXXDXXGH (SEQ ID NO:13) motif, wherein the initial D is the active site Aspartic acid, the terminal H is the active site Histidine, X is any amino acid, and X$_b$ is S or R or X$_b$ is S ("Motif 3"); and an amino acid sequence having at least 80% amino acid sequence identity to an amino acid sequence of SEQ ID NO:3, 6, or 9. In yet other embodiments, the BspAP02013-clade of subtilisins comprises a subtilisin or recombinant polypeptide or active fragment thereof comprising a DTGIXXXHXDLX$_a$XXXXGGXSVFTDSXXX$_b$XXXXDXXGH (SEQ ID NO:14), wherein the initial D is the active site Aspartic acid; the terminal H is the active site Histidine; X is any amino acid; X$_a$ is T, S or F or X$_a$ is S or F; and X$_b$ is S or R or X$_b$ is S ("Motif 4"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXANVXGGXSVFTDSANXDPFXDXXGH (SEQ ID NO:15) motif, wherein the initial D is the active site Aspartic acid and the terminal H is the active site Histidine, and X is any amino acid ("Motif 5"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLX$_a$ANVXG GXSVFTD-SANXDPFXDXXGH (SEQ ID NO:20) motif, wherein the initial D is the active site Aspartic acid; the terminal H is the active site Histidine; X is any amino acid; and X$_a$ is S or F ("Motif 6"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXANVXGGXSVFTD-SANX$_b$DPFXDXXGH (SEQ ID NO:21) motif, wherein the initial D is the active site Aspartic acid and the terminal H is the active site Histidine, X is any amino acid, and X$_b$ is S ("Motif 7"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGIXXXHXDLXXXXXGGXSVFXDXXXXXXXXDXXGH (SEQ ID NO:22) motif, wherein the initial D is the active site Aspartic acid and the terminal H is the active site Histidine, and X is any amino acid ("Motif 8"); and an amino acid sequence having at least 80% amino acid sequence identity to an amino acid sequence of SEQ ID NO:3, 6, or 9. In some embodiments, the BspAP02013-clade of subtilisins comprises a subtilisin or recombinant polypeptide or active fragment thereof comprising a DTGI XXXHXDLXXNVXGG GSVFXDXXNXDPXXDXXGH (SEQ ID NO:23) motif, wherein the initial D is the active site Aspartic acid and the terminal H is the active site Histidine, and X is any amino acid ("Motif 9"); and an amino acid sequence having at least 80% amino acid sequence identity to an amino acid sequence of SEQ ID NO:3, 6, or 9.

In some embodiments, a subtilisin of the BspAP02013-clade of subtilisins and/or the recombinant polypeptide or active fragment thereof of the BspAP02013-clade comprises an HX DLXANVXGGXS (SEQ ID NO:16) motif ("Sub-motif 1"), wherein the initial D is the active site Aspartic acid, the terminal GGXS is in the outermost strand of the central beta sheet, and X is any amino acid; and an amino acid sequence having at least 80% amino acid sequence identity to an amino acid sequence of SEQ ID NO:3, 6, or 9. Sub-motif 1 includes Insertion 1. In some embodiments, a subtilisin of the BspAP02013-clade of subtilisins and/or the recombinant polypeptide or active fragment thereof of the BspAP02013-clade comprises an GGXSVFTDSA NXDPFXD (SEQ ID NO:17) motif ("Sub-motif 2"), wherein the initial GGXS is in the outermost strand of the central beta sheet and X is any amino acid; and an amino acid sequence having at least 80% amino acid sequence identity to an amino acid sequence of SEQ ID NO:3, 6, or 9. Sub-motif 2 includes Insertion 2. In some embodiments, a subtilisin of the BspAP02013-clade of subtilisins and/or the recombinant polypeptide or active fragment thereof of the BspAP02013-clade comprises an HXDLX$_a$ANVXGGXS (SEQ ID NO:18) motif ("Sub-motif 3"), wherein the initial D is the active site Aspartic acid; the terminal GGXS is in the outermost strand of the central beta sheet; X$_a$ is T, S or F or X$_a$ is S or F; and X is any amino acid. Sub-motif 3 includes Insertion 1; and an amino acid sequence having at least 80% amino acid sequence identity to an amino acid sequence of SEQ ID NO:3, 6, or 9. In some embodiments, a subtilisin of the BspAP02013-clade of subtilisins and/or the recombinant polypeptide or active fragment thereof of the BspAP02013-clade comprises an GGXSVFTDSANX$_b$DPFXD (SEQ ID NO:19) motif ("Sub-motif 4"), wherein the initial GGXS is in the outermost strand of the central beta sheet, X is any amino acid, and X$_b$ is S or R or X$_b$ is S; and an amino acid sequence having at least 80% amino acid sequence identity to an amino acid sequence of SEQ ID NO:3, 6, or 9. Sub-motif 4 includes Insertion 2.

In some embodiments, a subtilisin of the BspAP02013-clade of subtilisins and/or recombinant polypeptide or active fragment thereof of the BspAP02013-clade comprises a DTGI XXXHXDLXXXXXGGXSVFTDSXXXXXXXDXXGH (SEQ ID NO:11) motif, wherein the initial D is the active site Aspartic acid, the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, or WP_022626565. In other embodiments, a subtilisin of the BspAP02013-clade of subtilisins and/or recombinant polypeptide or active fragment thereof of the BspAP02013-clade comprises a DTGIXXXHXDLXXXXXGGXSVFTDSXXXXXXXDXXGH (SEQ ID NO:11) motif, wherein the initial D is the active site Aspartic acid, the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_047973355.

In yet another embodiment, a subtilisin of the BspAP02013-clade of subtilisins and/or the recombinant polypeptide or active fragment thereof of the BspAP02013-clade comprises a DTGIXXXHXDLX$_a$XXXXGGXSVFTDSXXXXXXXDXXGH (SEQ ID NO:12) motif, wherein the initial D is the active site Aspartic acid, the terminal H is the active site Histidine, X is any amino acid, and X$_a$ is T, S or F; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, or WP_022626565. In yet another embodiment, a subtilisin of the BspAP02013-clade of subtilisins and/or the recombinant polypeptide or active fragment thereof of the BspAP02013-clade comprises a DTGIXXXHXDLX$_a$XXXXGGXSVFTDSXXXXXXXDXXGH (SEQ ID NO:12) motif, wherein the initial D is the active site Aspartic acid, the terminal H is the active site Histidine, X is any amino acid, and X$_a$ is T, S or F; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_047973355. In yet a further embodiment, a subtilisin of the BspAP02013-clade of subtilisins and/or the recombinant polypeptide or active fragment thereof of the BspAP02013-clade comprises a DTGIXXXHXDLX$_a$XXXXGGXSVFT DSXXXXXXXD XXGH (SEQ ID NO:12) motif, wherein the initial D is the active site Aspartic acid, the terminal H is the active site Histidine, X is any amino acid, and X$_a$ is S or F; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_047973355.

In still further embodiments, a subtilisin of the BspAP02013-clade of subtilisins and/or the recombinant polypeptide or active fragment thereof of the BspAP02013-clade comprises a DTGIXXXHXDLXXXXXGGXSVFTDSXXX$_b$XXXXDX XGH (SEQ ID NO:13) motif, wherein the initial D is the active site Aspartic acid, the terminal H is the active site Histidine, X is any amino acid, and X$_b$ is S or R; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragments thereof of the BspAP02013-clade does not comprise WP_012957833, ERN55058, or WP_022626565. In yet another embodiment, a subtilisin of the BspAP02013-clade of subtilisins and/or the recombinant polypeptide or active fragment thereof of the BspAP02013-clade comprises a DTGIXXXHXDLXXXXXGGXSVFTDSXXX$_b$XXXXD XXGH (SEQ ID NO:13) motif, wherein the initial D is the active site Aspartic acid, the terminal H is the active site Histidine, X is any amino acid, and X$_b$ is S or R; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_047973355. In yet still further embodiments, a subtilisin of the BspAP02013-clade of subtilisins and/or the recombinant polypeptide or active fragment thereof of the BspAP02013-clade comprises a DTGIXXXHXDL XXXXXGGXSVFTDSXXX$_b$XXXXDXXGH (SEQ ID NO:13) motif, wherein the initial D is the active site Aspartic acid, the terminal H is the active site Histidine, X is any amino acid, and X$_b$ is S; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_047973355.

In further embodiments, a subtilisin of the BspAP02013-clade of subtilisins and/or the recombinant polypeptide or active fragment thereof of the BspAP02013-clade comprises a DTGIXXXHXDLX$_a$XXXXGGXSVFTDSXXX$_b$XXXXD XXGH (SEQ ID NO:14), wherein the initial D is the active site Aspartic acid; the terminal H is the active site Histidine; X is any amino acid; X$_a$ is T, S or F or X$_a$ is S or F; and X$_b$ is S or R or X$_b$ is S; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, or WP_022626565. In still further embodiments, a subtilisin of the BspAP02013-clade of subtilisins and/or the recombinant polypeptide or active fragment thereof of the BspAP02013-clade comprises a DTGIXXXHXDLX$_a$XXXXGGXSVFTDSXXX$_b$XXXXD XXGH (SEQ ID NO:14), wherein the initial D is the active site Aspartic acid; the terminal H is the active site Histidine; X is any amino acid; X$_a$ is T, S or F or X$_a$ is S or F; and X$_b$ is S or R or X$_b$ is S; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_047973355. In still further embodiments, a subtilisin of the BspAP02013-clade of subtilisins and/or the recombinant polypeptide or active fragment thereof of the BspAP02013-clade comprises a DTGIXXXHXDLX$_a$XXXXGGXSVFTDSXXX$_b$XXXXD XXGH (SEQ ID NO:14), wherein the initial D is the active site Aspartic acid; the terminal H is the active site Histidine; X is any amino acid; X$_a$ is S or F; and X$_b$ is S; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_047973355.

In some embodiments, a subtilisin of the BspAP02013-clade of subtilisins and/or the recombinant polypeptide or active fragment thereof of the BspAP02013-clade comprises a DTGI XXXHXDLXANVXGGXSVFTD-SANXDPFXDXXGH (SEQ ID NO:15) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, or WP_022626565. In some embodiments, a subtilisin of the BspAP02013-clade of subtilisins and/or the recombinant polypeptide or active fragment thereof of the BspAP02013-clade comprises a DTGIXXXHXDL XANVXGGXSVFTD-SANXDPFXDXXGH (SEQ ID NO:15) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, WP_047973355, ERN55058 or WP_022626565.

In some embodiments, a subtilisin of the BspAP02013-clade of subtilisins and/or the recombinant polypeptide or active fragment thereof of the BspAP02013-clade comprises a DTGI XXXHXDLX$_a$ANVXGGXSVFTD-SANXDPFXDXXGH (SEQ ID NO:20) motif, wherein the initial D is the active site Aspartic acid; the terminal H is the active site Histidine; X is any amino acid; and X$_a$ is S or F; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_047973355. In some embodiments, a subtilisin of the BspAP02013-clade of subtilisins and/or the recombinant polypeptide or active fragment thereof of the BspAP02013-clade comprises a DTGIXXXHXDL XANVXGGXSVFTDSANX$_b$DPFXDXXGH (SEQ ID NO:21) motif, wherein the initial D is the active site Aspartic acid and the terminal H is the active site Histidine, X is any amino acid, and X$_b$ is S; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_047973355.

In some embodiments, the BspAP02013-clade of subtilisins comprises a subtilisin or recombinant polypeptide or active fragment thereof comprising a DTGIXXXHXDLXXXXXXGG XSVFXDXXXXXXXXDXXGH (SEQ ID NO:22) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_026690432. In other embodiments, the BspAP02013-clade of subtilisins comprises a subtilisin or recombinant polypeptide or active fragment thereof comprising a DTGIXXXHXDLXXXXXXGGXSVFXDX XXXXXXXDXXGH (SEQ ID NO:22) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, WP_026690432, or WP_047973355.

In some embodiments, the BspAP02013-clade of subtilisins comprises a subtilisin or recombinant polypeptide or active fragment thereof comprising a DTGIXXXHXDLXXNVXGG XSVFXDXXNXDPXXDXXGH (SEQ ID NO:23) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, or WP_026690432. In some embodiments, the BspAP02013-clade of subtilisins comprises a subtilisin or recombinant polypeptide or active fragment thereof comprising a DTGIXXXHXDLXXNVXGGXSVFXDXX NXDPXXDXXGH (SEQ ID NO:23) motif, wherein the initial D is the active site Aspartic acid and the terminal H is the active site Histidine, and X is any amino acid; and an amino acid sequence having at least 80% amino acid sequence identity to an amino acid sequence of SEQ ID NO:3, 6, or 9, with the proviso that the subtilisin of the BspAP02013-clade of subtilisins and/or recombinant polypeptide or active fragment thereof of the BspAP02013-clade does not comprise WP_012957833, ERN55058, WP_022626565, WP_026690432, or WP_047973355.

In some embodiments, the polypeptide or active fragment thereof of the present invention is a polypeptide having a specified degree of amino acid sequence homology to the exemplified polypeptides, e.g., 70%, 80%, 85%, 90%, 95%, 96%, 97%, 98%, 99% or 100% sequence identity to the amino acid sequence selected from the group consisting of SEQ ID NOs: 3, 6, and 9. Some embodiments are directed to a recombinant polypeptide or active fragment thereof comprising an amino acid sequence having at least 70% amino acid sequence identity to an amino acid sequence of SEQ ID NO:3, 6, or 9. Other embodiments are directed to a recombinant polypeptide or active fragment thereof comprising an amino acid sequence having at least 70% amino acid sequence identity to an amino acid sequence of SEQ ID NO:3, 6, or 9, with the proviso that the recombinant polypeptide or active fragment thereof does not comprise WP_012957833, ERN55058, WP_022626565, WP_026690432, BAD02409, WP_027963976, WP_027965007, WP_026475840, or JP2003325186-0001. Still other embodiments are directed to a recombinant polypeptide or active fragment thereof comprising an amino acid sequence having at least 70% amino acid sequence identity to an amino acid sequence of SEQ ID NO:3, 6, or 9, with the proviso that the recombinant polypeptide or active fragment thereof does not comprise WP_047973355, WP_035661169, WP_012957833, ERN55058, WP_022626565, WP_026690432, BAD02409, WP_027963976, WP_027965007, WP_026475840, or JP2003325186-0001. Further embodiments are directed to a recombinant polypeptide or active fragment thereof comprising an amino acid sequence having at least 75% amino acid sequence identity to an amino acid sequence of SEQ ID NO:3, 6, or 9. Other embodiments are directed to a recombinant polypeptide or active fragment thereof comprising an amino acid sequence having at least 75% amino acid sequence identity to an amino acid sequence of SEQ ID NO:3, 6, or 9, with the proviso that the recombinant polypeptide or active fragment thereof does not comprise WP_026690432, WP_012957833, ERN55058, WP_022626565, BAD02409, or JP2003325186-0001. Still other embodiments are directed to a recombinant polypeptide or active fragment thereof comprising an amino acid sequence having at least 75% amino acid sequence identity to an amino acid sequence of SEQ ID NO:3, 6, or 9, with the proviso that the recombinant polypeptide or active fragment thereof does not comprise WP_026690432, WP_012957833, ERN55058, WP_022626565, BAD02409, JP2003325186-0001, WP_047973355, or WP_035661169. Even further embodiments are directed to a recombinant polypeptide or active fragment thereof comprising an amino acid sequence having at least 80% amino acid sequence identity to an amino acid sequence of SEQ ID NO:3, 6, or 9. Other embodiments are directed to a recombinant polypeptide or active fragment thereof comprising an amino acid sequence having at least 80% amino acid sequence identity to an amino acid sequence of SEQ ID NO:3, 6, or 9, with the proviso that the recombinant polypeptide or active fragment thereof does not comprise WP_012957833, ERN55058, WP_022626565, or WP_026690432. Still other embodiments are directed to a recombinant polypeptide or active fragment thereof comprising an amino acid sequence having at least 80% amino acid sequence identity to an amino acid sequence of SEQ ID NO:3, 6, or 9, with the proviso that the recombinant polypeptide or active fragment thereof does not comprise WP_012957833, ERN55058, WP_022626565, WP_026690432, or WP_047973355. Some embodiments are directed to a recombinant polypeptide or active fragment thereof comprising an amino acid sequence having at least 85% amino acid sequence identity to an amino acid sequence of SEQ ID NO:3, 6, or 9. Other embodiments are directed to a recombinant polypeptide or active fragment thereof comprising an amino acid sequence having at least 85% amino acid sequence identity to an amino acid sequence of SEQ ID NO:3, 6, or 9, with the proviso that the recombinant polypeptide or active fragment thereof does not comprise WP_012957833, ERN55058, WP_022626565, or WP_026690432. Other embodiments are directed to a recombinant polypeptide or active fragment thereof comprising an amino acid sequence having at least 85% amino acid sequence identity to an amino acid sequence of SEQ ID NO:3, 6, or 9, with the proviso that the recombinant polypeptide or active fragment thereof does not comprise WP_012957833, ERN55058, WP_022626565, WP_026690432, or WP_047973355. Other embodiments are directed to a recombinant polypeptide or active fragment thereof comprising an amino acid sequence having at least 85% amino acid sequence identity to an amino acid sequence of SEQ ID NO:6 or 9, with the proviso that the recombinant polypeptide or active fragment thereof does not comprise WP_026690432. Some embodiments are directed to a recombinant polypeptide or active fragment thereof comprising an amino acid sequence having at least 90% amino acid sequence identity to an amino acid sequence of SEQ ID NO:3, 6, or 9. Other embodiments are directed to a recombinant polypeptide or active fragment thereof comprising an amino acid sequence having at least 90% amino acid sequence identity to an amino acid sequence of SEQ ID NO:3, 6, or 9, with the proviso that the recombinant polypeptide or active fragment thereof does not comprise WP_012957833, ERN55058, or WP_022626565. Other embodiments are directed to a recombinant polypeptide or active fragment thereof comprising an amino acid sequence having at least 90% amino acid sequence identity to an amino acid sequence of SEQ ID NO:3, 6, or 9, with the proviso that the recombinant polypeptide or active fragment thereof does not comprise WP_012957833, ERN55058, WP_022626565, or WP_047973355. Other embodiments are directed to a recombinant polypeptide or active fragment thereof comprising an amino acid sequence having at least 90% amino acid sequence identity to an amino acid sequence of SEQ ID NO:6 or 9. Some embodiments are directed to a recombinant polypeptide or active fragment thereof comprising an amino acid sequence having at least 95% amino acid sequence identity to an amino acid sequence of SEQ ID NO:3, 6, or 9. Other embodiments are directed to a recombinant polypeptide or active fragment thereof comprising an amino acid sequence having at least 95% amino acid sequence identity to an amino acid sequence of SEQ ID NO:3, 6, or 9, with the proviso that the recombinant polypeptide or active fragment thereof does not comprise WP_047973355. Still other embodiments are directed to a recombinant polypeptide or active fragment thereof comprising an amino acid sequence having at least 97% amino acid sequence identity to an amino acid sequence of SEQ ID NO:3, 6, or 9. Homology can be determined by amino acid sequence alignment, e.g., using a program such as BLAST, ALIGN, or CLUSTAL, as described herein. In some embodiments, the polypeptide or active fragment thereof is an isolated, recombinant, substantially pure, or non-naturally occurring enzyme having protease activity, such as subtilisin activity, or casein hydrolysis activity (for example, dimethylcasein hydrolysis activity). In some embodiments, the polypeptide or active fragment thereof has protease activity in the presence of a surfactant.

Also provided is a polypeptide enzyme of the present invention, having protease activity, such as alkaline protease activity, said enzyme comprising an amino acid sequence which differs from the amino acid sequence of SEQ ID NO:3, 6 or 9 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant serine protease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples.

The polypeptide or active fragment thereof of the present invention can have protease activity over a broad range of pH conditions. In some embodiments, the polypeptide or active fragment thereof of the present invention have protease activity on dimethylcasein as a substrate, as demonstrated in Examples below. In some embodiments, the polypeptide or active fragment thereof of the present invention have protease activity at a pH of from about 4.0 to about 12.0. In some embodiments, the polypeptide or active fragment thereof of the present invention have protease activity at a pH of from about 6.0 to about 12.0. In some embodiments, the polypeptide or active fragment thereof of the present invention have at least 50%, 60%, 70%, 80% or 90% of maximal protease activity at a pH of from about 6.0 to about 12.0, or from about 7.0 to about 12.0. In some embodiments, the polypeptide or active fragment thereof of the present invention have protease activity at a pH above 6.0, 6.5, 7.0, 7.5, 8.0, 8.5, 9.0, 9.5, 10.0, 10.5, 11.0 or 11.5. In some embodiments, the polypeptide or active fragment thereof of the present invention have protease activity at a pH below 12.0, 11.5, 11.0, 10.5, 10.0, 9.5, 9.0, 8.5, 8.0, 7.5, 7.0, or 6.5.

In some embodiments, the polypeptide or active fragment thereof of the present invention of the present invention have protease activity at a temperature range from about 10° C. to about 90° C., or from about 30° C. to about 80° C. In some embodiments, the polypeptide or active fragment thereof of the present invention of the present invention have protease activity at a temperature range of from about 55° C. to about 75° C. In some embodiments, the polypeptide or active fragment thereof of the present invention have at least 50%, 60%, 70%, 80% or 90% of maximal protease activity at a temperature of from about 55° C. to about 75° C. In some embodiments, the serine proteases have activity at a temperature above 50° C., 55° C., 60° C., 65° C., or 70° C. In some embodiments, the serine proteases have activity at a temperature below 75° C., 80° C., 70° C., 65° C., 60° C., or 55° C.

In some embodiments, the polypeptide or active fragment thereof of the present invention has at least 50% activity after 20 minutes at 40° C. under stressed conditions. In some embodiments, the polypeptide or active fragment thereof of the present invention has at least 30% activity after 20 minutes at 50° C. under stressed conditions. In some embodiments, the polypeptide or active fragment thereof of the present invention has at least 50% activity after 20 minutes at 40° C. under stressed conditions. In some embodiments, the polypeptide or active fragment thereof of the present invention has at least 30% activity after 20 minutes at 60° C. under stressed conditions. The stressed conditions can be, for example, those shown in Examples. In some embodiments, the stressed condition is in an LAS/EDTA assay, Tris/EDTA assay, or OMO HDL assay.

In some embodiments, the serine protease polypeptides of the present invention demonstrate cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the serine protease polypeptides of the present invention demonstrate cleaning performance in automatic dishwashing (ADW) detergent compositions. In some embodiments, the cleaning performance in automatic dishwashing (ADW) detergent compositions includes cleaning of egg yolk stains. In some embodiments, the serine protease polypeptides of the present invention demonstrate cleaning performance in laundry detergent compositions. In some embodiments, the cleaning performance in laundry detergent compositions includes cleaning of blood/milk/ink stains. In each of the cleaning compositions, the serine protease polypeptides of the present invention demonstrate cleaning performance with or without a bleach component.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include serine protease polypeptides having enzymatic activity (e.g., proteolytic activity) which are useful in cleaning applications and cleaning compositions for cleaning an item or a surface (e.g., surface of an item) in need of cleaning.

In some embodiments, a polynucleotide of the present invention is a polynucleotide having a specified degree of nucleic acid homology to the exemplified polynucleotide. In some embodiments, a polynucleotide of the present invention has a nucleic acid sequence having at least 50, 60, 65, 70, 75, 80, 85, 90, 91, 92, 93, 94, 95, 96, 97, 98, 99 or 100% identity to SEQ ID NO: 3, 6 or 9. In some embodiments, the polynucleotide comprises a nucleic acid sequence selected from the group consisting of SEQ ID NOs:1, 4, and 7. In other embodiments, the polynucleotide of the present invention may also have a complementary nucleic acid sequence to a nucleic acid sequence selected from the group consisting of SEQ ID NOs:1, 4, and 7. Homology can be determined by amino acid sequence alignment, e.g., using a program such as BLAST, ALIGN, or CLUSTAL, as described herein.

In some embodiments, the invention provides an isolated, recombinant, substantially pure, synthetically derived, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, synthetically derived or non-naturally-occurring nucleic acid comprising a nucleotide sequence encoding a combination of two or more of any polypeptides of the invention described above and elsewhere herein. The present invention provides nucleic acids encoding a serine protease polypeptide of the present invention, wherein the serine protease polypeptide is a mature form having proteolytic activity. In some embodiments, the serine protease is expressed recombinantly with a homologous pro-peptide sequence. In other embodiments, the serine protease is expressed recombinantly with a heterologous pro-peptide sequence (e.g., GG36 pro-peptide sequence).

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a serine protease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides of the invention that encode serine protease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

The present invention provides vectors comprising at least one serine protease polynucleotide of the invention described herein (e.g., a polynucleotide encoding a serine protease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector, although other methods are available and known in the art. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one serine protease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a serine protease polypeptide of the invention is operably linked to one or additional nucleic acid segments required for efficient gene expression (e.g., a promoter operably linked to the polynucleotide of the invention which encodes a serine protease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting

[eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments of the present invention, a polynucleotide sequence encoding the serine protease polypeptide (as well as other sequences included in the vector) is integrated into the genome of the host cell, while in other embodiments, a plasmid vector comprising a polynucleotide sequence encoding the serine protease polypeptide remains as autonomous extra-chromosomal element within the cell. The invention provides both extrachromosomal nucleic acid elements as well as incoming nucleotide sequences that are integrated into the host cell genome. The vectors described herein are useful for production of the serine protease polypeptides of the invention. In some embodiments, a polynucleotide construct encoding the serine protease polypeptide is present on an integrating vector that enables the integration and optionally the amplification of the polynucleotide encoding the serine protease polypeptide into the host chromosome. Examples of sites for integration are well known to those skilled in the art. In some embodiments, transcription of a polynucleotide encoding a serine protease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda PR or PL promoters, and the *E. coli* lac, trp or tac promoters.

Serine protease polypeptides of the present invention can be produced in host cells of any suitable microorganism, including bacteria and fungi. In some embodiments, serine protease polypeptides of the present invention can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the serine protease polypeptides are produced by *Bacillus* sp. host cells. Examples of *Bacillus* sp. host cells that find use in the production of the serine protease polypeptides of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells are used for production of serine protease polypeptides. U.S. Pat. Nos. 5,264,366 and 4,760,025 (RE 34,606) describe various *Bacillus* host strains that can be used for producing serine protease polypeptide of the invention, although other suitable strains can be used.

Several bacterial strains that can be used to produce serine protease polypeptides of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *B. subtilis* host strain. Numerous *B. subtilis* strains are known, including, but not limited to, for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a serine protease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., US2005/0202535, incorporated herein by reference).

Host cells are transformed with at least one nucleic acid encoding at least one serine protease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E.*

*coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a serine protease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one serine protease polypeptide or at least one nucleic acid of the invention.

In some embodiments, host cells transformed with at least one polynucleotide sequence encoding at least one serine protease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

Assays for detecting and measuring the enzymatic activity of an enzyme, such as a serine protease polypeptide of the invention, are well known. Various assays for detecting and measuring activity of proteases (e.g., serine protease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.)., Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature serine protease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (MA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature serine protease polypeptide of the invention. A mature serine protease polypeptide does not include a signal peptide or a propeptide sequence. Some methods comprise making or producing a serine protease polypeptide of the invention in a recombinant bacterial host cell, such as for example, a *Bacillus* sp. cell (e.g., a *B. subtilis* cell). In some embodiments, the invention provides a method of producing a serine protease polypeptide of the invention, the method comprising cultivating a recombinant host cell comprising a recombinant expression vector comprising a nucleic acid encoding a serine protease polypeptide of the invention under conditions conducive to the production of the serine protease polypeptide. Some such methods further comprise recovering the serine protease polypeptide from the culture.

In some embodiments the invention provides methods of producing a serine protease polypeptide of the invention, the methods comprising: (a) introducing a recombinant expression vector comprising a nucleic acid encoding a serine protease polypeptide of the invention into a population of cells (e.g., bacterial cells, such as B. subtilis cells); and (b) culturing the cells in a culture medium under conditions conducive to produce the serine protease polypeptide encoded by the expression vector. Some such methods further comprise: (c) isolating the serine protease polypeptide from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101, all of which are incorporated herein by reference. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

The serine protease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5 to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the serine protease polypeptides provided herein, alone or in combination with other proteases and/or additional enzymes. The required level of enzyme is achieved by the addition of one or more serine protease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the serine protease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when the serine protease polypeptide (s) is/are employed in a granular composition or liquid, it is desirable for the serine protease polypeptide to be in the form of an encapsulated particle to protect the serine protease polypeptide from other components of the granular composition during storage. In addition, encapsulation is also a means of controlling the availability of the serine protease polypeptide during the cleaning process. In some embodiments, encapsulation enhances the performance of the serine protease polypeptide (s) and/or additional enzymes. In this regard, the serine protease polypeptides of the present invention are encapsulated with any suitable encapsulating material known in the art. In some embodiments, the encapsulating material typically encapsulates at least part of the serine protease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden); and PM6545, PM6550, PM7220, PM7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

TABLE I

Water Hardness

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Accordingly, in some embodiments, the present invention provides serine protease polypeptides that show surprising wash performance in at least one set of wash conditions (e.g., water temperature, water hardness, and/or detergent concentration). In some embodiments, the serine protease polypeptides of the present invention are comparable in wash performance to other serine protease polypeptide proteases. In some embodiments of the present invention, the serine protease polypeptides provided herein exhibit enhanced oxidative stability, enhanced thermal stability, enhanced cleaning capabilities under various conditions, and/or enhanced chelator stability. In addition, the serine protease polypeptides of the present invention find use in cleaning compositions that do not include detergents, again either alone or in combination with builders and stabilizers.

In some embodiments of the present invention, the cleaning compositions comprise at least one serine protease polypeptide of the present invention at a level from about 0.00001 to about 10% by weight of the composition and the balance (e.g., about 99.999 to about 90.0%) comprising cleaning adjunct materials by weight of composition. In some other embodiments of the present invention, the cleaning compositions of the present invention comprises at least one serine protease polypeptide at a level of about 0.0001 to about 10%, about 0.001 to about 5%, about 0.001 to about 2%, about 0.005 to about 0.5% by weight of the composition and the balance of the cleaning composition (e.g., about 99.9999 to about 90.0%, about 99.999 to about 98%, about 99.995 to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the serine protease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147, and subtilisin 168). Additional examples include those mutant proteases described in U.S. Pat. Nos. RE 34,606; 5,955,340; 5,700,676; 6,312,936; and 6,482,628, all of which are incorporated herein by reference. Additional protease examples include, but are not limited to, trypsin (e.g., of porcine or bovine origin), and the *Fusarium* protease described in WO89/06270. In some embodiments, commercially available protease enzymes that find use in the present invention include, but are not limited to MAX-ATASE®, MAXACAL™, MAXAPEM™, OPTICLEAN®, OPTIMASE®, PROPERASE®, PURAFECT®, PURAFECT® OXP, PURAIVIAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO 92/21760, WO09/149200, WO09/149144, WO09/149145, WO11/072099, WO10/056640, WO 10/056653, WO11/140364, WO12/151534, US 2008/0090747; U.S. Pat. Nos. 5,801,039; 5,340,735; 5,500,364; 5,855,625; RE 34,606; 5,955,340; 5,700,676; 6,312,936; 6,482,628; 8,530,219; and various other patents. In some further embodiments, neutral metalloproteases find use in the present invention, including but not limited to the neutral metalloproteases described in WO1999014341, WO 1999033960, WO1999014342, WO1999034003, WO2007044993, WO2009058303, WO 2009058661, WO2014/071410, WO2014/194032, WO2014/194034, WO2014/194054, and WO2014/194117. Exemplary metalloproteases include nprE, the recombinant form of neutral metalloprotease expressed in *B. subtilis* (See e.g., WO07/044993), and PMN, the purified neutral metalloprotease from *B. amyloliquefaciens.*

In addition, any suitable lipase finds use in the present invention. Suitable lipases include, but are not limited to those of bacterial or fungal origin. Chemically or genetically modified mutants are encompassed by the present invention. Examples of useful lipases include *H. lanuginosa* lipase (See e.g., EP258068, and EP305216), *Rhizomucor miehei* lipase (See e.g., EP238023), *Candida* lipase, such as *C. antarctica* lipase (e.g., the *C. antarctica* lipase A or B; See e.g., EP214761), *Pseudomonas* lipases such as *P. alcaligenes* lipase and *P. pseudoalcaligenes* lipase (See e.g., EP218 272), *P. cepacia* lipase (See e.g., EP331376), *P. stutzeri* lipase (See e.g., GB1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO88/09367), and the cutinase derived from *Fusarium solani pisi* (See, WO90/09446).

Additional suitable lipases include lipases such as M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001 to about 10% of additional lipase by weight of the composition and the balance of cleaning adjunct materials by weight of composition. In some other embodiments of the present invention, the cleaning compositions of the present invention also comprise lipases at a level of about 0.0001 to about 10%, about 0.001 to about 5%, about 0.001 to about 2%, about 0.005 to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. hcheniformis* (See e.g., GB 1,296, 839). Additional suitable amylases include those found in WO9510603, WO9526397, WO9623874, WO9623873, WO9741213, WO 9919467, WO0060060, WO0029560, WO9923211, WO9946399, WO0060058, WO0060059, WO9942567, WO0114532, WO02092797, WO0166712, WO0188107, WO0196537, WO 0210355, WO9402597, WO0231124, WO9943793, WO9943794, WO2004113551, WO 2005001064, WO2005003311, WO0164852, WO2006063594, WO2006066594, WO 2006066596, WO2006012899, WO2008092919, WO2008000825, WO2005018336, WO 2005066338, WO2009140504, WO2005019443, WO2010091221, WO2010088447, WO 0134784, WO2006012902, WO2006031554, WO2006136161, WO2008101894, WO 2010059413, WO2011098531, WO2011080352, WO2011080353, WO2011080354, WO 2011082425, WO2011082429, WO2011076123, WO2011087836, WO2011076897, WO 94183314, WO9535382, WO9909183, WO9826078, WO9902702, WO9743424, WO9929876, WO9100353, WO9605295, WO9630481, WO9710342, WO2008088493, WO2009149419, WO 2009061381, WO2009100102, WO2010104675, WO2010117511, and WO2010115021. Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001 to about 10% of additional amylase by weight of the composition and the balance of cleaning adjunct materials by weight of composition. In some other embodiments of the present invention, the cleaning compositions of the present invention also comprise amylases at a level of about 0.0001 to about 10%, about 0.001 to about 5%, about 0.001 to about 2%, about 0.005 to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *H. insolens* cellulases (See e.g., U.S. Pat. No. 4,435,307). Especially suitable cellulases are the cellulases having color care benefits (See e.g., EP0495257). Commercially available cellulases that find use in the present include, but are not limited to CELLUZYME®, CAREZYME® (Novozymes), REVITALENZ™ 100 (Danisco US Inc) and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449,318, and 7,833,773. In some embodiments, the cleaning compositions of the present invention further comprise cellulases at a level from about 0.00001 to about 10% of additional cellulase by weight of the composition and the balance of cleaning adjunct materials by weight of composition. In some other embodiments of the present invention, the cleaning compositions of the present invention also comprise cellulases at a level of about 0.0001 to about 10%, about 0.001 to about 5%, about 0.001 to about 2%, about 0.005 to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114; 6,602,842; and 6,440,991, all of which are incorporated herein by reference). Commercially available mannanases that find use in the present invention include, but are not limited to MANNASTAR®, PURABRITE™, and MANNAWAY®. In some embodiments, the cleaning compositions of the present invention further comprise mannanases at a level from about 0.00001 to about 10% of additional mannanase by weight of the composition and the balance of cleaning adjunct materials by weight of composition. In some embodiments of the present invention, the cleaning compositions of the present invention also comprise mannanases at a level of about 0.0001 to about 10%, about 0.001 to about 5%, about 0.001 to about 2%, about 0.005 to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001 to about 10% of additional peroxidase and/or oxidase by weight of the composition and the balance of cleaning adjunct materials by weight of composition. In some other embodiments of the present invention, the cleaning compositions of the present invention also comprise peroxidase and/or oxidase enzymes at a level of about 0.0001 to about 10%, about 0.001 to about 5%, about 0.001 to about 2%, about 0.005 to about 0.5% peroxidase and/or oxidase enzymes by weight of the composition.

In some embodiments, additional enzymes find use, including but not limited to perhydrolases (See e.g., WO2005056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the serine protease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more serine protease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the serine protease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the serine protease polypeptides of the present invention. Thus, in some embodiments, the compositions comprising at least one serine protease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one serine protease polypeptide of the present invention are fabric cleaning compositions such as those described in U.S. Pat. Nos. 6,610,642 and 6,376,450. In addition, the serine protease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one serine protease polypeptide provided herein. Thus, in some embodiments, the compositions comprising at least one serine protease polypeptide of the present invention is a hard surface cleaning composition such as those described in U.S. Pat. Nos. 6,610,642; 6,376,450; and 6,376,450.

In yet further embodiments, the present invention provides dishwashing compositions comprising at least one serine protease polypeptide provided herein. Thus, in some embodiments, the compositions comprising at least one serine protease polypeptide of the present invention is a hard surface cleaning composition such as those in U.S. Pat. Nos. 6,610,642 and 6,376,450. In some still further embodiments, the present invention provides dishwashing compositions comprising at least one serine protease polypeptide provided herein. In some further embodiments, the compositions comprising at least one serine protease polypeptide of the present invention comprise oral care compositions such as those in U.S. Pat. Nos. 6,376,450 and 6,376,450. The formulations and descriptions of the compounds and cleaning adjunct materials contained in the aforementioned U.S. Pat. Nos. 6,376,450; 6,605,458; 6,605,458; and 6,610,642 find use with the serine protease polypeptides provided herein.

The cleaning compositions of the present invention are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303, all of which are incorporated herein by reference. When a low pH cleaning composition is desired, the pH of such composition is adjusted via the addition of a material such as monoethanolamine or an acidic material such as HCl.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N (CH2COOM)$_2$ where R is $C_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1 to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1 to about 15% or even from about 3.0 to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP2100949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001 to about 10%, from about 0.01 to about 5%, or even from about 0.1 to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1 to about 20%. In some embodiments, silicates are present at a level of from about 5 to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleach, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP2100949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP2100949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612; 5,227,084; and 4,810,410; WO99/06521; and EP2100949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO2000/32601 and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP2100949, WO9426860 and WO94/26859). In some embodiments, the metal care agent is a zinc salt. In some further embodiments, the cleaning compositions of the present invention comprise from about 0.1% to about 5% by weight of one or more metal care agent.

In some embodiments, the cleaning composition is a high density liquid (HDL) composition having a variant serine protease polypeptide protease. The HDL liquid laundry detergent can comprise a detersive surfactant (10%-40%) comprising anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof and hydrophobic side chain(s) selected from the group consisting of: $C_4$-$C_{25}$ alkyl group, polypropylene, polybutylene, vinyl ester of a saturated $C_2$-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can be any liquid form, for example a liquid or gel form, or any combination thereof. The composition may be in any unit dose form, for example a pouch.

In some embodiments, the cleaning composition is a high density powder (HDD) composition having a variant serine protease polypeptide protease. The HDD powder laundry detergent can comprise a detersive surfactant including anionic detersive surfactants (selected from a group of linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from a group of linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from a group of alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (selected from a group of alkanolamine sulpho-betaines); ampholytic surfactants; semi-polar non-ionic surfactants and mixtures thereof; builders (phosphate free builders [for example zeolite builders examples of which include zeolite A, zeolite X, zeolite P and zeolite MAP in the range of 0 wt % to less than 10 wt %]; phosphate builders [examples of which include sodium tri-polyphosphate in the range of 0 wt % to less than 10 wt %]; citric acid, citrate salts and nitrilotriacetic acid or salt thereof in the range of less than 15 wt %); silicate salt (sodium or potassium silicate or sodium meta-silicate in the range of 0 wt % to less than 10 wt %, or layered silicate (SKS-6)); carbonate salt (sodium carbonate and/or sodium bicarbonate in the range of 0 wt % to less than 10 wt %); and bleaching agents (photobleaches, examples of which include sulfonated zinc phthalocyanines, sulfonated aluminum phthalocyanines, xanthenes dyes, and mixtures thereof; hydrophobic or hydrophilic bleach activators (examples of which include dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof; hydrogen peroxide; sources of hydrogen peroxide (inorganic perhydrate salts examples of which include mono or tetra hydrate sodium salt of perborate, percarbonate, persulfate, perphosphate, or persilicate); preformed hydrophilic and/or hydrophobic peracids (selected from a group consisting of percarboxylic acids and salts, percarbonic acids and salts, perimidic acids and salts, peroxymonosulfuric acids and salts) & mixtures thereof and/or bleach catalyst (such as imine bleach boosters examples of which include iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; metal-containing bleach catalyst for example copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of poly-carboxylic acids and their partially or completely neutralized salts, monomeric polycarboxylic acids and hydroxy-carboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators-organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

In some embodiments, the cleaning composition is borate-free. In some embodiments, the cleaning composition is phosphate-free.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001% to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

Also provided are compositions and methods of treating fabrics (e.g., to desize a textile) using a serine protease polypeptide of the present invention. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

A serine protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A serine protease of the present invention can be applied during or after the weaving to remove these sizing starch or starch derivatives. After weaving, the serine protease can be used to remove the size coating before further processing the fabric to ensure a homogeneous and wash-proof result.

A serine protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

The serine protease polypeptides described herein find further use in the enzyme aided removal of proteins from animals and their subsequent degradation or disposal, such as feathers, skin, hair, hide, and the like. In some instances, immersion of the animal carcass in a solution comprising a serine protease polypeptide of the present invention can act to protect the skin from damage in comparison to the traditional immersion in scalding water or the defeathering process. In one embodiment, feathers can be sprayed with an isolated serine protase polypeptide of the present invention under conditions suitable for digesting or initiating degradation of the plumage. In some embodiments, a serine protease of the present invention can be used, as above, in combination with an oxidizing agent.

In some embodiments, removal of the oil or fat associated with raw feathers is assisted by using a serine protease polypeptide of the present invention. In some embodiments, the serine protease polypeptides are used in compositions for cleaning the feathers as well as to sanitize and partially dehydrate the fibers. In yet other embodiments, the disclosed serine protease polypeptides find use in recovering protein from plumage. In some other embodiments, the serine protease polypeptides are applied in a wash solution in combination with 95% ethanol or other polar organic solvent with or without a surfactant at about 0.5% (v/v).

In a further aspect of the invention, the serine protease polypeptides of the present invention can be used as a component of an animal feed composition, animal feed additive and/or pet food comprising a serine protease and variants thereof. The present invention further relates to a method for preparing such an animal feed composition, animal feed additive composition and/or pet food comprising mixing the serine protease polypeptide with one or more animal feed ingredients and/or animal feed additive ingredients and/or pet food ingredients. Furthermore, the present invention relates to the use of the serine protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

The protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a protease polypeptide of the present invention under conditions suitable for bleaching the paper pulp.

In some embodiments, the pulps are chlorine free pulps bleached with oxygen, ozone, peroxide or peroxyacids. In some embodiments, the protease polypeptides are used in enzyme aided bleaching of pulps produced by modified or continuous pulping methods that exhibit low lignin contents. In some other embodiments, the protease polypeptides are applied alone or preferably in combination with xylanase and/or endoglucanase and/or alpha-galactosidase and/or cellobiohydrolase enzymes.

The protease polypeptides described herein find further use in the enzyme aided removal of proteins from animals and their subsequent degradation or disposal, such as feathers, skin, hair, hide, and the like. In some instances, immersion of the animal carcass in a solution comprising a protease polypeptide of the present invention can act to protect the skin from damage in comparison to the traditional immersion in scalding water or the defeathering process. In one embodiment, feathers can be sprayed with an isolated protease polypeptide of the present invention under conditions suitable for digesting or initiating degradation of the plumage. In some embodiments, a protease of the present invention can be used, as above, in combination with an oxidizing agent.

In some embodiments, removal of the oil or fat associated with raw feathers is assisted by using a protease polypeptide of the present invention. In some embodiments, the protease polypeptides are used in compositions for cleaning the feathers as well as to sanitize and partially dehydrate the fibers. In some other embodiments, the protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

EXAMPLES

The following examples are provided to demonstrate and illustrate certain preferred embodiments and aspects of the present disclosure and should not be construed as limiting. In the experimental disclosure which follows, the following abbreviations apply: ADW (automatic dish washing); BMI (blood/milk/ink); BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); and w/v (weight to volume).

Example 1

Discovery and Identification of Serine Protease BspAP02013

Bacillus sp. 18N1 (Culture Collection Dupont) was selected as a potential source for enzymes useful in industrial applications. To identify enzymes produced by Bacillus sp. 18N1 and the genes that encode these enzymes, the entire genome of Bacillus sp. 18N1 was sequenced using Illumina® sequencing by synthesis (SBS) technology. Genome sequencing and assembly of the sequence data was performed by BaseClear (Leiden, The Netherlands). Contigs were annotated by BioXpr (Namur, Belgium). One of genes identified this way in strain Bacillus sp. 18N1 encodes a protein that showed homology to serine proteases of various other bacteria. The nucleotide sequence of this gene, BspAP02013. n, is depicted in SEQ ID NO:1: TTGAGACGAT TATTTTAGCTCTATTACTAGTAATTTTGATGGCAGTACCGGGACAAGCTGTATTAGCAGGAAATGCGAACGAAGAGGTTAAAGATTATTTAGTTCAATTTAATGGTGCAGCAC AGAAAGGGTTAGTACAAGCATTTGGTATTGATAACGAAGATATTATCCATGAATATGACCTCCTTCCAGTCATGCATCTAAATTTAACAGACAATCAAGCTCGTGGCCTGAAGA ATCATCCTCATGTTCAAATGGTTGAAGAAAATGCTGAGGTAACGAAACTAGCTCAAACAACGCCATGGGGTATCCCTCGTGTTCAAGGAACTGCTGCACAAAATGCAGGCTAT ACAGGAAATGGGGTAAAGGTAGCGATTCTTGATACAGGAATTGATCGCAATCATCC TGATCTTTCTGCTAATGTAAAAGGTGGCCATTCTGTTTTCACTGATTCAGCTAACTCT GACCCATTTTTTGATGGTGATGGACACGGTACTCATGTTGCTGGTACTGTGGCGGCT GTGAATAATGATATTGGGGTTATTGGTGTCGCAAGTGAAGCTTCTCTATATGCGGTA AAGGTATTGAACAATGCGGGTAGTGGTTCATATGCTGGTATTGCCGAGGGAATCGA ATGGGCAATCAATAATGATATCGACATCATTAATATGAGTCTTGGTGGCTCACAAAG TTCTGCTATTTTAAAAACAGTTTAGTGATCTAGCATATGCTGAGGGACTCCTTGTTGTC GCTGCAGCTGGTAATAGTGGAACACGCAGTGGTAGAAATGACACAGTCGGCTACCC TGCTAAATATGACTCAGTTATCGCAGTAGCTGCAACGGATCAAAATAACCAAC GTGC AACATTCTCAAGCACAGGTCCAGCAGTTGAAATCTCAGCTCCTGGAGTAGGCATTCT TAGCACGACGCCAAATAACAATTATGTATCCTTTAATGGAACATCAATGGCTTCTCC ACACGTCGCAGGAGTTGCAGCGCAAGTGTGGCAAGCAAAGCCT-CACTTATCGAATA TTGAGCTTCGTAATCTGTTAAATGACACAGCTATTGATCTAGGATCTTCTACGCAAT ATGGTAATGGATTAGTACAATCATTAGAAGCGATTCAACAA.

The preproenzyme encoded by the BspAP02013. n gene is depicted in SEQ ID NO:2. At the N-terminus, the protein has a signal peptide with a length of 23 amino acids as predicted by SignalP-NN (Emanuelsson et al., Nature Protocols (2007) 2: 953-971). This signal peptide sequence is underlined and in bold in SEQ ID NO:2. The presence of a signal peptide indicates that this serine protease is a secreted enzyme. The enzyme has a pro sequence which is predicted to be 73 amino acids (shown in italics). The sequence of the predicted, fully processed mature chain (BspAP02013, 281 amino acids) is depicted in SEQ ID NO:3.

SEQ ID NO:2 sets forth the amino acid sequence of the serine protease precursor BspAP02013 (the signal peptide sequence is underlined and in bold, the pro sequence is shown in italics):

LRRLFLALLLVILMAVPGQAVLAGNANEEVKDYLVQFNGAAQKGLVQAF

GIDNEDIIHEYDLLPVMHLNLTDNQARGLKNHPHVQMVEENAEVTKLAQ

TTPWGIPRVQGTAAQNAGYTGNGVKVAILDTGIDRNHPDLSANVKGGHS

VFTDSANSDPFFDGDGHGTHVAGTVAAVNNDIGVIGVASEASLYAVKVL

NNAGSGSYAGIAEGIEWAINNDIDIINMSLGGSQSSAILKQFSDLAYAE

GLLVVAAAGNSGTRSGRNDTVGYPAKYDSVIAVAATDQNNQRATFSSTG

PAVEISAPGVGILSTTPNNNYVSFNGTSMASPHVAGVAAQVWQAKPHLS

NIELRNLLNDTAIDLGSSTQYGNGLVQSLEAIQQ.

SEQ ID NO:3 sets forth the predicted amino acid sequence of the mature protease BspAP02013: AQTTPWGIPRVQGTAAQNAGYTGNGVKVAILDTGIDRNHPDLSANVKGG HSVFTDSANSDPFFDGDGHGTHVAGTVAAVNNDIGVIGVASEASLYAVKVLNNAGSGS YAGIAEGIEWAINNDIDIINMSLGGSQSSAILKQFSDLAYAEGLLVVAAAGNSGTRSGRN DTVGYPAKYDSVIAVAATDQNNQRATF SSTGPAVEISAPGVGILSTTPNNNYVSFNGTS MASPHVAGVAAQVWQAKPHLSNIELRNLLNDTAIDLGSSTQYGNGLVQSLEAIQQ.

Example 2

Discovery and Identification of Serine Protease BspM02866

Bacillus sp. WDG290 (Culture Collection Dupont) was selected as a potential source for enzymes useful in industrial applications. To identify enzymes produced by Bacillus sp. WDG290 and the genes that encode these enzymes, the entire genome of Bacillus sp. WDG290 was sequenced using Illumina® sequencing by synthesis (SBS) technology. Genome sequencing and assembly of the sequence data was performed by BaseClear (Leiden, The Netherlands). Contigs were annotated by BioXpr (Namur, Belgium). One of genes identified this way in strain Bacillus sp. WDG290 encodes a protein that showed homology to serine proteases of various other bacteria.

SEQ ID NO:4 sets forth the nucleotide sequence of the BspM02866. n gene: ATGAA GAAATTATTCGTAGTCTGGATGACGCTCATCT TAATGGCTGTGCCGTTTCAGGCAGG GGCCTCAAACGGATCCGGAGACACTCTCGAAGAATACTTA GTACAGTTTAACGGGC CTTCAGCGCATGGGCTGATGCAGGCATTCGGCATT-
GATGAAGCACAGGTGAAAACC GAATTCGAT-
CACCTGCCGGTAGTAAATGTTGCCCTTTCT-
GAAGCTCAGGCAAGAGGC
CTGGCGAACCACCCTCACGTAGAAGCGGTGGAG-
GAGAACGCTGAAGTGCATGCGCT TGGTCA-
GACGGTACCATGGGGCATTCCCCACGTTCAGG-
GAACGGCTGCCCAGGATG
CAGGATTTACAGGAGCCGGTCTTAAGGTGGCAAT-
TCTTGATACAGGAATTGAAGCAT CCCACGAA-
GATCTGTCTGCGAACGTAAAAGGCGGGCACTCTGT
TTTTACCGATTCTG CCAACAGTGATCCGTTCTAC-
GATCCGAACGGACACGGCACACACGTTGCCG-
GAACG GTTGCAGCCGTCGATAACGATCTTGGTGT-
CATCGGCGTCGCTCCCGAAGCGGACCTT
TACGCGGTTAAAGTACTCAGCAACGCCGGAAGCG-
GAAGCATCGCCGGCATTGCAGA
GGGAATCGAATGGTCGATCGATAACGGAATGGA-
TATCATTAATATGAGTCTGGGCG CTTCGCAGG-
GATCTTCCATCCTTGAGCAGTTCTCAAACCTTGCC-
TATGATGAAGGAC
TCCTTGTGGTGGCTGCTGCCGGTAACAGCG-
GAAACCGCGGCGGGAATAACAATACG GTCGGC-
TACCCGGCTGCCTATGACTCTGTTAT-
TGCCGTAGCTGCGGTGGACCAGAAC
AACAATCGCGC-
CACGTTCTCCAGCACAGGCCCGGCTGTT-
GAAATCTCAGCACCCGGC
GTCAACGTCCTCAGCACAACGCCTGGCAACAAT-
TACGCTTCCTACAACGGAACGTCC
ATGGCGTCTCCT-
CACGTAGCAGGCGTAGCCGCCCAGGTATGGCAGG
CGAATCCGGG GCTTTC-
CAACACAGAGCTCCGCCAGCTTCTCAATGATA-
CAGCCGTCAACCTCGGCCC GGCC-
CACCAGTATGGTCACGGCCTAGTCCAGTCACTTGA
TGCGATTAACCAG.

The preproenzyme encoded by the BspM02866. n gene is depicted in SEQ ID NO:5. At the N-terminus, the protein has a signal peptide with a length of 22 amino acids as predicted by SignalP-NN (Emanuelsson et al., Nature Protocols (2007) 2:953-971). This signal peptide sequence is underlined and in bold in SEQ ID NO:5. The presence of a signal peptide indicates that this serine protease is a secreted enzyme. The enzyme has a pro sequence which is predicted to be 74 amino acids (shown in italics). The sequence of the predicted, fully processed mature chain (BspM02866, 281 amino acids) is depicted in SEQ ID NO:6.

SEQ ID NO:5 sets forth the amino acid sequence of the serine protease precursor BspM02866 (the signal peptide sequence is underlined and in bold, the pro sequence is shown in italics):

MKKLFVVWMTLILMAVPFQAGASNGSGDTLEEYLVQFNGPSAHGLMQA

FGIDEAQVKTEFDHLPVVNVALSEAQARGLANHPHVEAVEENAEVHALG

QTVPWGIPHVQGTAAQDAGFTGAGLKVAILDTGIEASHEDLSANVKGGH

SVFTDSANSDPFYDPNGHGTHVAGTVAAVDNDLGVIGVAPEADLYAVKV

LSNAGSGSIAGIAEGIEWSIDNGMDIINMSLGASQGSSILEQFSNLAYD

EGLLVVAAAGNSGNRGGNNNTVGYPAAYDSVIAVAAVDQNNNRATFSST

GPAVEISAPGVNVLSTTPGNNYASYNGTSMASPHVAGVAAQVWQANPGL

SNTELRQLLNDTAVNLGPAHQYGHGLVQSLDAINQ.

SEQ ID NO:6 sets forth the predicted amino acid sequence of the mature protease B spM02866: GQTVPW-GIPHVQGTAAQDAGFTGAGLKVAILDTGIEASHEDL-SANVKGGH SVFTDSANSDPFYDPNGHGTH-VAGTVAAVDNDLGVIGVAPEADLYAVKVLSNAGSGSI AGIAEGIEWSIDNGMDIINMSLGASQGSSILEQFSN-LAYDEGLLVVAAAGNSGNRGGNN NTVGYPAAYDSVIAVAAVDQNNNRATFSSTGPAVEI-SAPGVNVLSTTPGNNYASYNGTS MAS-PHVAGVAAQVWQANPGLSNTELRQLLND-TAVNLGPAHQYGHGLVQSLDAINQ.

Example 3

Discovery and Identification of Serine Protease BspZ00056

Bacillus sp. WDG291 (Culture Collection Dupont) was selected as a potential source for enzymes useful in industrial applications. To identify enzymes produced by Bacillus sp. WDG291 and the genes that encode these enzymes, the entire genome of Bacillus sp. WDG291 was sequenced using Illumina® sequencing by synthesis (SBS) technology. Genome sequencing and assembly of the sequence data was performed by BaseClear (Leiden, The Netherlands). Contigs were annotated by BioXpr (Namur, Belgium). One of genes identified this way in strain Bacillus sp. WDG291 encodes a protein that showed homology to serine proteases of various other bacteria.

SEQ ID NO:7 sets forth the nucleotide sequence of the BspZ00056. n gene: TTGAAA AAATTATT-CACAGTTTGGTTAGCACTCGTTTTACTAGCGAT-TCCCGTATCTGTCGGGG CAGATGCTGGTGGTAAC-GATCAAAGTCAGGATTATTTGGTCCAATTTAACGGA
CCTG CAAGTAAAGGGTTAAT-TAAAGCGTTCGGTGTCGATGAAGGGGACATTCTT-CATACAT ACGACCACCTTCCAGTCGTCCACGT-GAACTTGACTGAAAACCAGGCACGGGGCCTT
GCCAATCACCCACACATCACAACAGTT-GAAGAAAACGCTGAAGTAAAAGCGCTCGG
TCAAACGGTCCCATGGGGCATTC-CACACGTGCAAGGAACTGCGGCTCAAGATGCTG
GGTATACTGGTGCCGGTCTTAAAGTAGCGATTCTT-GATACGGGGATCGACCGTAACC ACGAA-
GACTTGTTTGCTAACGTAAAAGGCGGTCATTCCGT-ATTTACGGATTCCGCAA
ACAGCGATCCATTTTATGATGCTGACGGT-CACGGTACACACGTTGCAGGTACAGTCG
CAGCTGTTGA-
TAACGACCTTGGCGTTGTAGGCGTGGCTTCC-CAAGCTGAGCTGTATG CGGTAAAAGTTCT-
GAACAACTCCGGAAGCGGATCTTATGCAGGTATCG
CTGAAGGA ATTGAATGGTCGATCAACAACG-
GAATGGACATCATCAACATGAGCCTTGGTGGTTCC
CAAAGCTCGTCCATCCTGAAACAGTTCTCTGACT-TAGCTTACGAAGAAGGACTTCTT
GTCGTAGCCGCAGCGGGTAACAGCG-GAAACCGCGGTGGAAACAACGACACTGTCGG
CTACCCGGCGAAATATGACTCTGTAATCGCGGTCGC
TGCCGTCGATCAAAACAACA ACCGTGCTACAT-TCTCTAGTACCGGTCCTGCTGTTGAAAT-
TCAGCTCCTGGTGTGAG CAT-
TCTCAGCCACAACGCCAGGCAACAACTACGCTGCG
TTCAACGGAACTTCCATGGC TTCTCCT-
CACGTAGCCGGCGTGGCAGCT-
CAAGTTTGGCAGGCAAAACCTGAACTATC
AAACGTAGAGCTTCGTAATCTAT- TAAACGAAACTGCAGTGAACCTGGGCGGATCCAACCAATTCGGTCACGGTCTAGTTCAGTCGCTGGATGCGATTCAGCAC.

The preproenzyme encoded by the BspZ00056. n gene is depicted in SEQ ID NO:8. At the N-terminus, the protein has a signal peptide with a length of 24 amino acids as predicted by SignalP-NN (Emanuelsson et al., Nature Protocols (2007) 2:953-971). This signal peptide sequence is underlined and in bold in SEQ ID NO:8. The presence of a signal peptide indicates that this serine protease is a secreted enzyme. The enzyme has a pro sequence which is predicted to be 72 amino acids (shown in italics). The sequence of the predicted, fully processed mature chain (BspZ00056, 281 amino acids) is depicted in SEQ ID NO:9.

SEQ ID NO:8 sets forth the amino acid sequence of the serine protease precursor BspZ00056 (the signal peptide sequence is underlined and in bold, the pro sequence is shown in italics): LKKLFTVWLALVL-LAIPVSVGADAGGNDQSQDYLVQFNGPASKG-LIKAFGVDE GDILHTY-DHLPVVHVNLTENQARGLANHPHITTVEENAEVK ALGQTVPWGIPHVQGTAAQD AGYTGAGLK-VAILDTGIDRNHEDLFANVKGGHSVFTDSANSDPFY-DADGHGTHVAGTV AAVDNDLGVVGVASQAEL-YAVKVLNNSGSGSYAGIAEGIEWSINNGMDIINMSL GGSQ SSSILKQFSDLAYEEGLLVVAAAGNSGNRGG-NNDTVGYPAKYDSVIAVAAVDQNNNRA TFSSTGPAVEISAPGVSILSTTPGNNYAAFNGTSMAS-PHVAGVAAQVWQAKPELSNVEL RNLLNETAVNLGG-SNQFGHGLVQ SLDAIQH.

SEQ ID NO:9 sets forth the predicted amino acid sequence of the mature protease BspZ00056: GQTVPW-GIPHVQGTAAQDAGYTGAGLKVAILDTGIDRNHEDL-FANVKGGH SVFTDSANSDPFYDADGHGTH-VAGTVAAVDNDLGVVGVASQAELYAVKVLNNSGSGS YAGIAEGIEWSINNGMDIINMSLGGSQSSSILKQFSD-LAYEEGLLVVAAAGNSGNRGGNN DTVGYPA-KYDSVIAVAAVDQNNNRATFSSTGPAVEISAPGVSIL-STTPGNNYAAFNGTS MASPHVAGVAAQVWQAKPELSNVELRNLLN-ETAVNLGGSNQFGHGLVQ SLDAIQH.

Example 4

Heterologous Expression of Serine Proteases BspAP02013, BspM02866, and BspZ00056

BspAP02013, BspM02866, and BspZ00056 proteases were produced in B. subtilis using an expression cassette consisting of the B. subtilis aprE promoter, the B. subtilis aprE signal peptide sequence, the native BspAP02013, BspM02866, or BspZ00056 protease pro-peptides, the mature BspAP02013, BspM02866, or BspZ00056 proteases and a BPN' terminator. These cassettes were cloned into the pBN based replicating shuttle vector (Babe' et al. (1998), Biotechnol. Appl. Biochem. 27: 117-124) and a suitable B. subtilis strain was transformed with the vector.

Figure 2:
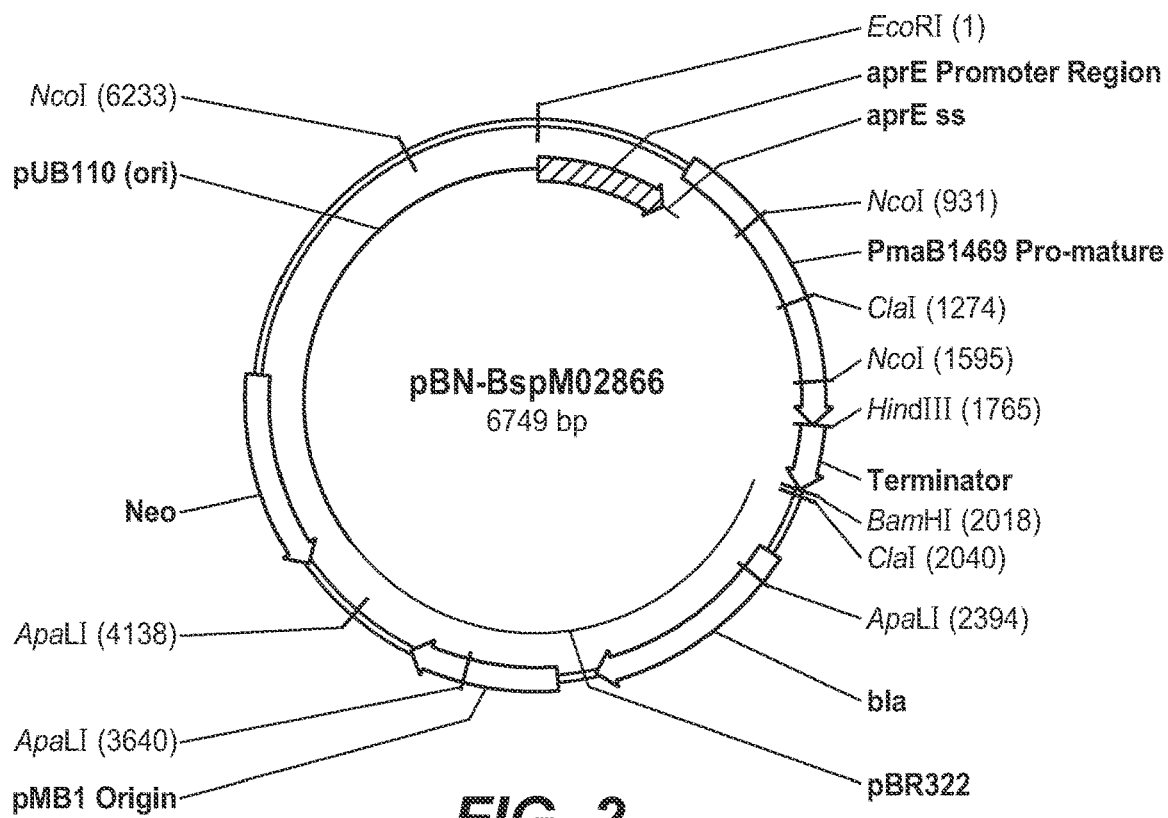
FIG. 2 provides a plasmid map for expression of BspM02866 protease.
Figure 3:
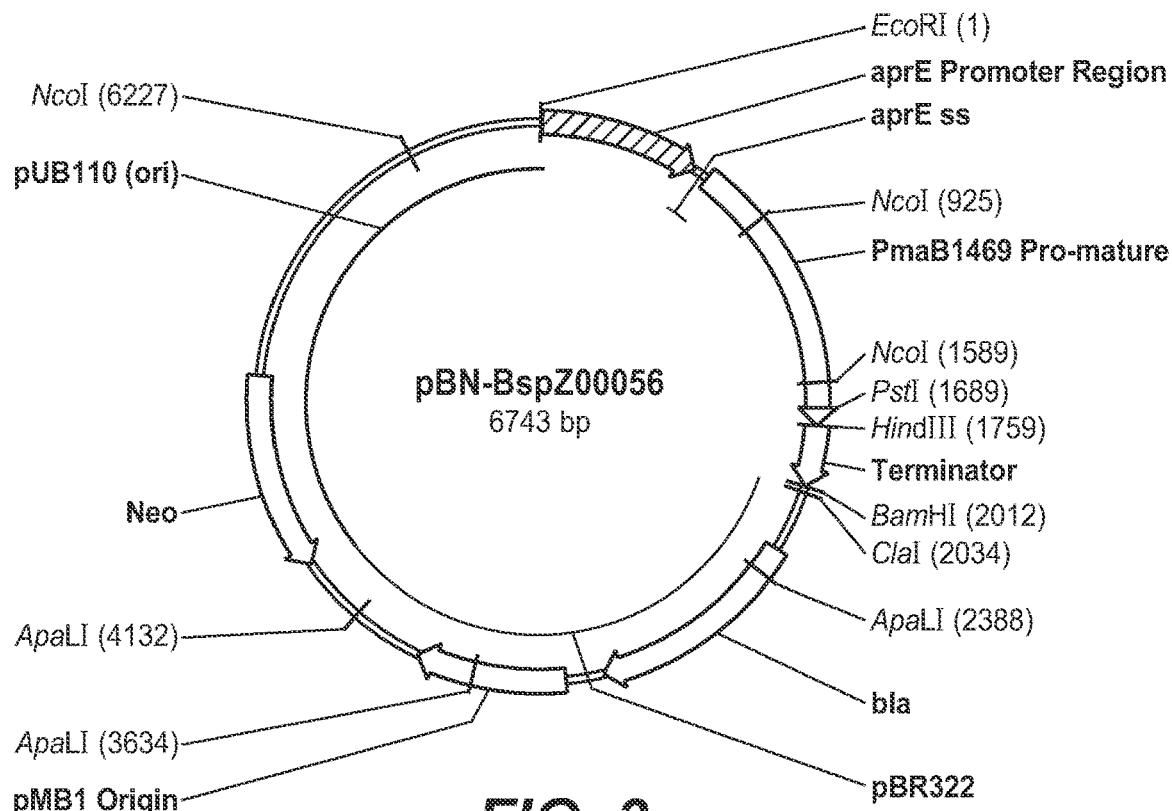
FIG. 3 provides a plasmid map for expression of BspZ00056 protease.

Plasmid maps of the pBN vector containing the BspAP02013gene (pBN-BspAP02013), BspM02866 (pBN-BspM02866), and BspZ00056 gene (pBN-BspZ00056) are shown in FIGS. 1-3, respectively.

To produce BspAP02013, BspM02866, and BspZ00056, suitable B. subtilis transformants containing pBN-BspAP02013, pBN-BspM02866, or pBN-BspZ00056 were cultured in 15 ml Falcon tubes for 16 hours in TSB (broth) with 10 ppm neomycin, and 300 µl of the pre-cultures were added to a 500 mL flask filled with 30 mL of cultivation media (described below) supplemented with 10 ppm neomycin. The flasks were incubated for 48 hours at 32° C. with constant rotational mixing at 180 rpm. Cultures were harvested by centrifugation at 14500 rpm for 20 minutes in conical tubes. The culture supernatants were used for assays. The cultivation media was an enriched semi-defined media based on MOPs buffer, with urea as major nitrogen source, glucose as the main carbon source, and supplemented with 1% soytone for robust cell growth.

Protein Determination by Stain Free Imager Criterion

Protein was quantified by the stain-free Imager Criterion method. The method is based on utilizing stain-free precast PAGE gels, where the intensity of each band will depend on amount of tryptophan residues present in the protein of interest. The Criterion™ TGX (Tris-Glycine extended) Stain-Free™ precast gels for PAGE include unique trihalo compounds. This allows rapid fluorescent detection of proteins with the Gel Doc™ EZ imaging system. The trihalo compounds react with tryptophan residues in a UV-induced reaction to produce fluorescence, which can be easily detected by the Gel Doc EZ imager within gels. Reagents used in the assay: Concentrated (10×) Laemmli Sample Buffer (Kem-En-Tec, Catalogue #42556); either 18 or 26-well Criterion TGX Strain-Free Precast gels (Bio-Rad, Catalogue #567-8124 and 567-8125, respectively); and protein markers "Precision Plus Protein Standards" (Bio-Rad, Catalogue #161-0363). The assay was carried out as follows: 25 µl protein sample and 25 µl 0.5M HCL was added to a 96well-PCR plate on ice for 10 min to inactivate the protease and prevent self-hydrolysis. 50 µl of the acid protein mix was added to 504, sample buffer containing 0.385 mg DTT in the 96well-PCR plate. After that, the chamber was filled by running buffer, and the gel cassette was set. 10µ. L of each sample together with markers was load into each pocket and the electrophoresis was started at 200 V for 35 min. Following electrophoresis, the gel was transferred to Imager. Image Lab software was used for calculation of intensity of each band. By knowing the protein amount and the tryptophan content of the standard sample, the calibration curve can be made. The amount of experimental sample can be determined by extrapolation of the band intensity and tryptophan numbers to protein concentration. The protein quantification method was employed to prepare samples of the BspAP02013, BspM02866, and BspZ00056 proteases used for the assays set forth in Examples 5-8.

N and C-Terminal Amino Acid Determination

In preparation for sequence confirmation, a sample of isolated BspM2866 protein was subjected to a series of chemical treatments in a 10 kDa spinfilter. The sample was denatured and reduced by urea and DTT treatment. A guanidination step was performed to convert lysines to homoarginines to protect lysine side chains from acetylation. Acetylation reaction using iodoacetamide then modifies only the proteins' N-terminal residue. The sample was then mixed with a buffer containing $^{18}O$ water and the enzymes trypsin and chymotrypsin added for digestion. The resulting peptides contained mixtures of $^{18}O$ and $^{16}O$, except for the Carboxyl terminus which retains the native $^{16}O$. The digestion products were separated and analyzed using a Proxeon nano-LC system followed by LTQ Orbitrap (Thermo Fisher) high resolution mass spectrometer. The amino acid sequence was deduced from the MS/MS fragment spectrum of the peptides and the isotopic pattern of the peptides. A sample of BspM2866 protein expressed from plasmid pBN-BspAP02013 was analyzed as described above. The sequence of the mature protein was determined to correspond to SEQ ID NO:6, 281 amino acids, set forth above.

Example 5

Protease Activity of BspAP02013, BspM02866, and BspZ00056

Figure 4:
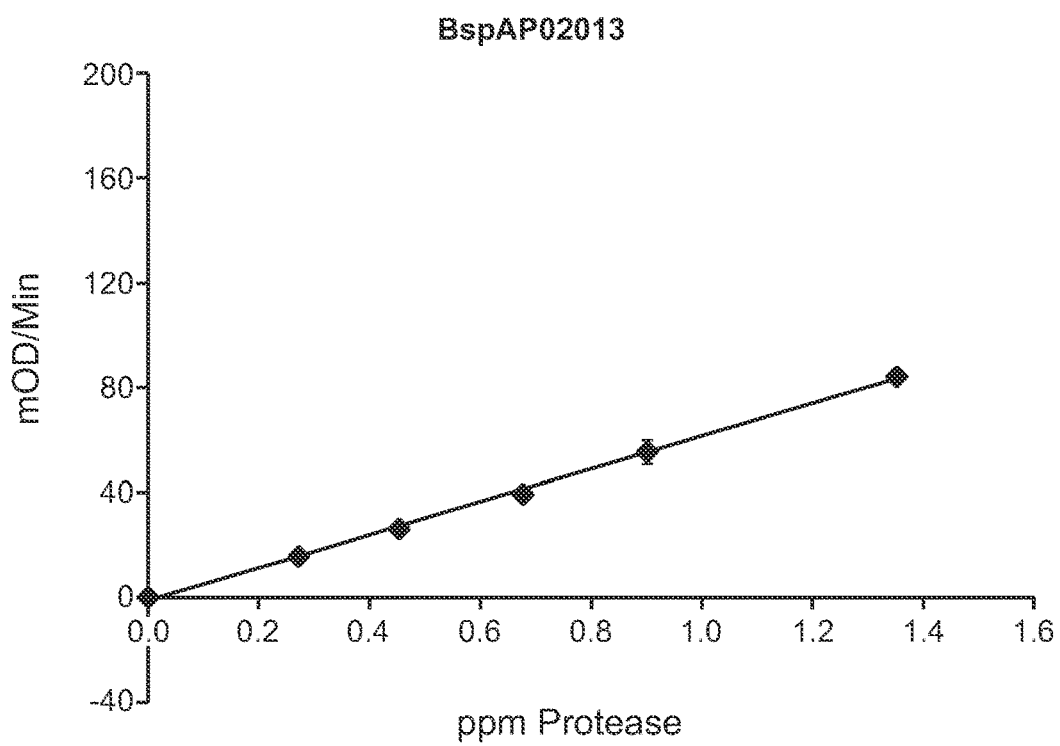
FIG. 4 provides a plot of protease activity of BspAP02013 protease on DMC substrate.
Figure 5:
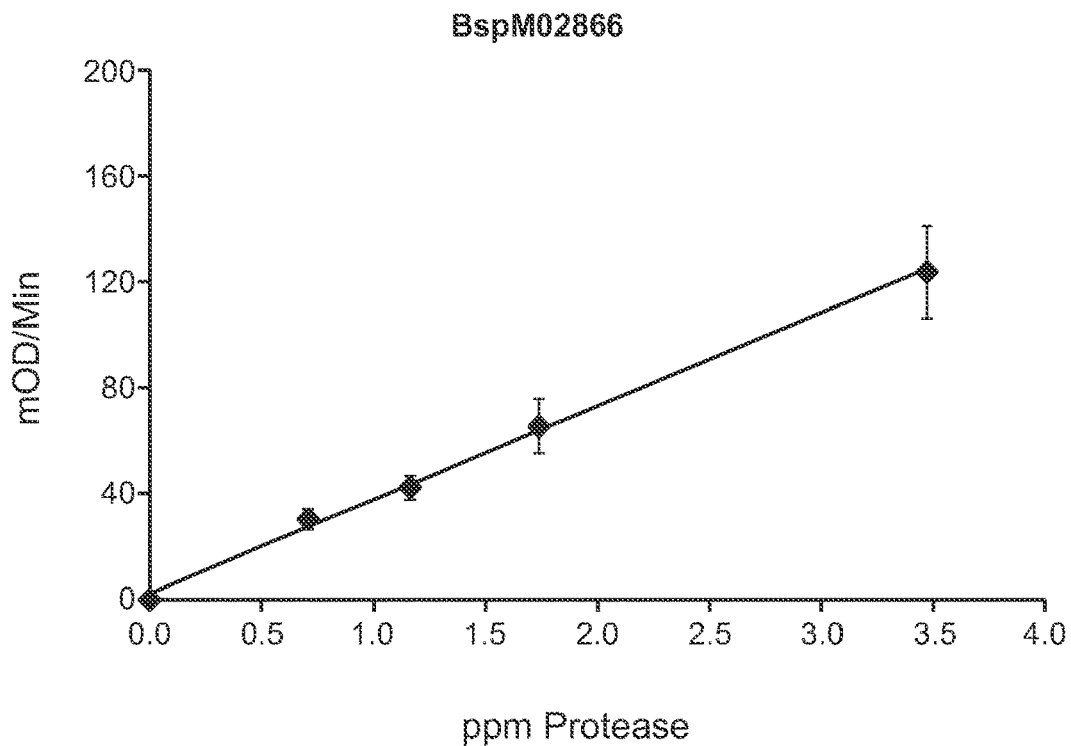
FIG. 5 provides a plot of protease activity of BspM02866 protease on DMC substrate.
Figure 6:
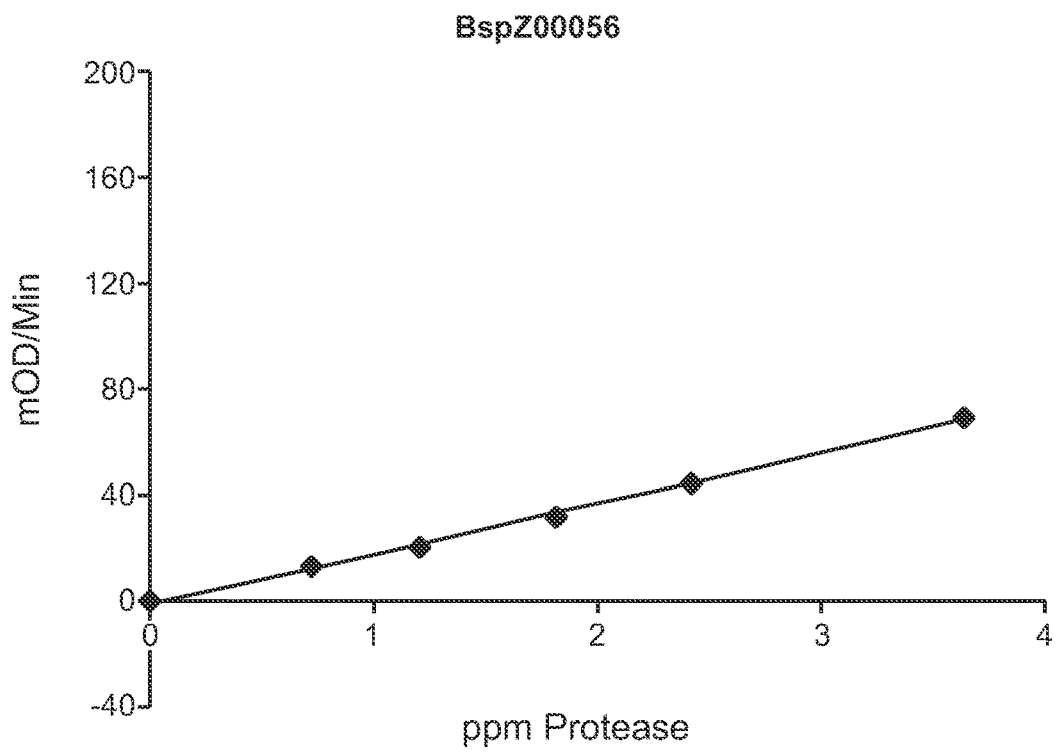
FIG. 6 provides a plot of protease activity of BspZ00056 protease on DMC substrate.

The protease activity of BspAP02013(SEQ ID NO:3), BspM02866(SEQ ID NO:6), and BspZ00056 (SEQ ID NO:9) were tested by measuring the hydrolysis of dimethyl casein (DMC) substrate. The reagent solutions used for the DMC assay were: 2.5% DMC (Sigma) in 100 mM Sodium Carbonate pH 9.5, 0.075% TNBSA (2,4,6-trinitrobenzene sulfonic acid, Thermo Scientific) in Reagent A. Reagent A: 45.4 g $Na_2B_4O_7.10H_2O$ (Merck) in 15 mL 4N NaOH to reach a final volume of 1000 mL in MQ water, Dilution Solution: 10 mM NaCl, 0.1 mM $CaCl_2$, and 0.005% Tween-80. Protease supernatants were diluted in Dilution Solution to appropriate concentration for the assay. A 96-well microtiter plate (MTP) was filled with 95 μl DMC substrate followed by the addition of 5 μl diluted protease supernatant. 100 μL of TNBSA in Reagent A was then added with slow mixing. Activity was measured at 405 nm over 5 min using a SpectraMax plate reader in kinetic mode at RT. The absorbance of a blank containing no protease was subtracted from values. The activity was expressed as mOD/min. The protease activity curves for BspAP02013, BspM02866, and BspZ00056 proteases are shown in FIGS. 4-6, respectively. Using the DMC assay, the specific activity of BspAP02013 was found to be 60 mOD/min/ppm, of BspM02866 was found to be 39 mOD/min/ppm, and of BspZ00056 was found to be 18 mOD/min/ppm. The specific activities of GG36 and BPN' proteases were found to be 54 and 23 mOD/min/ppm, respectively under the same assay conditions.

Example 6 pH Profile of BspAP02013

The pH dependence of proteolytic activity of BspAP02013 (SEQ ID NO:3) was studied using azo-casein as substrate in a 50 mM Acetate/Bis-Tris/HEPES/CHES buffer including 50 mM $CaCl_2$. The activity was measured at pH between 4 to 12 with 1 pH unit increments. One Protaxyme AK tablet (Megazyme, Ireland) was added to a glass test tube together with 1.9 mL of appropriate buffer and a magnet, followed by gentle hydration at 40° C. for 5 min in a temperature controlled water bath fitted with magnetic stirrer. A 100 μL sample of freshly prepared protease (diluted in deionised water to appropriate concentration for the assay) was added to the prehydrated substrate and reaction was carried out at 40° C. for 10 min. To terminate the reaction, 10 mL of a 2% w/v Tris buffer, pH 12 was added, solution was mixed, and the sample was immediately filtered through a Whatman No. 1 filter. The supernatant was collected and the absorbance at 590 nm of the supernatant was measured to quantify the product of the reaction. The absorbance from a buffer-only control was subtracted, and the resulting values were converted to percentages of relative activity, by defining the activity at the optimal pH as 100%. BspAP02013 was determined to maintain ≥50% of activity over the pH range of 8-12 under the conditions of this assay.

Example 7

Temperature Profile of BspAP02013

The temperature dependence of proteolytic activity of BspAP02013 (SEQ ID NO:3) was studied using azo-casein as substrate in a 50 mM Acetate/Bis-Tris/HEPES/CHES buffer including 50 mM $CaCl_2$ at pH 10. The activity was measured at temperatures between 30° C. and 80° C. with 10° C. increments. One Protaxyme AK tablet (Megazyme, Ireland) was added to a glass test tube together with 1.9 mL of appropriate buffer and a magnet stirrer, followed by gentle hydration at set temperatures for 5 min in a temperature controlled water bath fitted with magnetic stirrer. A 100 μl sample of freshly prepared protease (diluted in deionised water to appropriate concentration for the assay) was added to the prehydrated substrate and reaction was carried out at temperatures between 30° C. and 80° C. for 10 min. To terminate the reaction, 10 mL of a 2% w/v Tris buffer pH 12 was added and solution was mixed and filtered immediately through a Whatman No. 1 filter. The supernatant was collected and the absorbance at 590 nm of the supernatant was measured to quantify the product of the reaction. The absorbance from a buffer-only control was subtracted from each sample reading, and the resulting values were converted to percentages of relative activity, by defining the activity at the optimal temperature at 100%. BspAP02013 was determined to retain ≥50% activity over a range of 55° C.-75° C., under the conditions of this assay.

Example 8

Stability Evaluation of Proteases

The stability of BspAP02013 (SEQ ID NO:3) and FNA (SEQ ID NO:10) proteases was determined under various conditions.

SEQ ID NO:10 sets forth the sequence of FNA protease: AQSVPYGVSQIKAPALH SQGYTGSNVKVA-VIDSGIDSSHPDLKVAGGASMVPSETNPFQDNN-SHGTHVAGTVAAL NNSIGVLGVAPSASLYAVKVL-GADGSGQYSWIINGIEWAIANNMDVINMSLGGPSGS AA LKAAVDKAVASGVVVVAAAGNEGTSGSSSTVGYPG KYPSVIAVGAVDSSNQRASFSSV GPELDVMAPGV-SIQSTLPGNKYGALNGTSMASPHVAGAAALIL-SKHPNWTNTQVRSSL ENTTTKLGDSFYYGKGL-INVQAAAQ.

Stability was tested under two stress conditions shown below by measuring the residual proteolytic activity following incubation at set temperatures.

1. LAS/EDTA: 0.02% LAS, 2.1 mM EDTA in 50 mM HEPES pH8, 0.005% Tween 80
2. OMO HDL: 10% OMO Klein & Krachtig liquid detergent (heat inactivated prior to use).

For stressed conditions, diluted enzyme sample was mixed in stress buffers/detergent in a 96-well PCR plate and incubated at 30° C., 40° C., 50° C., 60° C. and 75° C. for 20 min using a Tetrad2 Thermocycler. For the unstressed condition, enzyme was assayed immediately after mixing with stress media to establish a baseline (initial activity). Protease activity under stressed and unstressed conditions was measured by either the hydrolysis of AAPF-pNA or DMC substrate assays described previously. Percent residual activities were calculated by taking a ratio of the stressed to unstressed activity at each temperature and multiplying it by 100. The percent remaining activity for each protease is shown on Tables 1 and 2 for each condition run at the various temperatures.

TABLE 1

Stability of proteases in LAS/EDTA

| Enzyme | Unstressed | Incubation temperature | | | | |
|---|---|---|---|---|---|---|
| | | 30° C. | 40° C. | 50° C. | 60° C. | 75° C. |
| BspAP02013 | 100 | >90 | 69 | 33 | 30 | 31 |
| FNA | 100 | >90 | 84 | 7 | 4 | 1 |

TABLE 2

Stability of proteases in 10% OMO HDL

| Enzyme | Unstressed | Incubation temperature | | | | |
|---|---|---|---|---|---|---|
| | | 30° C. | 40° C. | 50° C. | 60° C. | 75° C. |
| BspAP02013 | 100 | >90 | >90 | 89 | 11 | 1 |
| FNA | 100 | >90 | >90 | 71 | 1 | 1 |

Example 9

Comparison of BspAP02013, BspM02866, and BspZ00056 Protease to Related Molecules Identification of Homologous Proteases Related proteins were identified by a BLAST search (Altschul et al., Nucleic Acids Res, 25:3389-402, 1997) using the mature protein amino acid sequences for BspAP02013 (SEQ ID NO: 3), BspM02866 (SEQ ID NO:6), and BspZ00056 (SEQ ID NO:9) against the NCBI non-redundant protein database and a subset are shown on Tables 4A, 5A, and 6A, resepctively. A similar search was run against the Genome Quest Patent database with search parameters set to default values using the mature protein amino acid sequences for BspAP02013 (SEQ ID NO:3), BspM02866 (SEQ ID NO:6), and BspZ00056 (SEQ ID NO:9) as the query sequence, and a subset are shown in Tables 4B, 5B, and 6B, respectively. Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 4A

List of sequences with percent identity to BspAP02013 protein identified from the NCBI non-redundant protein database

| Accession # | PID | Organism | Sequence Length | Alignment Length |
|---|---|---|---|---|
| WP_047973355 | 96 | Bacillus sp. LL01 | 377 | 281 |
| YP_003427361.1/ WP_012957833 | 90 | Bacillus pseudofirmus OF4 | 379 | 281 |
| ERN55058/ WP_022626565.1 | 90 | Bacillus marmarensis DSM 21297 | 291 | 281 |
| WP_026690432 | 85 | Bacillus aurantiacus | 377 | 280 |
| BAD02409 | 75 | Bacillus sp. KSM-LD1 | 404 | 279 |
| WP_035661169 | 73 | Bacillus akibai JCM 9157 | 378 | 281 |
| WP_027963976 | 71 | Halalkalibacillus halophilus | 372 | 279 |
| WP_027965007 | 71 | Halalkalibacillus halophilus | 377 | 280 |
| WP_026475840 | 70 | Alkaliphilus transvaalensis | 382 | 279 |
| WP_017185212.1 | 65 | Alkalibacillus haloalkalphilus | 374 | 278 |
| ADC49870 | 58 | B pseudofirmus | 374 | 280 |
| BAD21128 | 58 | Bacillus sp KSM-LD1 SB | 377 | 280 |
| AAC43580 | 58 | Bacillus sp. SprC | 378 | 280 |
| CAJ70731 | 57 | Bacillus licheniformis | 379 | 280 |
| BAD11988 | 57 | Bacillus sp. KSM-LD1 SA | 376 | 280 |
| YP_003972439 | 57 | B atrophaeus | 382 | 280 |
| WP_006636716 | 56 | B sonorensis | 378 | 280 |
| AAC43581 | 56 | Bacillus sp SprD | 379 | 280 |
| BAN09118 | 56 | B subtilis | 381 | 280 |
| CAA24990 | 56 | Bacillus amyloliquefaciens | 376 | 280 |
| AAA22212 | 55 | B alcalophilus | 380 | 275 |
| P29600 | 55 | Bacillus lentus | 269 | 275 |
| BAD63300 | 55 | B clausii | 380 | 275 |
| WP_010333625 | 55 | B mojavensis | 381 | 275 |
| WP_010329279 | 55 | B vallismortis | 381 | 280 |
| BAA06157 | 54 | Bacillus sp. Sendai | 382 | 274 |
| ADN04910 | 54 | B circulans | 275 | 273 |
| AFP23380.1 | 54 | B lehensis | 276 | 273 |
| WP_007497196 | 54 | B stratosphericus | 383 | 273 |
| ADK11996 | 54 | B pumilus | 383 | 273 |
| AGC81872.1 | 54 | B methylotrophicus | 382 | 280 |
| CAA74536 | 53 | B subtilis str168 | 381 | 280 |
| ABY25856 | 53 | G stearothermophilus | 382 | 280 |

TABLE 4B

List of sequences with percent identity to BspAP02013 protein identified from the Genome Quest database

| Patent ID # | PID | Organism | Sequence Length | Alignment Length |
|---|---|---|---|---|
| JP2003325186-0001 | 74.6 | Bacillus sp. | 404 | 279 |
| JP2004313043-0024 | 59.6 | Bacillus sp. KSM-9865 | 379 | 280 |
| U.S. Pat. No. 5,275,945-0002 | 59.3 | Bacillus sp. | 377 | 280 |
| JP2012524542-0052 | 59.1 | Alkaliphilus transvaalensis | 274 | 279 |
| JP2008022828-0032 | 58.9 | Bacillus sp. | 352 | 280 |
| JP2004154003-0007 | 58.6 | Bacillus sp. KSM-LD1 | 276 | 280 |
| U.S. Pat. No. 5,677,163-0001 | 58.2 | Bacillus sp. | 275 | 280 |
| JP2013500714-0412 | 57.9 | Bacillus licheniformis | 274 | 280 |
| JP2013500714-0403 | 57.9 | Bacillus mojavensis | 274 | 280 |
| WO2013159032-0004 | 57.9 | Bacillus licheniformis | 274 | 280 |
| WO2012139964-0002 | 57.9 | Bacillus sp. | 274 | 280 |
| U.S. Pat. No. 8,110,391-0009 | 57.9 | Bacillus licheniformis | 274 | 280 |
| CN101215534 | 57.5 | B. licheniformis; YP1A, CCTCC NO: M207021 | 379 | 280 |
| WO02077289-0009 | 58.6 | Bacillus sp. | 372 | 273 |
| JP2013500005-0025 | 57.1 | Bacillus licheniformis | 274 | 280 |
| US20050113273-0016 | 57.1 | Bacillus licheniformis | 274 | 280 |
| U.S. Pat. No. 8,076,107-0001 | 57.1 | Bacillus licheniformis | 379 | 280 |
| KR20080017039-0005 | 57.1 | Bacillus licheniformis | 379 | 280 |

TABLE 5A

List of sequences with percent identity to BspM02866 protein identified from the NCBI non-redundant protein database

| Accession # | PID | Organism | Sequence Length | Alignment Length |
|---|---|---|---|---|
| WP_026690432 | 86 | Bacillus aurantiacus | 377 | 281 |
| YP_003427361.1/ WP_012957833 | 81 | Bacillus pseudofirmus OF4 | 379 | 280 |
| WP_047973355 | 81 | Bacillus sp. LL01 | 377 | 281 |
| ERN55058/ WP_022626565.1 | 80 | Bacillus marmarensis DSM 21297 | 291 | 280 |
| WP_035661169 | 75 | Bacillus akibai JCM 9157 | 378 | 280 |
| BAD02409 | 75 | Bacillus sp. KSM-LD1 | 404 | 279 |
| WP_026475840 | 71 | Alkaliphilus transvaalensis | 382 | 279 |
| WP_027965007 | 71 | Halalkalibacillus halophilus | 377 | 280 |
| WP_027963976 | 70 | Halalkalibacillus halophilus | 372 | 278 |
| WP_017185212.1 | 66 | Alkalibacillus haloalkaliphilus | 374 | 278 |
| AAC43580 | 61 | Bacillus sp. SprC | 378 | 278 |
| AAC43581 | 60 | Bacillus sp SprD | 379 | 272 |
| BAD21128 | 60 | Bacillus sp KSM-LD1 SB | 377 | 272 |
| BAD11988 | 59 | Bacillus sp. KSM-LD1 SA | 376 | 272 |
| CAJ70731 | 58 | Bacillus licheniformis | 379 | 272 |
| WP_006636716 | 56 | B sonorensis | 378 | 272 |
| ADC49870 | 56 | B pseudofirmus | 374 | 274 |
| BAD63300 | 55 | B clausii | 380 | 274 |
| YP_003972439 | 55 | B atrophaeus | 383 | 272 |
| AAA22212 | 54 | B alcalophilus | 380 | 274 |
| P29600 | 54 | Bacillus lentus | 269 | 274 |
| BAA06157 | 53 | Bacillus sp. Sendai | 382 | 274 |
| ADN04910 | 53 | B circulans | 275 | 279 |
| AFP23380.1 | 53 | B lehensis | 276 | 279 |
| WP_007497196 | 53 | B stratosphericus | 383 | 279 |
| ADK11996 | 53 | B pumilus | 383 | 279 |
| AGC81872.1 | 53 | B methylotrophicus | 382 | 272 |
| BAN09118 | 52 | B subtilis | 381 | 272 |
| CAA24990 | 52 | Bacillus amyloliquefaciens | 376 | 272 |
| ABY25856 | 52 | G stearothermophilus | 383 | 272 |
| WP_010333625 | 51 | B mojavensis | 381 | 272 |
| WP_010329279 | 51 | B vallismortis | 381 | 272 |
| CAA74536 | 50 | B subtilis str168 | 381 | 272 |

TABLE 5B

List of sequences with percent identity to BspM02866 protein identified from the Genome Quest database

| Patent ID # | PID | Organism | Sequence Length | Alignment Length |
|---|---|---|---|---|
| JP2003325186-0001 | 74.9 | *Bacillus* sp. | 404 | 279 |
| U.S. Pat. No. 5,677,163-0001 | 61.2 | *Bacillus* sp | 275 | 278 |
| JP2004313043-0022 | 60.7 | *Bacillus* sp. KSM-9865 | 275 | 272 |
| U.S. Pat. No. 5,677,163-0007 | 60.3 | *Bacillus* sp. | 276 | 272 |
| JP2004154003-0007 | 60.3 | *Bacillus* sp. KSM-LD1 | 276 | 272 |
| JP2004313043-0021 | 59.9 | *Bacillus* sp. KSM-KP43 | 275 | 272 |
| JP2013500714-0416 | 58.5 | *Bacillus licheniformis* | 269 | 272 |
| KR20080017039-0002 | 58.5 | *Bacillus licheniformis* | 379 | 272 |
| U.S. Pat. No. 8,530,218-0052 | 56.6 | *Alkaliphilus transvaalensis* | 274 | 279 |
| U.S. Pat. No. 5,371,008 | 58.1 | *Bacillus licheniformis*; (*carlsbergensis*) | 275 | 272 |
| CN101215534 | 58.1 | *B. licheniformis*; YP1A, CCTCC NO: M207021 | 379 | 272 |
| WO9739130 | 58.1 | *Bacillus licheniformis*; strain PWD-1 | 379 | 272 |
| WO2011014278 | 57.7 | *Bacillus licheniformis* ATCC 14580 | 274 | 272 |
| WO2011009859 | 57.7 | *Bacillus amyloliquefaciens* | 274 | 272 |

TABLE 6A

List of sequences with percent identity to BspZ00056 protein identified from the NCBI non-redundant protein database

| Accession # | PID | Organism | Sequence Length | Alignment Length |
|---|---|---|---|---|
| WP_026690432 | 86 | *Bacillus aurantiacus* | 377 | 281 |
| YP_003427361.1/ WP_012957833 | 81 | *Bacillus pseudofirmus* OF4 | 379 | 279 |
| WP_047973355 | 81 | *Bacillus* sp. LL01 | 377 | 280 |
| ERN55058/ WP_022626565.1 | 80 | *Bacillus marmarensis* DSM 21297 | 291 | 280 |
| BAD02409 | 78 | *Bacillus* sp. KSM-LD1 | 404 | 278 |
| WP_035661169 | 75 | *Bacillus akibai* JCM 9157 | 378 | 280 |
| WP_026475840 | 71 | *Alkaliphilus transvaalensis* | 382 | 279 |
| WP_027965007 | 71 | *Halalkalibacillus halophilus* | 377 | 280 |
| WP_027963976 | 70 | *Halalkalibacillus halophilus* | 372 | 278 |
| WP_017185212.1 | 67 | *Alkalibacillus haloalkaliphilus* | 374 | 280 |
| WP_010192403.1 | 61 | *Bacillus* sp. m3-13 | 381 | 279 |
| AAC43580 | 60 | *Bacillus* sp. SprC | 378 | 279 |
| BAD21128 | 58 | *Bacillus* sp KSM-LD1 SB | 377 | 279 |
| BAD11988 | 58 | *Bacillus* sp. KSM-LD1 SA | 376 | 279 |
| AAC43581 | 57 | *Bacillus* sp SprD | 379 | 279 |
| CAJ70731 | 57 | *Bacillus licheniformis* | 379 | 279 |
| WP_006636716 | 57 | *B sonorensis* | 378 | 280 |
| ADC49870 | 56 | *B pseudofirmus* | 374 | 279 |
| YP_003972439 | 56 | *B atrophaeus* | 382 | 279 |
| BAD63300 | 54 | *B clausii* | 380 | 274 |
| ADN04910 | 54 | *B circulans* | 275 | 272 |
| AFP23380.1 | 54 | *B lehensis* | 276 | 272 |
| WP_007497196 | 54 | *B stratosphericus* | 383 | 272 |
| ADK11996 | 54 | *B pumilus* | 383 | 272 |
| AAA22212 | 53 | *B alcalophilus* | 380 | 274 |
| P29600 | 53 | *Bacillus lentus* | 269 | 274 |
| BAN09118 | 53 | *B subtilis* | 381 | 279 |
| CAA24990 | 53 | *Bacillus amyloliquefaciens* | 376 | 279 |
| WP_010333625 | 53 | *B mojavensis* | 381 | 279 |
| BAA06157 | 52 | *Bacillus* sp. Sendai | 382 | 274 |
| AGC81872.1 | 52 | *B methylotrophicus* | 382 | 279 |
| ABY25856 | 51 | *G stearothermophilus* | 382 | 279 |
| WP_010329279 | 51 | *B vallismortis* | 381 | 279 |
| CAA74536 | 51 | *B subtilis* str168 | 381 | 279 |

TABLE 6B

List of sequences with percent identity to BspZ00056 protein identified from the Genome Quest database

| Patent ID # | PID | Organism | Sequence Length | Alignment Length |
|---|---|---|---|---|
| JP2003325186-0001 | 78.1 | *Bacillus* sp. | 404 | 278 |
| WO9406915-0001 | 60.2 | *Bacillus* sp | 275 | 279 |
| JP2004313043-0022 | 58.8 | *Bacillus* sp. KSM-9865 | 275 | 279 |
| JP2004065171-0007 | 58.4 | *Bacillus* sp. KSM-LD1 | 376 | 279 |
| WO9855634 | 58.1 | *Bacillus licheniformis* | 274 | 279 |
| JP2004313043 | 58.1 | *Bacillus* sp. KSM-KP43 | 379 | 279 |
| JP2013500714-0403 | 57.7 | *Bacillus mojavensis* | 274 | 279 |
| U.S. Pat. No. 7,087,415-0014 | 57.7 | *Bacillus licheniformis* | 379 | 279 |
| CN101215534 | 57.4 | *B. licheniformis*; YP1A, CCTCC NO: M207021 | 379 | 279 |
| WO9739130 | 57.4 | *Bacillus licheniformis*; strain PWD-1 | 379 | 279 |
| WO2011009859 | 57.0 | *Bacillus amyloliquefaciens* | 274 | 279 |
| U.S. Pat. No. 8,530,218-0052 | 56.8 | *Alkaliphilus transvaalensis* | 274 | 278 |

Alignment of Homologous Sequences

Figure 8:
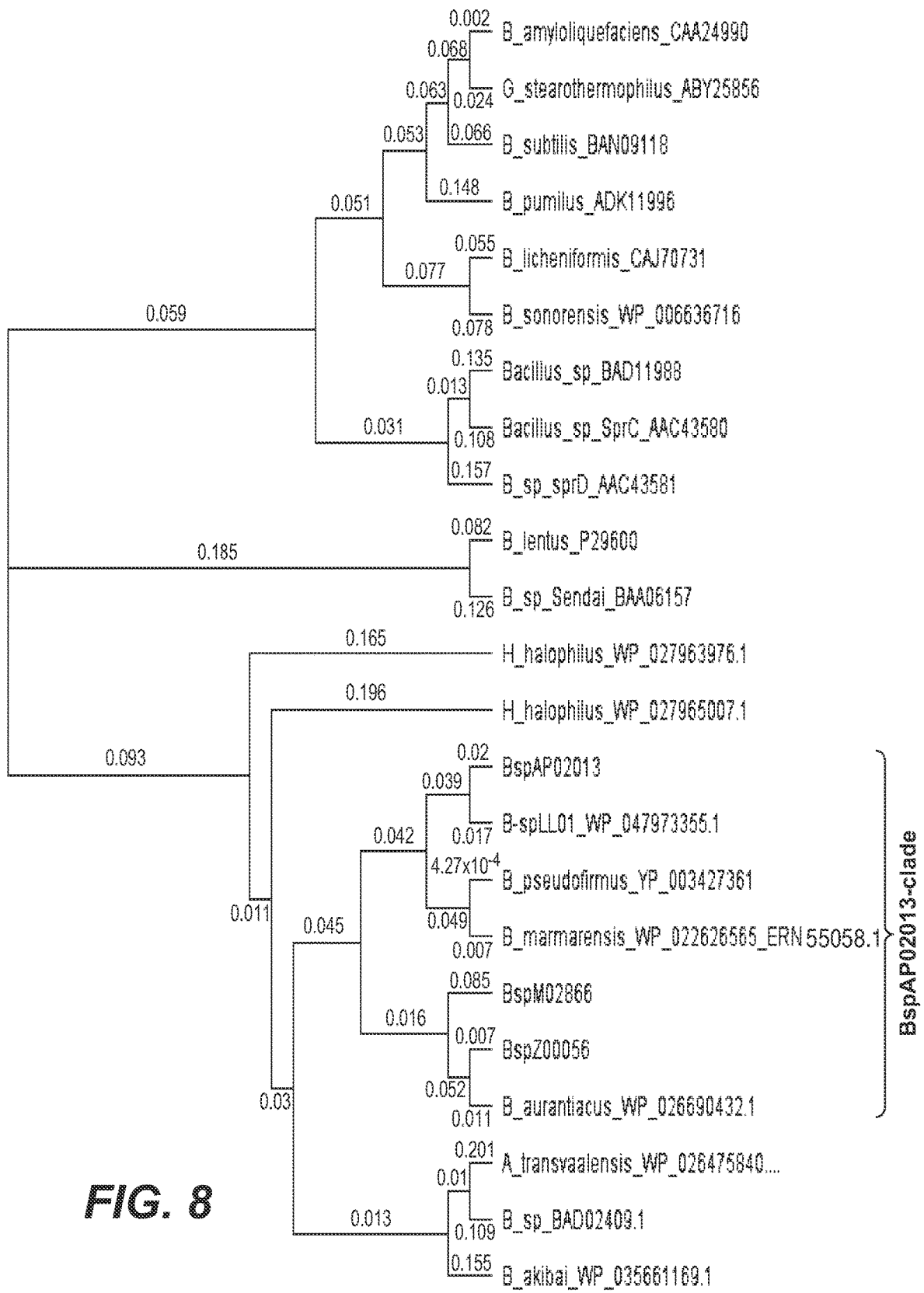
FIG. 8 provides phylogenetic tree of subtilisins including BspAP02013, BspM02866, and BspZ00056.

An alignment of the mature protein amino acid sequences for BspAP02013 (SEQ ID NO:3), BspM02866 (SEQ ID NO:6), and BspZ00056 (SEQ ID NO:9) with the sequences of the mature forms of various subtilisins from Tables 4A, 5A, and 6A is shown in FIGS. 7A-7E. The sequences were aligned using CLUSTALW software (Thompson et al., Nucleic Acids Research, 22:4673-4680, 1994) with the default parameters. A phylogenetic tree for amino acid sequences of the mature forms of the subtilisins from FIGS. 7A-7E was built using the Geneious Tree builder program (Biomatters Ltd.) and is set forth in FIG. 8. The sequences were entered in the Vector NTI Advance suite and a Guide Tree was created using the Neighbor Joining (NJ) method (Saitou and Nei, Mol Biol Evol, 4:406-425, 1987). The tree construction was calculated using the following parameters: Kimura's correction for sequence distance and ignoring positions with gaps. MEGA6 was used to display the tree shown in FIG. 8.

Example 10

Unique Features of BspAP02013-Clade Ssubtilisins

A structure based alignment of the following proteases: BspAP02013 (SEQ ID NO:3), BspM02866 (SEQ ID NO:6), BspZ00056 (SEQ ID NO:9), *B. pseudofirmus* OF4 (NCBI Accession No. YP_003427361.1), BPN' subtilisin from *B. amyloliquefaciens* (pdb entry 2STI), and *B. lentus* subtilisin (pdb entry 1JEA), was performed using the "align" option in the Molecular Operating Environment (MOE) software (Chemical Computing Group, Montreal, Quebec, Canada) to look for structural similarities (FIG. 9). The alignment applies conserved structural motifs as an additional guide to conventional sequence alignment. This alignment was performed using standard program defaults present in the 2012.10 distribution of MOE.

As shown in FIG. 9, the structural alignment of subtilisins BspAP02013, BspM02866, BspZ00056, and YP_003427361.1 (*B. pseudofirmus* OF4) sequences show a common pattern of three insertions relative to the sequences of subtilisins: BPN' from *B. amyloliquefaciens* and subtilisin from *B. lentus*, for which three dimensional structures are available (pdb entries 2ST1 and 1JEA, respectively). The numbering of residues in the 1JEA and 1CSE structures is with respect to subtilisin BPN'; while the numbering of residues for BspAP02013 and all other proteases shown is the consecutive linear sequence. The insertions follow residues L42, N56 and T158 in BPN' subtilisin.

It can be seen that the BspAP02013-clade subtilisins can be characterized by a common motif over the sequence that begins with the catalytic Aspartic acid (D32) of the serine protease triad and ends with the catalytic Histidine (H68) of the catalytic triad according to BspAP02013 numbering. The motif includes two insertions each adding 2 amino acid residues that can be seen in FIG. 9(box).

Figure 10:
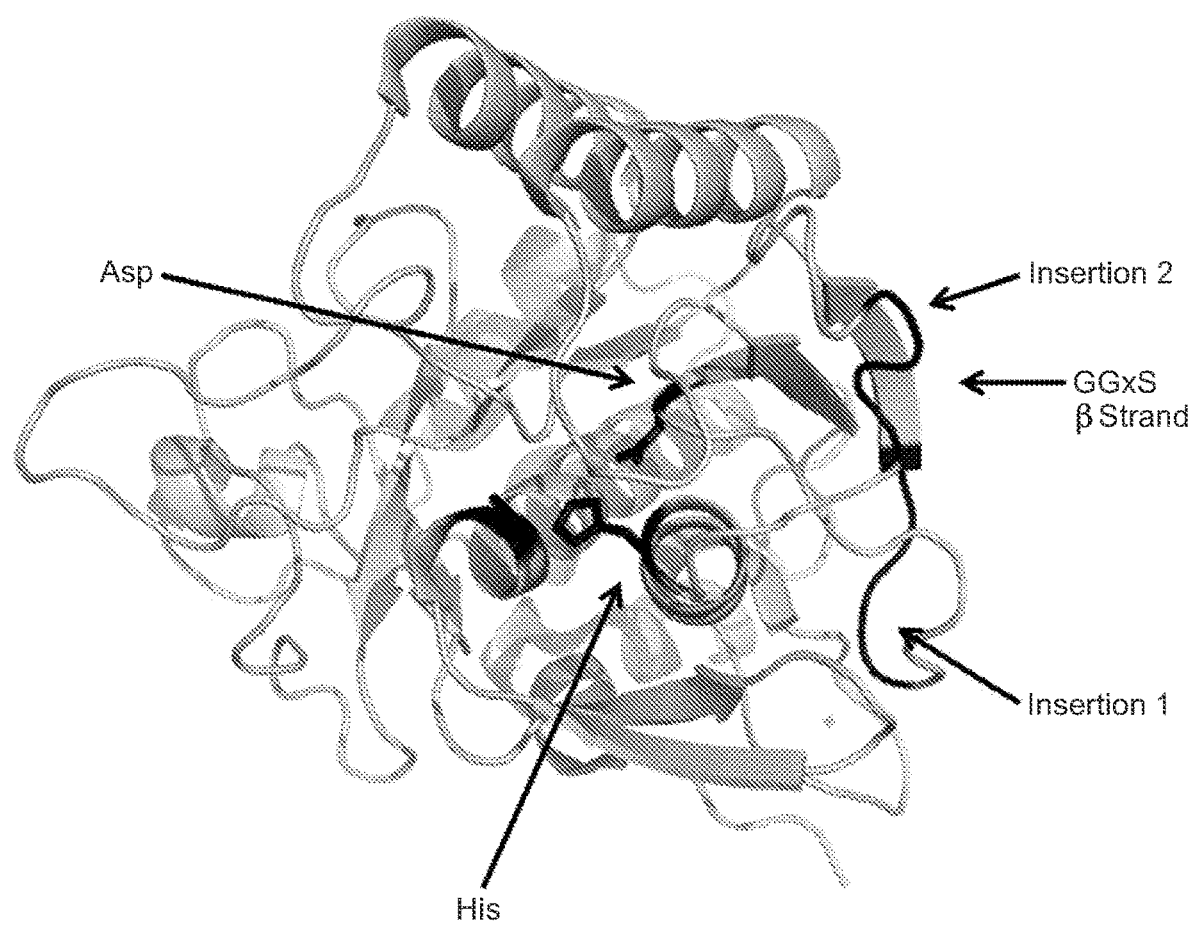
FIG. 10 illustrates the potential structural consequences of sequence motif changes found in the BspAP02013-clade subtilisins.

These insertions are expected to occur in two loops common to the overall tertiary fold of subtilisin enzymes. The location of these insertions are illustrated in FIG. 10 using the known structure of subtilisin BPN' as a reference. The motif segment is highlighted in black using the BPN' subtilisin structure as a reference (in light gray). The catalytic Aspartic acid and Histidine residue side chains, of the catalytic triad common to all serine proteinases are shown as sticks. The segment that connects the catalytic Aspartic Acid (D32) and Histidine (H68) of the subtilisin catalytic triad comprises two loops and the outermost strand of the central beta sheet. This strand includes the GGXS portion of the BspAP02013-clade motif and is indicated by an arrow in FIG. 10. The two motif insertions are proposed to occur in loops indicated by the arrows. Insertion 1 enlarged the first loop and insertion 2, the second loop. The loop containing Insertion 1 occurs in a loop extending from the catalytic Aspartic acid to a beta strand at the edge of the beta sheet GGXS strand. The loop containing insertion 2 follows the GGXS strand and leads into the catalytic Histidine.

The BspA02013-clade motif can be characterized by Motif 1: DTGIXXXHXDLXX XXXGGXSVFTDSXXXXXXXXDXXGH (SEQ ID NO:11), wherein X is any amino acid and collectively can indicate regions of insertion and deletion. In the instances shown in FIG. 9, the BspA02013-clade motif can be characterized by Motif 2: DTGIXXXHXDLX$_a$XXXXGGX SVFTDSXXXXXXXXDXXGH (SEQ ID NO:12), wherein X is any amino acid and X$_a$ is T, S or F, wherein X and X$_a$ can collectively indicate regions of insertion and deletion. In the instances shown in FIG. 9, the BspA02013-clade motif can be characterized by Motif 3: DTGIXXXHX DLXXXXXGGXSVFTDSXXX$_b$XXXXDXXGH (SEQ ID NO:13), wherein X is any amino acid and X$_b$ is S or R. In the instances shown in FIG. 9, the BspA02013-clade motif can be characterized by Motif 4: DTGIXXXHXDLX$_a$XXXXGGXSVFTDSXXX$_b$XXXXD XXGH (SEQ ID NO:14), wherein X is any amino acid, X$_a$ is T, S or F, and X$_b$ is S or R. The BspAP02013, BspM02866, BspZ00056, YP_003427361(*B. pseudofirmus* OF4) and ERN55058/WP_022626565 (*B. marmarensis*) subtilisins which have been identified as BspAP02013-clade subtilisins based on shared sequence motifs outlined in FIG. 9, also cluster together in the phylogenetic tree built using various bacterial subtilisins shown on FIG. 8, with a distance of 0.08.

The amino acid identity across the mature forms of various subtilisins from Tables 4A, 5A, and 6A is shown on Table 7 below, wherein the percent amino acid identity is calculated over the 281 residues of the BspAP02013 mature sequence.

TABLE 7

| Mature enzyme | Percent amino acid sequence identity |||||||||||| 
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| 1. BspAP02013 |  | 80.8 | 85.4 | 96.1 | 90.4 | 89.7 | 69 | 84.7 | 70.8 | 73 | 74 | 70.1 |
| 2. BspM02866 | 80.8 |  | 86.8 | 80.8 | 80.4 | 79.7 | 70.5 | 86.1 | 70.8 | 74.7 | 74.4 | 68.3 |
| 3. BspZ00056 | 85.4 | 86.8 |  | 85.8 | 86.8 | 86.1 | 71.2 | 98.2 | 71.9 | 74.7 | 77.2 | 71.9 |
| 4. B-spLL01_WP_047973355 | 96.1 | 80.8 | 85.8 |  | 89.3 | 88.6 | 68.7 | 85.1 | 69.8 | 74 | 75.1 | 69.4 |
| 5. B_pseudofirmus_YP_003427361 | 90.4 | 80.4 | 86.8 | 89.3 |  | 99.3 | 69.8 | 86.5 | 70.8 | 74 | 75.4 | 70.8 |
| 6. B_marmarensis_WP_022626565_ERN55058 | 89.7 | 79.7 | 86.1 | 88.6 | 99.3 |  | 69 | 85.8 | 70.8 | 73.7 | 75.1 | 70.5 |
| 7. A_transvaalensis_WP_026475840 | 69 | 70.5 | 71.2 | 68.7 | 69.8 | 69 |  | 70.5 | 63.3 | 69 | 73 | 65.1 |
| 8. B_aurantiacus_WP_026690432 | 84.7 | 86.1 | 98.2 | 85.1 | 86.5 | 85.8 | 70.5 |  | 71.9 | 75.4 | 77.2 | 71.2 |
| 9. H_halophilus_WP_027965007 | 70.8 | 70.8 | 71.9 | 69.8 | 70.8 | 70.8 | 63.3 | 71.9 |  | 68.3 | 68.7 | 68.7 |
| 10. B_akibai_WP_035661169 | 73 | 74.7 | 74.7 | 74 | 74 | 73.7 | 69 | 75.4 | 68.3 |  | 76.2 | 66.5 |
| 11. B_sp_BAD02409 | 74 | 74.4 | 77.2 | 75.1 | 75.4 | 75.1 | 73 | 77.2 | 68.7 | 76.2 |  | 68.6 |
| 12. H_halophilus_WP_027963976 | 70.1 | 68.3 | 71.9 | 69.4 | 70.8 | 70.5 | 65.1 | 71.2 | 68.7 | 66.5 | 68.6 |  |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

```
                        SEQUENCE LISTING

<160> NUMBER OF SEQ ID NOS: 53

<210> SEQ ID NO 1
<211> LENGTH: 1131
<212> TYPE: DNA
<213> ORGANISM: unknown
<220> FEATURE:
<223> OTHER INFORMATION: Bacillus sp. 18N1

<400> SEQUENCE: 1
ttgagacgat tatttttagc tctattacta gtaattttga tggcagtacc gggacaagct      60
gtattagcag gaaatgcgaa cgaagaggtt aaagattatt tagttcaatt taatggtgca     120
gcacagaaag ggttagtaca agcatttggt attgataaca aagatattat ccatgaatat     180
gacctccttc cagtcatgca tctaaattta acagacaatc aagctcgtgg cctgaagaat     240
catcctcatg ttcaaatggt tgaagaaaat gctgaggtaa cgaaactagc tcaaacaacg     300
ccatggggta tccctcgtgt tcaaggaact gctgcacaaa atgcaggcta tacaggaaat     360
ggggtaaagg tagcgattct tgatacagga attgatcgca atcatcctga tctttctgct     420
aatgtaaaag gtggccattc tgttttcact gattcagcta actctgaccc attttttgat     480
ggtgatggac acggtactca tgttgctggt actgtggcgc ctgtgaataa tgatattggg     540
gttattggtg tcgcaagtga agcttctcta tatgcggtaa aggtattgaa caatgcgggt     600
agtggttcat atgctggtat tgccgaggga atcgaatggg caatcaataa tgatatcgac     660
atcattaata tgagtcttgg tggctcacaa agttctgcta ttttaaaaca gtttagtgat     720
ctagcatatg ctgagggact ccttgttgtc gctgcagctg gtaatagtgg aacacgcagt     780
ggtagaaatg acacagtcgg ctaccctgct aaatatgact cagttatcgc agtagctgca     840
acggatcaaa ataaccaacg tgcaacattc tcaagcacag gtccagcagt tgaaatctca     900
```

```
gctcctggag taggcattct tagcacgacg ccaaataaca attatgtatc ctttaatgga      960
acatcaatgg cttctccaca cgtcgcagga gttgcagcgc aagtgtggca agcaaagcct     1020
cacttatcga atattgagct tcgtaatctg ttaaatgaca cagctattga tctaggatct     1080
tctacgcaat atggtaatgg attagtacaa tcattagaag cgattcaaca a              1131
```

<210> SEQ ID NO 2
<211> LENGTH: 377
<212> TYPE: PRT
<213> ORGANISM: unknown
<220> FEATURE:
<223> OTHER INFORMATION: Bacillus sp. 18N1

<400> SEQUENCE: 2

```
Leu Arg Arg Leu Phe Leu Ala Leu Leu Leu Val Ile Leu Met Ala Val
1               5                   10                  15

Pro Gly Gln Ala Val Leu Ala Gly Asn Ala Asn Glu Glu Val Lys Asp
            20                  25                  30

Tyr Leu Val Gln Phe Asn Gly Ala Ala Gln Lys Gly Leu Val Gln Ala
        35                  40                  45

Phe Gly Ile Asp Asn Glu Asp Ile Ile His Glu Tyr Asp Leu Leu Pro
    50                  55                  60

Val Met His Leu Asn Leu Thr Asp Asn Gln Ala Arg Gly Leu Lys Asn
65                  70                  75                  80

His Pro His Val Gln Met Val Glu Glu Asn Ala Glu Val Thr Lys Leu
                85                  90                  95

Ala Gln Thr Thr Pro Trp Gly Ile Pro Arg Val Gln Gly Thr Ala Ala
            100                 105                 110

Gln Asn Ala Gly Tyr Thr Gly Asn Gly Val Lys Val Ala Ile Leu Asp
        115                 120                 125

Thr Gly Ile Asp Arg Asn His Pro Asp Leu Ser Ala Asn Val Lys Gly
    130                 135                 140

Gly His Ser Val Phe Thr Asp Ser Ala Asn Ser Asp Pro Phe Phe Asp
145                 150                 155                 160

Gly Asp Gly His Gly Thr His Val Ala Gly Thr Val Ala Ala Val Asn
                165                 170                 175

Asn Asp Ile Gly Val Ile Gly Val Ala Ser Glu Ala Ser Leu Tyr Ala
            180                 185                 190

Val Lys Val Leu Asn Asn Ala Gly Ser Gly Ser Tyr Ala Gly Ile Ala
        195                 200                 205

Glu Gly Ile Glu Trp Ala Ile Asn Asn Asp Ile Asp Ile Ile Asn Met
    210                 215                 220

Ser Leu Gly Gly Ser Gln Ser Ser Ala Ile Leu Lys Gln Phe Ser Asp
225                 230                 235                 240

Leu Ala Tyr Ala Glu Gly Leu Leu Val Val Ala Ala Gly Asn Ser
                245                 250                 255

Gly Thr Arg Ser Gly Arg Asn Asp Thr Val Gly Tyr Pro Ala Lys Tyr
            260                 265                 270

Asp Ser Val Ile Ala Val Ala Ala Thr Asp Gln Asn Asn Gln Arg Ala
        275                 280                 285

Thr Phe Ser Ser Thr Gly Pro Ala Val Glu Ile Ser Ala Pro Gly Val
    290                 295                 300

Gly Ile Leu Ser Thr Thr Pro Asn Asn Asn Tyr Val Ser Phe Asn Gly
305                 310                 315                 320

Thr Ser Met Ala Ser Pro His Val Ala Gly Val Ala Ala Gln Val Trp
```

```
                        325                 330                 335
Gln Ala Lys Pro His Leu Ser Asn Ile Glu Leu Arg Asn Leu Leu Asn
                340                 345                 350

Asp Thr Ala Ile Asp Leu Gly Ser Ser Thr Gln Tyr Gly Asn Gly Leu
            355                 360                 365

Val Gln Ser Leu Glu Ala Ile Gln Gln
        370                 375

<210> SEQ ID NO 3
<211> LENGTH: 281
<212> TYPE: PRT
<213> ORGANISM: unknown
<220> FEATURE:
<223> OTHER INFORMATION: Bacillus sp. 18N1

<400> SEQUENCE: 3

Ala Gln Thr Thr Pro Trp Gly Ile Pro Arg Val Gln Gly Thr Ala Ala
1               5                   10                  15

Gln Asn Ala Gly Tyr Thr Gly Asn Gly Val Lys Val Ala Ile Leu Asp
            20                  25                  30

Thr Gly Ile Asp Arg Asn His Pro Asp Leu Ser Ala Asn Val Lys Gly
        35                  40                  45

Gly His Ser Val Phe Thr Asp Ser Ala Asn Ser Asp Pro Phe Phe Asp
    50                  55                  60

Gly Asp Gly His Gly Thr His Val Ala Gly Thr Val Ala Ala Val Asn
65                  70                  75                  80

Asn Asp Ile Gly Val Ile Gly Val Ala Ser Glu Ala Ser Leu Tyr Ala
                85                  90                  95

Val Lys Val Leu Asn Asn Ala Gly Ser Gly Ser Tyr Ala Gly Ile Ala
            100                 105                 110

Glu Gly Ile Glu Trp Ala Ile Asn Asn Asp Ile Asp Ile Ile Asn Met
        115                 120                 125

Ser Leu Gly Gly Ser Gln Ser Ser Ala Ile Leu Lys Gln Phe Ser Asp
    130                 135                 140

Leu Ala Tyr Ala Glu Gly Leu Leu Val Ala Ala Ala Gly Asn Ser
145                 150                 155                 160

Gly Thr Arg Ser Gly Arg Asn Asp Thr Val Gly Tyr Pro Ala Lys Tyr
                165                 170                 175

Asp Ser Val Ile Ala Val Ala Ala Thr Asp Gln Asn Asn Gln Arg Ala
            180                 185                 190

Thr Phe Ser Ser Thr Gly Pro Ala Val Glu Ile Ser Ala Pro Gly Val
        195                 200                 205

Gly Ile Leu Ser Thr Thr Pro Asn Asn Asn Tyr Val Ser Phe Asn Gly
    210                 215                 220

Thr Ser Met Ala Ser Pro His Val Ala Gly Val Ala Ala Gln Val Trp
225                 230                 235                 240

Gln Ala Lys Pro His Leu Ser Asn Ile Glu Leu Arg Asn Leu Leu Asn
                245                 250                 255

Asp Thr Ala Ile Asp Leu Gly Ser Ser Thr Gln Tyr Gly Asn Gly Leu
            260                 265                 270

Val Gln Ser Leu Glu Ala Ile Gln Gln
        275                 280

<210> SEQ ID NO 4
<211> LENGTH: 1131
<212> TYPE: DNA
```

<213> ORGANISM: unknown
<220> FEATURE:
<223> OTHER INFORMATION: Bacillus sp. WDG290

<400> SEQUENCE: 4

```
atgaagaaat tattcgtagt ctggatgacg ctcatcttaa tggctgtgcc gtttcaggca      60
ggggcctcaa acggatccgg agacactctc gaagaatact tagtacagtt taacgggcct     120
tcagcgcatg gcctgatgca ggcattcggc attgatgaag cacaggtgaa aaccgaattc     180
gatcacctgc cggtagtaaa tgttgccctt tctgaagctc aggcaagagg cctggcgaac     240
caccctcacg tagaagcggt ggaggagaac gctgaagtgc atgcgcttgg tcagacggta     300
ccatggggca ttccccacgt tcagggaacg gctgcccagg atgcaggatt tacaggagcc     360
ggtcttaagg tggcaattct tgatacagga attgaagcat cccacgaaga tctgtctgcg     420
aacgtaaaag gcgggcactc tgtttttacc gattctgcca acagtgatcc gttctacgat     480
ccgaacggac acggcacaca cgttgccgga acggttgcag ccgtcgataa cgatcttggt     540
gtcatcggcg tcgctcccga agcggacctt tacgcggtta agtactcag caacgccgga     600
agcggaagca tcgccggcat tgcagaggga tcgaatggt cgatcgataa cggaatggat     660
atcattaata tgagtctggg cgcttcgcag ggatcttcca tccttgagca gttctcaaac     720
cttgcctatg atgaaggact ccttgtggtg gctgctgccg gtaacagcgg aaaccgcggc     780
gggaataaca atacggtcgg ctacccggct gcctatgact ctgttattgc cgtagctgcg     840
gtggaccaga caacaatcg cgccacgttc tccagcacag gcccggctgt tgaaatctca     900
gcacccggcg tcaacgtcct cagcacaacg cctggcaaca attacgcttc ctacaacgga     960
acgtccatgg cgtctcctca cgtagcaggc gtagccgccc aggtatggca ggcgaatccg    1020
gggctttcca acacagagct ccgccagctt ctcaatgata cagccgtcaa cctcggcccg    1080
gcccaccagt atggtcacgg cctagtccag tcacttgatg cgattaacca g            1131
```

<210> SEQ ID NO 5
<211> LENGTH: 377
<212> TYPE: PRT
<213> ORGANISM: unknown
<220> FEATURE:
<223> OTHER INFORMATION: Bacillus sp. WDG290

<400> SEQUENCE: 5

```
Met Lys Lys Leu Phe Val Val Trp Met Thr Leu Ile Leu Met Ala Val
1               5                   10                  15

Pro Phe Gln Ala Gly Ala Ser Asn Gly Ser Gly Asp Thr Leu Glu Glu
            20                  25                  30

Tyr Leu Val Gln Phe Asn Gly Pro Ser Ala His Gly Leu Met Gln Ala
        35                  40                  45

Phe Gly Ile Asp Glu Ala Gln Val Lys Thr Glu Phe Asp His Leu Pro
    50                  55                  60

Val Val Asn Val Ala Leu Ser Glu Ala Gln Ala Arg Gly Leu Ala Asn
65                  70                  75                  80

His Pro His Val Glu Ala Val Glu Glu Asn Ala Glu Val His Ala Leu
                85                  90                  95

Gly Gln Thr Val Pro Trp Gly Ile Pro His Val Gln Gly Thr Ala Ala
            100                 105                 110

Gln Asp Ala Gly Phe Thr Gly Ala Gly Leu Lys Val Ala Ile Leu Asp
        115                 120                 125

Thr Gly Ile Glu Ala Ser His Glu Asp Leu Ser Ala Asn Val Lys Gly
```

```
                130             135             140
Gly His Ser Val Phe Thr Asp Ser Ala Asn Ser Asp Pro Phe Tyr Asp
145                 150                 155                 160

Pro Asn Gly His Gly Thr His Val Ala Gly Thr Val Ala Ala Val Asp
                165                 170                 175

Asn Asp Leu Gly Val Ile Gly Val Ala Pro Glu Ala Asp Leu Tyr Ala
            180                 185                 190

Val Lys Val Leu Ser Asn Ala Gly Ser Gly Ser Ile Ala Gly Ile Ala
        195                 200                 205

Glu Gly Ile Glu Trp Ser Ile Asp Asn Gly Met Asp Ile Ile Asn Met
210                 215                 220

Ser Leu Gly Ala Ser Gln Gly Ser Ser Ile Leu Glu Gln Phe Ser Asn
225                 230                 235                 240

Leu Ala Tyr Asp Glu Gly Leu Leu Val Ala Ala Gly Asn Ser
                245                 250                 255

Gly Asn Arg Gly Gly Asn Asn Asn Thr Val Gly Tyr Pro Ala Ala Tyr
                260                 265                 270

Asp Ser Val Ile Ala Val Ala Val Asp Gln Asn Asn Asn Arg Ala
            275                 280                 285

Thr Phe Ser Ser Thr Gly Pro Ala Val Glu Ile Ser Ala Pro Gly Val
290                 295                 300

Asn Val Leu Ser Thr Thr Pro Gly Asn Asn Tyr Ala Ser Tyr Asn Gly
305                 310                 315                 320

Thr Ser Met Ala Ser Pro His Val Ala Gly Val Ala Ala Gln Val Trp
                325                 330                 335

Gln Ala Asn Pro Gly Leu Ser Asn Thr Glu Leu Arg Gln Leu Leu Asn
                340                 345                 350

Asp Thr Ala Val Asn Leu Gly Pro Ala His Gln Tyr Gly His Gly Leu
                355                 360                 365

Val Gln Ser Leu Asp Ala Ile Asn Gln
                370                 375

<210> SEQ ID NO 6
<211> LENGTH: 281
<212> TYPE: PRT
<213> ORGANISM: unknown
<220> FEATURE:
<223> OTHER INFORMATION: Bacillus sp. WDG290

<400> SEQUENCE: 6

Gly Gln Thr Val Pro Trp Gly Ile Pro His Val Gln Gly Thr Ala Ala
1               5                   10                  15

Gln Asp Ala Gly Phe Thr Gly Ala Gly Leu Lys Val Ala Ile Leu Asp
                20                  25                  30

Thr Gly Ile Glu Ala Ser His Glu Asp Leu Ser Ala Asn Val Lys Gly
            35                  40                  45

Gly His Ser Val Phe Thr Asp Ser Ala Asn Ser Asp Pro Phe Tyr Asp
        50                  55                  60

Pro Asn Gly His Gly Thr His Val Ala Gly Thr Val Ala Ala Val Asp
65                  70                  75                  80

Asn Asp Leu Gly Val Ile Gly Val Ala Pro Glu Ala Asp Leu Tyr Ala
                85                  90                  95

Val Lys Val Leu Ser Asn Ala Gly Ser Gly Ser Ile Ala Gly Ile Ala
                100                 105                 110

Glu Gly Ile Glu Trp Ser Ile Asp Asn Gly Met Asp Ile Ile Asn Met
```

```
                  115                 120                 125
Ser Leu Gly Ala Ser Gln Gly Ser Ser Ile Leu Glu Gln Phe Ser Asn
        130                 135                 140

Leu Ala Tyr Asp Glu Gly Leu Leu Val Val Ala Ala Gly Asn Ser
145                 150                 155                 160

Gly Asn Arg Gly Gly Asn Asn Asn Thr Val Gly Tyr Pro Ala Ala Tyr
                165                 170                 175

Asp Ser Val Ile Ala Val Ala Ala Val Asp Gln Asn Asn Asn Arg Ala
            180                 185                 190

Thr Phe Ser Ser Thr Gly Pro Ala Val Glu Ile Ser Ala Pro Gly Val
        195                 200                 205

Asn Val Leu Ser Thr Thr Pro Gly Asn Asn Tyr Ala Ser Tyr Asn Gly
    210                 215                 220

Thr Ser Met Ala Ser Pro His Val Ala Gly Val Ala Ala Gln Val Trp
225                 230                 235                 240

Gln Ala Asn Pro Gly Leu Ser Asn Thr Glu Leu Arg Gln Leu Leu Asn
                245                 250                 255

Asp Thr Ala Val Asn Leu Gly Pro Ala His Gln Tyr Gly His Gly Leu
            260                 265                 270

Val Gln Ser Leu Asp Ala Ile Asn Gln
        275                 280

<210> SEQ ID NO 7
<211> LENGTH: 1131
<212> TYPE: DNA
<213> ORGANISM: unknown
<220> FEATURE:
<223> OTHER INFORMATION: Bacillus sp. WDG290

<400> SEQUENCE: 7
ttgaaaaaat tattcacagt ttggttagca ctcgttttac tagcgattcc cgtatctgtc      60
ggggcagatg ctggtggtaa cgatcaaagt caggattatt tggtccaatt taacggacct    120
gcaagtaaag ggttaattaa agcgttcggt gtcgatgaag gggacattct tcatacatac    180
gaccaccttc cagtcgtcca cgtgaacttg actgaaaacc aggcacgggg ccttgccaat    240
cacccacaca tcacaacagt tgaagaaaac gctgaagtaa aagcgctcgg tcaaacggtc    300
ccatggggca ttccacacgt gcaaggaact gcggctcaag atgctgggta tactggtgcc    360
ggtcttaaag tagcgattct tgatacgggg atcgaccgta accacgaaga cttgtttgct    420
aacgtaaaag gcggtcattc cgtatttacg gattccgcaa acagcgatcc attttatgat    480
gctgacggtc acggtacaca cgttgcaggt acagtcgcag ctgttgataa cgaccttggc    540
gttgtaggcg tggcttccca agctgagctg tatgcggtaa aagttctgaa caactccgga    600
agcggatctt atgcaggtat cgctgaagga attgaatggt cgatcaacaa cggaatggac    660
atcatcaaca tgagccttgg tggttcccaa agctcgtcca tcctgaaaca gttctctgac    720
ttagcttacg aagaaggact tcttgtcgta gccgcagcgg gtaacagcgg aaaccgcggt    780
ggaaacaacg acactgtcgg ctacccggcg aaatatgact ctgtaatcgc ggtcgctgcc    840
gtcgatcaaa acaacaaccg tgctacattc tctagtaccg gtcctgctgt tgaaatttca    900
gctcctggtg tgagcattct cagcacaacg ccaggcaaca actacgctgc gttcaacgga    960
acttccatgg cttctcctca cgtagccggc gtggcagctc aagtttggca ggcaaaacct   1020
gaactatcaa acgtagagct tcgtaatcta ttaaacgaaa ctgcagtgaa cctgggcgga   1080
tccaaccaat tcggtcacgg tctagttcag tcgctggatg cgattcagca c             1131
```

<210> SEQ ID NO 8
<211> LENGTH: 377
<212> TYPE: PRT
<213> ORGANISM: unknown
<220> FEATURE:
<223> OTHER INFORMATION: Bacillus sp. WDG290

<400> SEQUENCE: 8

```
Leu Lys Lys Leu Phe Thr Val Trp Leu Ala Leu Val Leu Leu Ala Ile
1               5                   10                  15

Pro Val Ser Val Gly Ala Asp Ala Gly Gly Asn Asp Gln Ser Gln Asp
            20                  25                  30

Tyr Leu Val Gln Phe Asn Gly Pro Ala Ser Lys Gly Leu Ile Lys Ala
        35                  40                  45

Phe Gly Val Asp Glu Gly Asp Ile Leu His Thr Tyr Asp His Leu Pro
50                  55                  60

Val Val His Val Asn Leu Thr Glu Asn Gln Ala Arg Gly Leu Ala Asn
65                  70                  75                  80

His Pro His Ile Thr Thr Val Glu Glu Asn Ala Glu Val Lys Ala Leu
                85                  90                  95

Gly Gln Thr Val Pro Trp Gly Ile Pro His Val Gln Gly Thr Ala Ala
            100                 105                 110

Gln Asp Ala Gly Tyr Thr Gly Ala Gly Leu Lys Val Ala Ile Leu Asp
        115                 120                 125

Thr Gly Ile Asp Arg Asn His Glu Asp Leu Phe Ala Asn Val Lys Gly
130                 135                 140

Gly His Ser Val Phe Thr Asp Ser Ala Asn Ser Asp Pro Phe Tyr Asp
145                 150                 155                 160

Ala Asp Gly His Gly Thr His Val Ala Gly Thr Val Ala Ala Val Asp
                165                 170                 175

Asn Asp Leu Gly Val Val Gly Val Ala Ser Gln Ala Glu Leu Tyr Ala
            180                 185                 190

Val Lys Val Leu Asn Asn Ser Gly Ser Gly Ser Tyr Ala Gly Ile Ala
        195                 200                 205

Glu Gly Ile Glu Trp Ser Ile Asn Asn Gly Met Asp Ile Ile Asn Met
210                 215                 220

Ser Leu Gly Gly Ser Gln Ser Ser Ile Leu Lys Gln Phe Ser Asp
225                 230                 235                 240

Leu Ala Tyr Glu Glu Gly Leu Leu Val Ala Ala Ala Gly Asn Ser
                245                 250                 255

Gly Asn Arg Gly Gly Asn Asn Asp Thr Val Gly Tyr Pro Ala Lys Tyr
            260                 265                 270

Asp Ser Val Ile Ala Val Ala Val Asp Gln Asn Asn Asn Arg Ala
        275                 280                 285

Thr Phe Ser Ser Thr Gly Pro Ala Val Glu Ile Ser Ala Pro Gly Val
290                 295                 300

Ser Ile Leu Ser Thr Thr Pro Gly Asn Asn Tyr Ala Ala Phe Asn Gly
305                 310                 315                 320

Thr Ser Met Ala Ser Pro His Val Ala Gly Val Ala Ala Gln Val Trp
                325                 330                 335

Gln Ala Lys Pro Glu Leu Ser Asn Val Glu Leu Arg Asn Leu Leu Asn
            340                 345                 350

Glu Thr Ala Val Asn Leu Gly Gly Ser Asn Gln Phe Gly His Gly Leu
        355                 360                 365
```

```
Val Gln Ser Leu Asp Ala Ile Gln His
    370                 375
```

<210> SEQ ID NO 9
<211> LENGTH: 281
<212> TYPE: PRT
<213> ORGANISM: unknown
<220> FEATURE:
<223> OTHER INFORMATION: Bacillus sp. WDG290

<400> SEQUENCE: 9

```
Gly Gln Thr Val Pro Trp Gly Ile Pro His Val Gln Gly Thr Ala Ala
1               5                   10                  15

Gln Asp Ala Gly Tyr Thr Gly Ala Gly Leu Lys Val Ala Ile Leu Asp
                20                  25                  30

Thr Gly Ile Asp Arg Asn His Glu Asp Leu Phe Ala Asn Val Lys Gly
            35                  40                  45

Gly His Ser Val Phe Thr Asp Ser Ala Asn Ser Asp Pro Phe Tyr Asp
        50                  55                  60

Ala Asp Gly His Gly Thr His Val Ala Gly Thr Val Ala Ala Val Asp
65                  70                  75                  80

Asn Asp Leu Gly Val Val Gly Val Ala Ser Gln Ala Glu Leu Tyr Ala
                85                  90                  95

Val Lys Val Leu Asn Asn Ser Gly Ser Gly Ser Tyr Ala Gly Ile Ala
            100                 105                 110

Glu Gly Ile Glu Trp Ser Ile Asn Asn Gly Met Asp Ile Ile Asn Met
        115                 120                 125

Ser Leu Gly Gly Ser Gln Ser Ser Ile Leu Lys Gln Phe Ser Asp
130                 135                 140

Leu Ala Tyr Glu Glu Gly Leu Leu Val Ala Ala Ala Gly Asn Ser
145                 150                 155                 160

Gly Asn Arg Gly Gly Asn Asn Asp Thr Val Gly Tyr Pro Ala Lys Tyr
                165                 170                 175

Asp Ser Val Ile Ala Val Ala Ala Val Asp Gln Asn Asn Asn Arg Ala
            180                 185                 190

Thr Phe Ser Ser Thr Gly Pro Ala Val Glu Ile Ser Ala Pro Gly Val
        195                 200                 205

Ser Ile Leu Ser Thr Thr Pro Gly Asn Tyr Ala Ala Phe Asn Gly
210                 215                 220

Thr Ser Met Ala Ser Pro His Val Ala Gly Val Ala Ala Gln Val Trp
225                 230                 235                 240

Gln Ala Lys Pro Glu Leu Ser Asn Val Glu Leu Arg Asn Leu Leu Asn
                245                 250                 255

Glu Thr Ala Val Asn Leu Gly Gly Ser Asn Gln Phe Gly His Gly Leu
            260                 265                 270

Val Gln Ser Leu Asp Ala Ile Gln His
        275                 280
```

<210> SEQ ID NO 10
<211> LENGTH: 275
<212> TYPE: PRT
<213> ORGANISM: artificial sequence
<220> FEATURE:
<223> OTHER INFORMATION: mutation of BPN'

<400> SEQUENCE: 10

```
Ala Gln Ser Val Pro Tyr Gly Val Ser Gln Ile Lys Ala Pro Ala Leu
```

-continued

```
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
                35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
                115                 120                 125

Pro Ser Gly Ser Ala Ala Leu Lys Ala Ala Val Asp Lys Ala Val Ala
 130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
                195                 200                 205

Leu Pro Gly Asn Lys Tyr Gly Ala Leu Asn Gly Thr Ser Met Ala Ser
 210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
275
```

```
<210> SEQ ID NO 11
<211> LENGTH: 37
<212> TYPE: PRT
<213> ORGANISM: unknown
<220> FEATURE:
<223> OTHER INFORMATION: wherein the initial D is the active site
      Aspartic acid, the terminal H is the active site Histidine, and X
      is any amino acid
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
```

```
<221> NAME/KEY: MISC_FEATURE
<222> LOCATION: (26)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 11

Asp Thr Gly Ile Xaa Xaa Xaa His Xaa Asp Leu Xaa Xaa Xaa Xaa Xaa
1               5                   10                  15

Gly Gly Xaa Ser Val Phe Thr Asp Ser Xaa Xaa Xaa Xaa Xaa Xaa
            20                  25                  30

Asp Xaa Xaa Gly His
        35

<210> SEQ ID NO 12
<211> LENGTH: 37
<212> TYPE: PRT
<213> ORGANISM: unknown
<220> FEATURE:
<223> OTHER INFORMATION: wherein the initial D is the active site
      Aspartic acid, the terminal H is the active site Histidine, and X
      is any amino acid
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
<223> OTHER INFORMATION: X is T, S or F or X is S or F
<220> FEATURE:
<221> NAME/KEY: MISC_FEATURE
<222> LOCATION: (13)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (26)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 12

Asp Thr Gly Ile Xaa Xaa Xaa His Xaa Asp Leu Xaa Xaa Xaa Xaa Xaa
1               5                   10                  15

Gly Gly Xaa Ser Val Phe Thr Asp Ser Xaa Xaa Xaa Xaa Xaa Xaa
            20                  25                  30

Asp Xaa Xaa Gly His
        35

<210> SEQ ID NO 13
<211> LENGTH: 37
<212> TYPE: PRT
<213> ORGANISM: unknown
<220> FEATURE:
<223> OTHER INFORMATION: wherein the initial D is the active site
      Aspartic acid, the terminal H is the active site Histidine, X is
      any amino acid, and Xb is S or R or Xb is S
<220> FEATURE:
<221> NAME/KEY: MISC_FEATURE
```

```
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (26)..(27)
<223> OTHER INFORMATION: X is any amino acid
<220> FEATURE:
<221> NAME/KEY: MISC_FEATURE
<222> LOCATION: (28)..(28)
<223> OTHER INFORMATION: X is S or R or X is S
<220> FEATURE:
<221> NAME/KEY: MISC_FEATURE
<222> LOCATION: (29)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 13

Asp Thr Gly Ile Xaa Xaa Xaa His Xaa Asp Leu Xaa Xaa Xaa Xaa
1               5                   10                  15

Gly Gly Xaa Ser Val Phe Thr Asp Ser Xaa Xaa Xaa Xaa Xaa Xaa
            20                  25                  30

Asp Xaa Xaa Gly His
        35

<210> SEQ ID NO 14
<211> LENGTH: 37
<212> TYPE: PRT
<213> ORGANISM: unknown
<220> FEATURE:
<223> OTHER INFORMATION: wherein the initial D is the active site
      Aspartic acid; the terminal H is the active site Histidine; X is
      any amino acid; Xa is T, S or F or Xa is S or F; and Xb is S or R
      or Xb is S
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: X is T, S or F or X is S or F
<220> FEATURE:
<221> NAME/KEY: MISC_FEATURE
<222> LOCATION: (13)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (26)..(27)
<223> OTHER INFORMATION: X is any amino acid
<220> FEATURE:
<221> NAME/KEY: MISC_FEATURE
<222> LOCATION: (28)..(28)
```

```
<223> OTHER INFORMATION: X is S or R or X is S
<220> FEATURE:
<221> NAME/KEY: MISC_FEATURE
<222> LOCATION: (29)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 14

Asp Thr Gly Ile Xaa Xaa Xaa His Xaa Asp Leu Xaa Xaa Xaa Xaa
1               5                   10                  15

Gly Gly Xaa Ser Val Phe Thr Asp Ser Xaa Xaa Xaa Xaa Xaa Xaa
            20                  25                  30

Asp Xaa Xaa Gly His
            35

<210> SEQ ID NO 15
<211> LENGTH: 37
<212> TYPE: PRT
<213> ORGANISM: unknown
<220> FEATURE:
<223> OTHER INFORMATION: wherein the initial D is the active site
      Aspartic acid and the terminal H is the active site Histidine, and
      X is any amino acid
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: X is any amino acid
<220> FEATURE:
<221> NAME/KEY: MISC_FEATURE
<222> LOCATION: (32)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 15

Asp Thr Gly Ile Xaa Xaa Xaa His Xaa Asp Leu Xaa Ala Asn Val Xaa
1               5                   10                  15

Gly Gly Xaa Ser Val Phe Thr Asp Ser Ala Asn Xaa Asp Pro Phe Xaa
            20                  25                  30

Asp Xaa Xaa Gly His
            35

<210> SEQ ID NO 16
<211> LENGTH: 13
<212> TYPE: PRT
<213> ORGANISM: unknown
```

```
<220> FEATURE:
<223> OTHER INFORMATION: wherein the initial D is the active site
      Aspartic acid, the terminal GGXS is in the outermost strand of the
      central beta sheet, and X is any amino acid;
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid

<400> SEQUENCE: 16

His Xaa Asp Leu Xaa Ala Asn Val Xaa Gly Gly Xaa Ser
1               5                   10

<210> SEQ ID NO 17
<211> LENGTH: 17
<212> TYPE: PRT
<213> ORGANISM: unknown
<220> FEATURE:
<223> OTHER INFORMATION: wherein the initial GGXS is in the outermost
      strand of the central beta sheet and X is any amino acid;
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid

<400> SEQUENCE: 17

Gly Gly Xaa Ser Val Phe Thr Asp Ser Ala Asn Xaa Asp Pro Phe Xaa
1               5                   10                  15
Asp

<210> SEQ ID NO 18
<211> LENGTH: 13
<212> TYPE: PRT
<213> ORGANISM: unknown
<220> FEATURE:
<223> OTHER INFORMATION: wherein the initial D is the active site
      Aspartic acid; the terminal GGXS is in the outermost strand of the
      central beta sheet; Xa is T, S or F or Xa is S or F; and X is any
      amino acid.
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: X is T, S or F or X is S or F
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
```

```
<223> OTHER INFORMATION: X is any amino acid

<400> SEQUENCE: 18

His Xaa Asp Leu Xaa Ala Asn Val Xaa Gly Gly Xaa Ser
1               5                   10

<210> SEQ ID NO 19
<211> LENGTH: 17
<212> TYPE: PRT
<213> ORGANISM: unknown
<220> FEATURE:
<223> OTHER INFORMATION: wherein the initial GGXS is in the outermost
      strand of the central beta sheet, X is any amino acid, and Xb is S
      or R or Xb is S;
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (12)..(12)
<223> OTHER INFORMATION: X is S or R or X is S
<220> FEATURE:
<221> NAME/KEY: MISC_FEATURE
<222> LOCATION: (16)..(16)
<223> OTHER INFORMATION: X is any amino acid

<400> SEQUENCE: 19

Gly Gly Xaa Ser Val Phe Thr Asp Ser Ala Asn Xaa Asp Pro Phe Xaa
1               5                   10                  15

Asp

<210> SEQ ID NO 20
<211> LENGTH: 37
<212> TYPE: PRT
<213> ORGANISM: unknown
<220> FEATURE:
<223> OTHER INFORMATION: wherein the initial D is the active site
      Aspartic acid; the terminal H is the active site Histidine; X is
      any amino acid; and Xa is S or F
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
<223> OTHER INFORMATION: Xa is S or F
<220> FEATURE:
<221> NAME/KEY: MISC_FEATURE
<222> LOCATION: (16)..(16)
<223> OTHER INFORMATION: Xa is any amino acid
<220> FEATURE:
<221> NAME/KEY: MISC_FEATURE
<222> LOCATION: (19)..(19)
<223> OTHER INFORMATION: Xa is any amino acid
<220> FEATURE:
<221> NAME/KEY: MISC_FEATURE
<222> LOCATION: (28)..(28)
<223> OTHER INFORMATION: Xa is any amino acid
<220> FEATURE:
<221> NAME/KEY: MISC_FEATURE
<222> LOCATION: (32)..(32)
<223> OTHER INFORMATION: Xa is any amino acid
<220> FEATURE:
<221> NAME/KEY: MISC_FEATURE
<222> LOCATION: (34)..(35)
<223> OTHER INFORMATION: Xa is any amino acid

<400> SEQUENCE: 20
```

```
Asp Thr Gly Ile Xaa Xaa Xaa His Xaa Asp Leu Xaa Ala Asn Val Xaa
1               5                   10                  15

Gly Gly Xaa Ser Val Phe Thr Asp Ser Ala Asn Xaa Asp Pro Phe Xaa
            20                  25                  30

Asp Xaa Xaa Gly His
        35
```

<210> SEQ ID NO 21
<211> LENGTH: 37
<212> TYPE: PRT
<213> ORGANISM: unknown
<220> FEATURE:
<223> OTHER INFORMATION: wherein the initial D is the active site
      Aspartic acid and the terminal H is the active site Histidine, X
      is any amino acid, and Xb is S
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (28)..(28)
<223> OTHER INFORMATION: X is S
<220> FEATURE:
<221> NAME/KEY: MISC_FEATURE
<222> LOCATION: (32)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 21

```
Asp Thr Gly Ile Xaa Xaa Xaa His Xaa Asp Leu Xaa Ala Asn Val Xaa
1               5                   10                  15

Gly Gly Xaa Ser Val Phe Thr Asp Ser Ala Asn Xaa Asp Pro Phe Xaa
            20                  25                  30

Asp Xaa Xaa Gly His
        35
```

<210> SEQ ID NO 22
<211> LENGTH: 37
<212> TYPE: PRT
<213> ORGANISM: unknown
<220> FEATURE:
<223> OTHER INFORMATION: wherein the initial D is the active site
      Aspartic acid and the terminal H is the active site Histidine, and
      X is any amino acid
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)

```
<223> OTHER INFORMATION: X is any amino acid
<220> FEATURE:
<221> NAME/KEY: MISC_FEATURE
<222> LOCATION: (12)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (23)..(23)
<223> OTHER INFORMATION: X is any amino acid
<220> FEATURE:
<221> NAME/KEY: MISC_FEATURE
<222> LOCATION: (25)..(32)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid

<400> SEQUENCE: 22

Asp Thr Gly Ile Xaa Xaa Xaa His Xaa Asp Leu Xaa Xaa Xaa Xaa
1               5                   10                  15

Gly Gly Xaa Ser Val Phe Xaa Asp Xaa Xaa Xaa Xaa Xaa Xaa Xaa
            20                  25                  30

Asp Xaa Xaa Gly His
        35

<210> SEQ ID NO 23
<211> LENGTH: 37
<212> TYPE: PRT
<213> ORGANISM: unknown
<220> FEATURE:
<223> OTHER INFORMATION: wherein the initial D is the active site
      Aspartic acid and the terminal H is the active site Histidine, and
      X is any amino acid
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (12)..(13)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid
<220> FEATURE:
<221> NAME/KEY: MISC_FEATURE
<222> LOCATION: (23)..(23)
<223> OTHER INFORMATION: X is any amino acid
<220> FEATURE:
<221> NAME/KEY: MISC_FEATURE
<222> LOCATION: (25)..(26)
<223> OTHER INFORMATION: X is any amino acid
<220> FEATURE:
<221> NAME/KEY: MISC_FEATURE
<222> LOCATION: (28)..(28)
<223> OTHER INFORMATION: X is any amino acid
<220> FEATURE:
<221> NAME/KEY: MISC_FEATURE
<222> LOCATION: (31)..(32)
<223> OTHER INFORMATION: X is any amino acid
<220> FEATURE:
```

```
<221> NAME/KEY: MISC_FEATURE
<222> LOCATION: (34)..(35)
<223> OTHER INFORMATION: X is any amino acid

<400> SEQUENCE: 23

Asp Thr Gly Ile Xaa Xaa Xaa His Xaa Asp Leu Xaa Xaa Asn Val Xaa
1               5                   10                  15

Gly Gly Xaa Ser Val Phe Xaa Asp Xaa Xaa Asn Xaa Asp Pro Xaa Xaa
            20                  25                  30

Asp Xaa Xaa Gly His
        35

<210> SEQ ID NO 24
<211> LENGTH: 281
<212> TYPE: PRT
<213> ORGANISM: unknown
<220> FEATURE:
<223> OTHER INFORMATION: Bacillus sp. 18N1

<400> SEQUENCE: 24

Ala Gln Thr Thr Pro Trp Gly Ile Pro Arg Val Gln Gly Thr Ala Ala
1               5                   10                  15

Gln Asn Ala Gly Tyr Thr Gly Asn Gly Val Lys Val Ala Ile Leu Asp
            20                  25                  30

Thr Gly Ile Asp Arg Asn His Pro Asp Leu Ser Ala Asn Val Lys Gly
        35                  40                  45

Gly His Ser Val Phe Thr Asp Ser Ala Asn Ser Asp Pro Phe Phe Asp
    50                  55                  60

Gly Asp Gly His Gly Thr His Val Ala Gly Thr Val Ala Ala Val Asn
65                  70                  75                  80

Asn Asp Ile Gly Val Ile Gly Val Ala Ser Glu Ala Ser Leu Tyr Ala
                85                  90                  95

Val Lys Val Leu Asn Asn Ala Gly Ser Gly Ser Tyr Ala Gly Ile Ala
            100                 105                 110

Glu Gly Ile Glu Trp Ala Ile Asn Asn Asp Ile Asp Ile Ile Asn Met
        115                 120                 125

Ser Leu Gly Gly Ser Gln Ser Ser Ala Ile Leu Lys Gln Phe Ser Asp
    130                 135                 140

Leu Ala Tyr Ala Glu Gly Leu Leu Val Ala Ala Ala Gly Asn Ser
145                 150                 155                 160

Gly Thr Arg Ser Gly Arg Asn Asp Thr Val Gly Tyr Pro Ala Lys Tyr
                165                 170                 175

Asp Ser Val Ile Ala Val Ala Ala Thr Asp Gln Asn Asn Gln Arg Ala
            180                 185                 190

Thr Phe Ser Ser Thr Gly Pro Ala Val Glu Ile Ser Ala Pro Gly Val
        195                 200                 205

Gly Ile Leu Ser Thr Thr Pro Asn Asn Asn Tyr Val Ser Phe Asn Gly
    210                 215                 220

Thr Ser Met Ala Ser Pro His Val Ala Gly Val Ala Ala Gln Val Trp
225                 230                 235                 240

Gln Ala Lys Pro His Leu Ser Asn Ile Glu Leu Arg Asn Leu Leu Asn
                245                 250                 255

Asp Thr Ala Ile Asp Leu Gly Ser Ser Thr Gln Tyr Gly Asn Gly Leu
            260                 265                 270

Val Gln Ser Leu Glu Ala Ile Gln Gln
        275                 280
```

```
<210> SEQ ID NO 25
<211> LENGTH: 281
<212> TYPE: PRT
<213> ORGANISM: unknown
<220> FEATURE:
<223> OTHER INFORMATION: Bacillus sp. WDG290

<400> SEQUENCE: 25

Gly Gln Thr Val Pro Trp Gly Ile Pro His Val Gln Gly Thr Ala Ala
1               5                   10                  15

Gln Asp Ala Gly Phe Thr Gly Ala Gly Leu Lys Val Ala Ile Leu Asp
            20                  25                  30

Thr Gly Ile Glu Ala Ser His Glu Asp Leu Ser Ala Asn Val Lys Gly
        35                  40                  45

Gly His Ser Val Phe Thr Asp Ser Ala Asn Ser Asp Pro Phe Tyr Asp
    50                  55                  60

Pro Asn Gly His Gly Thr His Val Ala Gly Thr Val Ala Ala Val Asp
65                  70                  75                  80

Asn Asp Leu Gly Val Ile Gly Val Ala Pro Glu Ala Asp Leu Tyr Ala
                85                  90                  95

Val Lys Val Leu Ser Asn Ala Gly Ser Gly Ser Ile Ala Gly Ile Ala
            100                 105                 110

Glu Gly Ile Glu Trp Ser Ile Asp Asn Gly Met Asp Ile Ile Asn Met
        115                 120                 125

Ser Leu Gly Ala Ser Gln Gly Ser Ser Ile Leu Glu Gln Phe Ser Asn
    130                 135                 140

Leu Ala Tyr Asp Glu Gly Leu Leu Val Val Ala Ala Gly Asn Ser
145                 150                 155                 160

Gly Asn Arg Gly Gly Asn Asn Asn Thr Val Gly Tyr Pro Ala Ala Tyr
                165                 170                 175

Asp Ser Val Ile Ala Val Ala Ala Val Asp Gln Asn Asn Asn Arg Ala
            180                 185                 190

Thr Phe Ser Ser Thr Gly Pro Ala Val Glu Ile Ser Ala Pro Gly Val
        195                 200                 205

Asn Val Leu Ser Thr Thr Pro Gly Asn Tyr Ala Ser Tyr Asn Gly
    210                 215                 220

Thr Ser Met Ala Ser Pro His Val Ala Gly Val Ala Ala Gln Val Trp
225                 230                 235                 240

Gln Ala Asn Pro Gly Leu Ser Asn Thr Glu Leu Arg Gln Leu Leu Asn
                245                 250                 255

Asp Thr Ala Val Asn Leu Gly Pro Ala His Gln Tyr Gly His Gly Leu
            260                 265                 270

Val Gln Ser Leu Asp Ala Ile Asn Gln
        275                 280

<210> SEQ ID NO 26
<211> LENGTH: 281
<212> TYPE: PRT
<213> ORGANISM: unknown
<220> FEATURE:
<223> OTHER INFORMATION: Bacillus sp. WDG291

<400> SEQUENCE: 26

Gly Gln Thr Val Pro Trp Gly Ile Pro His Val Gln Gly Thr Ala Ala
1               5                   10                  15

Gln Asp Ala Gly Tyr Thr Gly Ala Gly Leu Lys Val Ala Ile Leu Asp
            20                  25                  30
```

Thr Gly Ile Asp Arg Asn His Glu Asp Leu Phe Ala Asn Val Lys Gly
        35                  40                  45

Gly His Ser Val Phe Thr Asp Ser Ala Asn Ser Asp Pro Phe Tyr Asp
        50                  55                  60

Ala Asp Gly His Gly Thr His Val Ala Gly Thr Val Ala Ala Val Asp
65                  70                  75                  80

Asn Asp Leu Gly Val Val Gly Val Ala Ser Gln Ala Glu Leu Tyr Ala
                85                  90                  95

Val Lys Val Leu Asn Asn Ser Gly Ser Gly Ser Tyr Ala Gly Ile Ala
                100                 105                 110

Glu Gly Ile Glu Trp Ser Ile Asn Asn Gly Met Asp Ile Ile Asn Met
        115                 120                 125

Ser Leu Gly Gly Ser Gln Ser Ser Ile Leu Lys Gln Phe Ser Asp
        130                 135                 140

Leu Ala Tyr Glu Glu Gly Leu Leu Val Ala Ala Ala Gly Asn Ser
145                 150                 155                 160

Gly Asn Arg Gly Gly Asn Asn Asp Thr Val Gly Tyr Pro Ala Lys Tyr
                165                 170                 175

Asp Ser Val Ile Ala Val Ala Ala Val Asp Gln Asn Asn Asn Arg Ala
                180                 185                 190

Thr Phe Ser Ser Thr Gly Pro Ala Val Glu Ile Ser Ala Pro Gly Val
        195                 200                 205

Ser Ile Leu Ser Thr Thr Pro Gly Asn Asn Tyr Ala Ala Phe Asn Gly
        210                 215                 220

Thr Ser Met Ala Ser Pro His Val Ala Gly Val Ala Ala Gln Val Trp
225                 230                 235                 240

Gln Ala Lys Pro Glu Leu Ser Asn Val Glu Leu Arg Asn Leu Leu Asn
                245                 250                 255

Glu Thr Ala Val Asn Leu Gly Gly Ser Asn Gln Phe Gly His Gly Leu
                260                 265                 270

Val Gln Ser Leu Asp Ala Ile Gln His
        275                 280

<210> SEQ ID NO 27
<211> LENGTH: 281
<212> TYPE: PRT
<213> ORGANISM: unknown
<220> FEATURE:
<223> OTHER INFORMATION: Bacillus sp. LL01
<220> FEATURE:
<221> NAME/KEY: MISC_FEATURE
<222> LOCATION: (231)..(231)
<223> OTHER INFORMATION: X is any amino acid

<400> SEQUENCE: 27

Ala Gln Thr Thr Pro Trp Gly Ile Pro Arg Val Gln Gly Thr Ala Ala
1               5                   10                  15

Gln Asp Ala Gly Phe Thr Gly Asn Gly Val Lys Val Ala Ile Leu Asp
                20                  25                  30

Thr Gly Ile Asp Arg Asn His Pro Asp Leu Ser Ala Asn Val Lys Gly
        35                  40                  45

Gly His Ser Val Phe Thr Asp Ser Ala Asn Ser Asp Pro Phe Phe Asp
        50                  55                  60

Gly Asp Gly His Gly Thr His Val Ala Gly Thr Val Ala Ala Val Asn
65                  70                  75                  80

Asn Asp Ile Gly Val Ile Gly Val Ala Ser Glu Ala Ser Leu Tyr Ala

```
                        85                  90                  95
Val Lys Val Leu Asn Asn Ala Gly Ser Gly Ser Tyr Ala Gly Ile Ala
            100                 105                 110

Glu Gly Ile Glu Trp Ala Ile Asn Asn Asp Ile Asp Ile Ile Asn Met
            115                 120                 125

Ser Leu Gly Gly Ser Gln Ser Ser Ala Ile Leu Lys Glu Phe Ser Asp
            130                 135                 140

Leu Ala Tyr Ala Glu Gly Val Leu Val Val Ala Ala Ala Gly Asn Ser
145                 150                 155                 160

Gly Thr Arg Ser Gly Arg Asn Asp Thr Val Gly Tyr Pro Ala Lys Tyr
            165                 170                 175

Asp Ser Val Ile Ala Val Ala Thr Asp Gln Asn Asn Gln Arg Ala
            180                 185                 190

Thr Phe Ser Ser Thr Gly Pro Ala Val Glu Ile Ser Ala Pro Gly Val
            195                 200                 205

Gly Ile Leu Ser Thr Thr Pro Asn Asn Tyr Ala Ser Phe Asn Gly
            210                 215                 220

Thr Ser Met Ala Ser Pro Xaa Val Ala Gly Val Ala Ala Gln Val Trp
225                 230                 235                 240

Gln Ala Lys Pro His Leu Ser Asn Val Ala Leu Arg Asn Leu Leu Asn
            245                 250                 255

Glu Thr Ala Ile Asn Leu Gly Ser Ser Thr Gln Tyr Gly Asn Gly Leu
            260                 265                 270

Val Gln Ser Leu Asp Ala Ile Gln Gln
            275                 280

<210> SEQ ID NO 28
<211> LENGTH: 281
<212> TYPE: PRT
<213> ORGANISM: Bacillus pseudofirmus

<400> SEQUENCE: 28

Ala Gln Asn Val Pro Trp Gly Ile Pro Arg Val Gln Gly Thr Asp Ala
1               5                   10                  15

Gln Asn Ala Gly Tyr Thr Gly Asn Gly Val Lys Val Ala Ile Leu Asp
            20                  25                  30

Thr Gly Ile Asp Arg Ser His Pro Asp Leu Thr Ala Asn Val Gln Gly
            35                  40                  45

Gly His Ser Val Phe Thr Asp Ser Ala Asn Arg Asp Pro Phe Phe Asp
            50                  55                  60

Gly Asp Gly His Gly Thr His Val Ala Gly Thr Val Ala Ala Val Asn
65                  70                  75                  80

Asn Asp Ile Gly Val Val Gly Val Ala Ser Glu Ala Asp Leu Tyr Ala
            85                  90                  95

Val Lys Val Leu Asn Asn Ala Gly Ser Gly Ser Tyr Ala Gly Ile Ala
            100                 105                 110

Glu Gly Ile Glu Trp Ser Ile Asn Asn Gly Met Asp Ile Ile Asn Met
            115                 120                 125

Ser Leu Gly Gly Ser Gln Ser Ser Ala Ile Leu Lys Glu Phe Ser Asp
            130                 135                 140

Leu Ala Tyr Ala Glu Gly Leu Leu Val Val Ala Ala Ala Gly Asn Ser
145                 150                 155                 160

Gly Asn Arg Gly Gly Asn Asn Asp Thr Val Gly Tyr Pro Ala Lys Tyr
            165                 170                 175
```

```
Glu Ser Val Ile Ala Val Ala Ala Thr Asp Gln Asn Asn Gln Arg Ala
                180                 185                 190

Thr Phe Ser Ser Thr Gly Pro Ala Val Glu Ile Ser Ala Pro Gly Ala
            195                 200                 205

Gly Ile Leu Ser Thr Thr Pro Asn Asn Asn Tyr Ala Ser Phe Asn Gly
        210                 215                 220

Thr Ser Met Ala Ser Pro His Val Ala Gly Val Ala Ala Gln Val Trp
225                 230                 235                 240

Gln Ala Lys Pro His Leu Ser Asn Val Glu Leu Arg Asn Leu Leu Asn
                245                 250                 255

Asp Thr Ala Leu Pro Leu Gly Gly Ser Asn Gln Phe Gly Asn Gly Leu
            260                 265                 270

Val Gln Ser Met Ala Ala Ile Gln Gln
        275                 280

<210> SEQ ID NO 29
<211> LENGTH: 281
<212> TYPE: PRT
<213> ORGANISM: Bacillus marmarensis

<400> SEQUENCE: 29

Ala Gln Asn Val Pro Trp Gly Ile Pro Arg Val Gln Gly Thr Asp Ala
1               5                   10                  15

Gln Asn Ala Gly Tyr Thr Gly Asn Gly Val Lys Val Ala Ile Leu Asp
                20                  25                  30

Thr Gly Ile Asp Arg Ser His Pro Asp Leu Thr Ala Asn Val Gln Gly
            35                  40                  45

Gly His Ser Val Phe Thr Asp Ser Ala Asn Arg Asp Pro Phe Phe Asp
        50                  55                  60

Gly Asp Gly His Gly Thr His Val Ala Gly Thr Val Ala Ala Val Asn
65                  70                  75                  80

Asn Asp Ile Gly Val Val Gly Val Ala Ser Glu Ala Asp Leu Tyr Ala
                85                  90                  95

Val Lys Val Leu Asn Asn Ala Gly Ser Gly Ser Tyr Ala Gly Ile Ala
            100                 105                 110

Glu Gly Ile Glu Trp Ser Ile Asn Asn Gly Met Asp Ile Ile Asn Met
        115                 120                 125

Ser Leu Gly Gly Ser Gln Ser Ser Ala Ile Leu Lys Glu Phe Ser Asp
        130                 135                 140

Leu Ala Tyr Ala Glu Gly Leu Leu Val Ala Ala Ala Gly Asn Ser
145                 150                 155                 160

Gly Asn Arg Gly Gly Asn Asn Asp Thr Val Gly Tyr Pro Ala Lys Tyr
                165                 170                 175

Glu Ser Val Ile Ala Val Ala Ala Thr Asp Gln Asn Asn Gln Arg Ala
            180                 185                 190

Thr Phe Ser Ser Thr Gly Pro Ala Val Glu Ile Ser Ala Pro Gly Ala
        195                 200                 205

Gly Ile Leu Ser Thr Thr Pro Asn Asn Thr Tyr Ala Ser Phe Asp Gly
        210                 215                 220

Thr Ser Met Ala Ser Pro His Val Ala Gly Val Ala Ala Gln Val Trp
225                 230                 235                 240

Gln Ala Lys Pro His Leu Ser Asn Val Glu Leu Arg Asn Leu Leu Asn
                245                 250                 255

Asp Thr Ala Leu Pro Leu Gly Gly Ser Asn Gln Phe Gly Asn Gly Leu
            260                 265                 270
```

```
Val Gln Ser Met Ala Ala Ile Gln Gln
        275                 280
```

<210> SEQ ID NO 30
<211> LENGTH: 285
<212> TYPE: PRT
<213> ORGANISM: Alkaliphilus transvaalensis

<400> SEQUENCE: 30

```
Ser Gln Thr Val Pro Trp Gly Ile Ser His Val Gln Ala Ile Thr Ala
1               5                   10                  15

His Asn Ser Gly Tyr Thr Gly Glu Asn Val Lys Val Ala Ile Leu Asp
            20                  25                  30

Thr Gly Ile Asp Asn Lys His Glu Asp Leu Phe Ser Asn Val Lys Gly
        35                  40                  45

Gly Tyr Ser Val Phe Thr Asp Ser Ala Asn Ser Asp Pro Phe Tyr Asp
    50                  55                  60

Gly Asn Gly His Gly Thr His Val Ala Gly Thr Val Ala Ala Leu Asp
65                  70                  75                  80

Asn Asn Leu Gly Val Ile Gly Val Ala Tyr Asn Ala Asp Leu Tyr Ala
                85                  90                  95

Val Lys Val Leu Asn Asn Ser Gly Ser Gly Ser Tyr Asp Gly Ile Ala
            100                 105                 110

Gln Gly Ile Glu Trp Ala Val Asn Asn Gly Met Asp Ile Ile Asn Met
        115                 120                 125

Ser Leu Gly Gly Ser Ala Ser Ser Ala Ile Leu Glu Asn Met Val Asn
    130                 135                 140

Ala Ala Asn Asn Ala Gly Val Leu Leu Ile Ala Ala Gly Asn Ser
145                 150                 155                 160

Gly Asn Ile Phe Gly Trp Gly Asp Thr Val Gly Tyr Pro Ala Lys Tyr
                165                 170                 175

Gly Ser Val Met Ala Val Ala Ala Ile Asp Ser Asn Asn Arg Arg Ala
            180                 185                 190

Asn Phe Ser Ser His Gly Pro Ala Val Glu Ile Ser Ala Pro Gly Val
        195                 200                 205

Ser Val Leu Ser Thr Thr Pro Gly Asn Asn Tyr Ala Ser Phe Asn Gly
    210                 215                 220

Thr Ser Met Ala Ser Pro His Val Ala Gly Val Ala Ala Leu Ile Lys
225                 230                 235                 240

Gly Ala Asn Pro Thr Leu Thr Asn Ser Gln Ile Arg Gln Ile Met Asn
                245                 250                 255

Asp Thr Ala Leu Asn Leu Gly Thr Trp Asn Tyr Tyr Gly Asn Gly Leu
            260                 265                 270

Val Arg Ala Met Asn Gly Ile Asn Leu Ala Leu Thr Tyr
        275                 280                 285
```

<210> SEQ ID NO 31
<211> LENGTH: 281
<212> TYPE: PRT
<213> ORGANISM: Bacillus aurantiacus

<400> SEQUENCE: 31

```
Gly Gln Thr Val Pro Trp Gly Ile Pro His Val Gln Gly Thr Ala Ala
1               5                   10                  15

Gln Asp Ala Gly Tyr Thr Gly Ala Gly Leu Lys Val Ala Ile Leu Asp
            20                  25                  30
```

```
Thr Gly Ile Asp Arg Asn His Glu Asp Leu Phe Glu Asn Val Lys Gly
            35                  40                  45

Gly His Ser Val Phe Thr Asp Ala Ala Asn Arg Asp Pro Phe Tyr Asp
 50                  55                  60

Ala Asp Gly His Gly Thr His Val Ala Gly Thr Val Ala Ala Val Asp
 65                  70                  75                  80

Asn Asp Leu Gly Val Val Gly Val Ala Ser Gln Ala Glu Leu Tyr Ala
                 85                  90                  95

Val Lys Val Leu Asn Asn Ser Gly Ser Gly Ser Tyr Ala Gly Ile Ala
                100                 105                 110

Glu Gly Ile Glu Trp Ser Ile Asn Asn Gly Met Asp Ile Ile Asn Met
            115                 120                 125

Ser Leu Gly Gly Ser Gln Ser Ser Ser Ile Leu Lys Gln Phe Ser Asp
130                 135                 140

Leu Ala Tyr Glu Glu Gly Leu Leu Val Ala Ala Ala Gly Asn Ser
145                 150                 155                 160

Gly Asn Arg Gly Gly Asn Asn Asp Thr Val Gly Tyr Pro Ala Lys Tyr
                165                 170                 175

Asp Ser Val Ile Ala Val Ala Ala Val Asp Gln Asn Asn Asn Arg Ala
                180                 185                 190

Thr Phe Ser Ser Thr Gly Pro Ala Val Glu Ile Ser Ala Pro Gly Val
            195                 200                 205

Ser Ile Leu Ser Thr Thr Pro Gly Asn Asn Tyr Ala Ala Phe Asn Gly
210                 215                 220

Thr Ser Met Ala Ser Pro His Val Ala Gly Val Ala Ala Gln Val Trp
225                 230                 235                 240

Gln Ala Lys Pro Glu Leu Ser Asn Val Glu Leu Arg Asn Leu Leu Asn
                245                 250                 255

Glu Thr Ala Val Asn Leu Gly Arg Ser Asn Gln Phe Gly His Gly Leu
                260                 265                 270

Val Gln Ser Leu Asp Ala Ile Gln Gln
                275                 280

<210> SEQ ID NO 32
<211> LENGTH: 281
<212> TYPE: PRT
<213> ORGANISM: Halalkalibacillus halophilus

<400> SEQUENCE: 32

Asn Gln Thr Thr Pro Tyr Gly Ile Asp Gln Val Gln Ala Thr Glu Ala
 1               5                  10                  15

Gln Asn Gln Gly His Thr Gly Glu Gly Val Asp Val Ala Val Leu Asp
                 20                  25                  30

Thr Gly Ile Asp Ala Ser His Glu Asp Leu Ala Ala Asn Val Gln Gly
            35                  40                  45

Gly His Ser Val Phe Asp Asp Ala Glu Asn Ser Asp Pro Tyr Asn Asp
 50                  55                  60

Gly Asp Gly His Gly Thr His Val Ala Gly Thr Val Ala Ala Ala Asn
 65                  70                  75                  80

Asn Asp Thr Gly Val Val Gly Val Ala Pro Gln Ala Asn Leu Tyr Ala
                 85                  90                  95

Val Lys Val Leu Gly Asn Asp Gly Ser Gly Ser Tyr Ala Gly Ile Ala
                100                 105                 110

Glu Gly Ile Glu Trp Ser Ile Asn Asn Gly Met Asp Val Val Asn Met
```

```
            115                 120                 125
Ser Leu Gly Gly Pro Thr Ser Ser Pro Ile Leu Glu Glu Phe Ala Asp
    130                 135                 140

Leu Ala Asn Glu Glu Gly Leu Leu Val Val Ala Ala Gly Asn Ser
145                 150                 155                 160

Gly Ser Ser Leu Gly Trp Phe Asp Thr Val Asn Tyr Pro Ala Lys Tyr
                165                 170                 175

Asp Ser Val Met Ala Val Gly Ala Val Asp Glu Asn Asn Asn Arg Pro
                180                 185                 190

Ser Phe Ser Ser Thr Gly Pro Ala Val Glu Ile Ala Ala Pro Gly Val
                195                 200                 205

Asp Thr Leu Ser Thr Val Pro Gly Asn Asp Tyr Ala Ser Leu Ser Gly
                210                 215                 220

Thr Ser Met Ala Ser Pro His Val Ala Gly Val Ala Ala Ser Val Trp
225                 230                 235                 240

Ala Glu Lys Ser Asp Leu Ser Asn Asp Glu Leu Arg Gln Leu Leu Lys
                245                 250                 255

Asp Thr Ala Val Asp Leu Gly Asn Glu Asp His Tyr Gly Ala Gly Leu
                260                 265                 270

Val Gln Val Leu Asp Ala Leu Asn Gln
                275                 280

<210> SEQ ID NO 33
<211> LENGTH: 281
<212> TYPE: PRT
<213> ORGANISM: Bacillus akibai

<400> SEQUENCE: 33

Ala Glu Ser Val Pro Trp Gly Val Pro His Val Gln Gly Thr Thr Ala
1               5                   10                  15

Gln Ala Asn Gly Phe Thr Gly Ser Gly Val Lys Val Ala Ile Leu Asp
                20                  25                  30

Thr Gly Ile Asp Leu Ser His Glu Asp Leu Ser Ala Asn Val Lys Gly
                35                  40                  45

Gly Phe Ser Val Phe Asp Asp Ala Ala Asn Arg Asp Pro Tyr Tyr Asp
            50                  55                  60

Ala Asn Gly His Gly Thr His Val Ala Gly Thr Val Ala Ala Val Asn
65                  70                  75                  80

Asn Asn Leu Gly Val Leu Gly Val Ala Tyr Gln Ala Asp Leu Tyr Ala
                85                  90                  95

Val Lys Val Leu Asn Asn Asp Gly Ser Gly Ser Tyr Ala Gly Ile Ala
                100                 105                 110

Arg Gly Ile Glu Trp Ser Val Gln Asn Gly Met Asp Ile Val Asn Met
                115                 120                 125

Ser Leu Gly Gly Ser Thr Ser Ser Ser Ile Leu Lys Glu Trp Ser Asp
    130                 135                 140

Leu Ala Tyr Ala Gln Gly Val Leu Leu Val Ala Ala Gly Asn Ser
145                 150                 155                 160

Gly Thr Arg Pro Gly Arg Gly Asp Asn Val Gly Tyr Pro Ala Lys Tyr
                165                 170                 175

Asp Ser Val Ile Ala Val Ala Ala Val Asp Gln Asn Asn Asn Arg Ala
                180                 185                 190

Thr Phe Ser Ser Thr Gly Pro Ala Val Glu Ile Ser Ala Pro Gly Val
                195                 200                 205
```

```
Ser Ile Leu Ser Thr Ile Pro Asn Asn Gly Tyr Ala Ser Tyr Asn Gly
    210                 215                 220

Thr Ser Met Ala Ser Pro His Val Ala Gly Val Ala Ala Leu Leu Leu
225                 230                 235                 240

Glu Asn Asn Ser Asn Leu Thr Asn Thr Glu Leu Arg Glu Leu Leu Gln
                245                 250                 255

Ser Ser Ala Lys Ser Leu Gly Thr Ala Ser Gln Tyr Gly Tyr Gly Leu
            260                 265                 270

Val Gln Ala Met Asp Ala Ile Asn Gln
            275                 280

<210> SEQ ID NO 34
<211> LENGTH: 307
<212> TYPE: PRT
<213> ORGANISM: unknown
<220> FEATURE:
<223> OTHER INFORMATION: Bacillus sp. KSM-LD1

<400> SEQUENCE: 34

Ala Gln Thr Val Pro Trp Gly Val Pro His Val Gln Gly Thr Asp Ala
1               5                   10                  15

His Ala Ala Gly His Thr Gly Ser Gly Val Lys Val Ala Ile Leu Asp
            20                  25                  30

Thr Gly Ile Asp Arg Asn His Glu Asp Leu Asn Val Arg Gly Gly His
        35                  40                  45

Ser Val Phe Thr Asp Ser Ala Asn Arg Asp Pro Tyr Tyr Asp Gly Ser
    50                  55                  60

Gly His Gly Thr His Val Ala Gly Thr Val Ala Ala Leu Asn Asn Ser
65                  70                  75                  80

Val Gly Val Leu Gly Val Ala Tyr Asn Ala Glu Leu Tyr Ala Val Lys
                85                  90                  95

Val Leu Asn Asn Ser Gly Ser Gly Ser Tyr Ala Gly Ile Ala Glu Gly
            100                 105                 110

Ile Glu Trp Ala Val Asn Asn Gly Met Asp Ile Ile Asn Met Ser Leu
        115                 120                 125

Gly Gly Ser Met Ser Ser Ile Leu Glu Glu Trp Cys Asn Ile Ala
    130                 135                 140

Tyr Asn Ser Gly Val Leu Val Val Ala Ala Gly Asn Ser Gly Arg
145                 150                 155                 160

Thr Asn Gly Arg Gly Asp Thr Val Gly Tyr Pro Ala Lys Tyr Asp Ser
                165                 170                 175

Val Ile Ala Val Ala Ala Val Asp Ser Asn Asn Arg Ala Ser Phe
            180                 185                 190

Ser Ser Thr Gly Pro Ala Val Glu Ile Ala Ala Pro Gly Val Asn Ile
        195                 200                 205

Leu Ser Thr Thr Pro Gly Asn Ser Tyr Ala Ser Tyr Asn Gly Thr Ser
    210                 215                 220

Met Ala Ser Pro His Val Ala Gly Val Ala Ala Leu Val Leu Ala Ala
225                 230                 235                 240

Asn Pro Asn Leu Ser Asn Val Glu Leu Arg Asn Arg Leu Asn Asp Thr
                245                 250                 255

Ala Gln Asn Leu Gly Asp Ala Asn His Phe Gly Asn Gly Leu Val Arg
            260                 265                 270

Ala Val Asp Ala Ile Asn Gly Thr Ser Ser Gly Asp Asn Gly Gly
        275                 280                 285
```

```
Asp Asp Gly Gly Ser Glu Pro Thr Lys Pro Gly Asn Gly Lys Gly Asn
    290                 295                 300

Gly Arg Asn
305

<210> SEQ ID NO 35
<211> LENGTH: 275
<212> TYPE: PRT
<213> ORGANISM: Halalkalibacillus halophilus

<400> SEQUENCE: 35

Ala Gln Gln Thr Pro Trp Gly Ile Pro Arg Val Glu Gly Thr Thr Ser
1               5                   10                  15

Gln Asn Asn Gly Tyr Thr Gly Asp Gly Ile Asp Val Ala Val Leu Asp
            20                  25                  30

Thr Gly Ile Asp Arg Ser His Val Asp Leu Asn Val Ser Gly Gly Tyr
        35                  40                  45

Ser Val Phe Gly Asp Ser Pro Tyr Tyr Asp Gly Asp Gly His Gly Thr
    50                  55                  60

His Val Ala Gly Thr Ile Ala Ala Leu Asp Asn Asn Thr Gly Val Leu
65                  70                  75                  80

Gly Val Ala Pro Asp Ala Asn Leu Tyr Ala Val Lys Val Leu Asp Asn
                85                  90                  95

Asn Gly Ser Gly Ser Tyr Ser Gly Ile Ala Gln Gly Ile Glu Trp Ser
            100                 105                 110

Ile Ile Asn Gly Met Asp Ile Ile Asn Met Ser Leu Gly Gly Pro Ser
        115                 120                 125

Ser Ser Ser Ile Leu Gln Gln Tyr Ser Asp Leu Ala Tyr Asn Asn Gly
    130                 135                 140

Ile Leu Val Val Ala Ala Gly Asn Ser Gly Asn Ser Trp Gly Trp
145                 150                 155                 160

Gly Asp Thr Val Gly Tyr Pro Ala Lys Tyr Asp Ser Val Ile Ala Val
                165                 170                 175

Gly Ala Val Asp Gln Asn Asn Asn Arg Ala Ser Phe Ser Ser His Gly
            180                 185                 190

Pro Ala Val Glu Leu Ala Ala Pro Gly Val Gly Val Leu Ser Thr Val
        195                 200                 205

Pro Gly Asn Gly Tyr Ser Ser Leu Asn Gly Thr Ser Met Ala Ser Pro
    210                 215                 220

His Val Ala Gly Val Ala Ala Gln Val Trp Glu Ala Lys Pro His Leu
225                 230                 235                 240

Ser Asn Val Gln Leu Arg Ser Leu Leu Gln Gln Thr Ala Gln Asn Leu
                245                 250                 255

Gly Asn Ser Asn Tyr Tyr Gly Ser Gly Leu Val Lys Ser Tyr Gln Ala
            260                 265                 270

Ile Thr His
        275

<210> SEQ ID NO 36
<211> LENGTH: 275
<212> TYPE: PRT
<213> ORGANISM: Bacillus amyloliquefaciens

<400> SEQUENCE: 36

Ala Gln Ser Val Pro Tyr Gly Val Ser Gln Ile Lys Ala Pro Ala Leu
1               5                   10                  15
```

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 37
<211> LENGTH: 275
<212> TYPE: PRT
<213> ORGANISM: Geobacillus stearothermophilus

<400> SEQUENCE: 37

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

```
Trp Ala Ile Ala Tyr Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Ile Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
                180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
        275

<210> SEQ ID NO 38
<211> LENGTH: 275
<212> TYPE: PRT
<213> ORGANISM: Bacillus subtilis

<400> SEQUENCE: 38

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Asp Lys Ala Val Ala
        130                 135                 140

Ser Gly Ile Val Val Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
```

```
              195                 200                 205
Leu Pro Gly Gly Thr Tyr Gly Ser Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Ser Asn Ala Gln Val Arg Asp Arg Leu Glu Ser Thr Ala Thr Asn
                245                 250                 255

Leu Gly Ser Ser Phe Tyr Tyr Gly Lys Gly Leu Ile Asn Val Gln Ala
                260                 265                 270

Ala Ala Gln
        275

<210> SEQ ID NO 39
<211> LENGTH: 275
<212> TYPE: PRT
<213> ORGANISM: Bacillus pumilus

<400> SEQUENCE: 39

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Ala Ser Gly Ser Thr Ala Leu Lys Asn Ala Val Asp Thr Ala Asn Asn
        130                 135                 140

Arg Gly Val Val Val Ala Ala Ala Gly Asn Ser Gly Ser Ser Gly
145                 150                 155                 160

Ser Arg Ser Thr Val Gly Tyr Pro Ala Lys Tyr Glu Ser Thr Ile Ala
                165                 170                 175

Val Ala Asn Val Asn Ser Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
        210                 215                 220

Pro His Val Ala Gly Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
                260                 265                 270

Ala Ser Asn
        275
```

```
<210> SEQ ID NO 40
<211> LENGTH: 274
<212> TYPE: PRT
<213> ORGANISM: Bacillus licheniformis

<400> SEQUENCE: 40

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 41
<211> LENGTH: 274
<212> TYPE: PRT
<213> ORGANISM: Bacillus sonorensis

<400> SEQUENCE: 41

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Ser Ser His Thr Asp Leu Lys Val Val Gly Gly Ala
        35                  40                  45

Ser Phe Val Ser Gly Glu Ser Tyr Asn Thr Asp Gly Asn Gly His Gly
```

```
                        50                  55                  60
Thr His Val Ala Gly Thr Val Ala Ala Leu Asp Asn Thr Thr Gly Val
 65                  70                  75                  80

Leu Gly Val Ala Pro Asn Val Ser Leu Tyr Ala Ile Lys Val Leu Asn
                 85                  90                  95

Ser Ser Gly Ser Gly Thr Tyr Ser Ala Ile Val Ser Gly Ile Glu Trp
                100                 105                 110

Ala Thr Gln Asn Gly Leu Asp Val Ile Asn Met Ser Leu Gly Gly Pro
                115                 120                 125

Ser Gly Ser Thr Ala Leu Lys Gln Ala Val Asp Lys Ala Tyr Ala Ser
            130                 135                 140

Gly Ile Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
                180                 185                 190

Ser Glu Leu Glu Val Met Ala Pro Gly Val Ser Val Tyr Ser Thr Tyr
            195                 200                 205

Pro Ser Asn Thr Tyr Thr Ser Leu Asn Gly Thr Ser Met Ala Ser Pro
210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
                245                 250                 255

Gly Asp Ser Phe Tyr Tyr Gly Lys Gly Leu Ile Asn Val Glu Ala Ala
                260                 265                 270

Ala Gln

<210> SEQ ID NO 42
<211> LENGTH: 269
<212> TYPE: PRT
<213> ORGANISM: Bacillus lentus

<400> SEQUENCE: 42

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
```

```
145                 150                 155                 160
Tyr Pro Ala Arg Tyr Ala Asn Ala Met Ala Val Gly Ala Thr Asp Gln
            165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
            195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
            245                 250                 255
Tyr Gly Ser Gly Leu Val Asn Ala Glu Ala Ala Thr Arg
            260                 265

<210> SEQ ID NO 43
<211> LENGTH: 275
<212> TYPE: PRT
<213> ORGANISM: unknown
<220> FEATURE:
<223> OTHER INFORMATION: Bacillus sp. KSM-LD1

<400> SEQUENCE: 43

Ala Gln Thr Thr Pro Trp Gly Val Thr His Ile Asn Ala His Arg Ala
1               5                   10                  15
His Ser Ser Gly Val Thr Gly Ser Gly Val Lys Val Ala Ile Leu Asp
            20                  25                  30
Thr Gly Ile His Ala Ser His Pro Asp Leu Asn Val Arg Gly Gly Ala
            35                  40                  45
Ser Phe Ile Ser Gly Glu Ser Asn Pro Tyr Ile Asp Ser Asn Gly His
    50                  55                  60
Gly Thr His Val Ala Gly Thr Val Ala Ala Leu Asn Asn Thr Val Gly
65                  70                  75                  80
Val Leu Gly Val Ala Tyr Asn Ala Glu Leu Tyr Ala Val Lys Val Leu
                85                  90                  95
Ser Ala Ser Gly Ser Gly Thr Leu Ser Gly Ile Ala Gln Gly Val Glu
            100                 105                 110
Trp Ser Ile Ala Asn Lys Met Asp Val Ile Asn Met Ser Leu Gly Gly
            115                 120                 125
Ser Ser Gly Ser Thr Ala Leu Gln Arg Ala Val Asp Asn Ala Tyr Arg
    130                 135                 140
Asn Asn Ile Val Val Ala Ala Ala Gly Asn Ser Gly Ala Gln Gly
145                 150                 155                 160
Asn Arg Asn Thr Ile Gly Tyr Pro Ala Arg Tyr Ser Ser Val Ile Ala
            165                 170                 175
Val Gly Ala Val Asp Ser Asn Asn Asn Arg Ala Ser Phe Ser Ser Val
            180                 185                 190
Gly Ser Glu Leu Glu Val Met Ala Pro Gly Val Ser Ile Leu Ser Thr
            195                 200                 205
Val Pro Gly Ser Ser Tyr Ala Ser Tyr Asn Gly Thr Ser Met Ala Ser
    210                 215                 220
Pro His Val Ala Gly Ala Ala Ala Leu Leu Lys Ala Lys Tyr Pro Asn
225                 230                 235                 240
Trp Ser Ala Ala Gln Ile Arg Asn Lys Leu Asn Ser Thr Thr Thr Tyr
```

```
                       245                 250                 255
Leu Gly Ser Ser Phe Tyr Tyr Gly Asn Gly Val Ile Asn Val Glu Arg
            260                 265                 270

Ala Leu Gln
        275

<210> SEQ ID NO 44
<211> LENGTH: 276
<212> TYPE: PRT
<213> ORGANISM: unknown
<220> FEATURE:
<223> OTHER INFORMATION: Bacillus sp. Strain LG12

<400> SEQUENCE: 44

Ala Gln Thr Val Pro Tyr Gly Val Pro His Ile Lys Ala Asp Val Ala
1               5                   10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Val Gly Gly Ala
        35                  40                  45

Ser Phe Val Ser Glu Glu Pro Asp Ala Leu Thr Asp Gly Asn Gly His
50                  55                  60

Gly Thr His Val Ala Gly Thr Ile Ala Ala Leu Asn Asn Val Gly
65                  70                  75                  80

Val Leu Gly Val Ser Tyr Asp Val Asp Leu Tyr Ala Val Lys Val Leu
                85                  90                  95

Ser Ala Gly Gly Ser Gly Thr Leu Ala Gly Ile Ala Gln Gly Ile Glu
            100                 105                 110

Trp Ala Ile Asp Asn Asn Met Asp Val Ile Asn Met Ser Leu Gly Gly
        115                 120                 125

Ser Thr Gly Ser Thr Thr Leu Lys Gln Ala Ser Asp Asn Ala Tyr Asn
130                 135                 140

Ser Gly Ile Val Val Ile Ala Ala Ala Gly Asn Ser Gly Ser Val Leu
145                 150                 155                 160

Gly Leu Val Asn Thr Ile Gly Tyr Pro Ala Arg Tyr Asp Ser Val Ile
                165                 170                 175

Ala Val Gly Ala Val Asp Ser Asn Asn Asn Arg Ala Ser Phe Ser Ser
            180                 185                 190

Val Gly Ser Gln Leu Glu Val Met Ala Pro Gly Val Ala Ile Asn Ser
        195                 200                 205

Thr Leu Pro Gly Asn Gln Tyr Gly Glu Leu Asn Gly Thr Ser Met Ala
    210                 215                 220

Ser Pro His Val Ala Gly Ala Ala Ala Leu Leu Leu Ala Gln Asn Pro
225                 230                 235                 240

Asn Leu Thr Asn Val Gln Val Arg Glu Arg Leu Arg Asp Thr Ala Thr
                245                 250                 255

Asn Leu Gly Ser Ala Phe Asn Tyr Gly His Gly Val Ile Asn Leu Glu
            260                 265                 270

Arg Ala Leu Gln
        275

<210> SEQ ID NO 45
<211> LENGTH: 275
<212> TYPE: PRT
<213> ORGANISM: unknown
<220> FEATURE:
<223> OTHER INFORMATION: Bacillus sp. Strain LG12
```

<400> SEQUENCE: 45

```
Ala Gln Thr Val Pro Trp Gly Ile Pro His Ile Lys Ala Asp Lys Ala
1               5                  10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
    130                 135                 140

Arg Gly Ile Val Ile Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
        275
```

<210> SEQ ID NO 46
<211> LENGTH: 269
<212> TYPE: PRT
<213> ORGANISM: unknown
<220> FEATURE:
<223> OTHER INFORMATION: Bacillus sp. G-825-6

<400> SEQUENCE: 46

```
Asn Gln Val Thr Pro Trp Gly Ile Thr Arg Val Gln Ala Pro Thr Ala
1               5                  10                  15

Trp Thr Arg Gly Tyr Thr Gly Thr Gly Val Arg Val Ala Val Leu Asp
            20                  25                  30

Thr Gly Ile Ser Thr His Pro Asp Leu Asn Ile Arg Gly Gly Val Ser
        35                  40                  45

Phe Val Pro Gly Glu Pro Ser Tyr Gln Asp Gly Asn Gly His Gly Thr
    50                  55                  60
```

His Val Ala Gly Thr Ile Ala Ala Leu Asn Ser Ile Gly Val Val
65                  70                  75                  80

Gly Val Ala Pro Asn Ala Glu Leu Tyr Ala Val Lys Val Leu Gly Ala
            85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
            260                 265

<210> SEQ ID NO 47
<211> LENGTH: 281
<212> TYPE: PRT
<213> ORGANISM: artificial sequence
<220> FEATURE:
<223> OTHER INFORMATION: Consensus
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (14)..(15)
<223> OTHER INFORMATION: X is any amino acid
<220> FEATURE:
<221> NAME/KEY: MISC_FEATURE
<222> LOCATION: (18)..(19)
<223> OTHER INFORMATION: X is any amino acid
<220> FEATURE:
<221> NAME/KEY: MISC_FEATURE
<222> LOCATION: (24)..(24)
<223> OTHER INFORMATION: X is any amino acid
<220> FEATURE:
<221> NAME/KEY: MISC_FEATURE
<222> LOCATION: (37)..(37)
<223> OTHER INFORMATION: X is any amino acid
<220> FEATURE:
<221> NAME/KEY: MISC_FEATURE
<222> LOCATION: (43)..(45)
<223> OTHER INFORMATION: X is any amino acid
<220> FEATURE:
<221> NAME/KEY: MISC_FEATURE
<222> LOCATION: (47)..(47)
<223> OTHER INFORMATION: X is any amino acid
<220> FEATURE:
<221> NAME/KEY: MISC_FEATURE
<222> LOCATION: (50)..(50)
<223> OTHER INFORMATION: X is any amino acid
<220> FEATURE:

```
<221> NAME/KEY: MISC_FEATURE
<222> LOCATION: (54)..(54)
<223> OTHER INFORMATION: X is any amino acid
<220> FEATURE:
<221> NAME/KEY: MISC_FEATURE
<222> LOCATION: (56)..(57)
<223> OTHER INFORMATION: X is any amino acid
<220> FEATURE:
<221> NAME/KEY: MISC_FEATURE
<222> LOCATION: (59)..(60)
<223> OTHER INFORMATION: X is any amino acid
<220> FEATURE:
<221> NAME/KEY: MISC_FEATURE
<222> LOCATION: (62)..(63)
<223> OTHER INFORMATION: X is any amino acid
<220> FEATURE:
<221> NAME/KEY: MISC_FEATURE
<222> LOCATION: (82)..(83)
<223> OTHER INFORMATION: X is any amino acid
<220> FEATURE:
<221> NAME/KEY: MISC_FEATURE
<222> LOCATION: (90)..(91)
<223> OTHER INFORMATION: X is any amino acid
<220> FEATURE:
<221> NAME/KEY: MISC_FEATURE
<222> LOCATION: (93)..(93)
<223> OTHER INFORMATION: X is any amino acid
<220> FEATURE:
<221> NAME/KEY: MISC_FEATURE
<222> LOCATION: (101)..(101)
<223> OTHER INFORMATION: X is any amino acid
<220> FEATURE:
<221> NAME/KEY: MISC_FEATURE
<222> LOCATION: (103)..(103)
<223> OTHER INFORMATION: X is any amino acid
<220> FEATURE:
<221> NAME/KEY: MISC_FEATURE
<222> LOCATION: (109)..(109)
<223> OTHER INFORMATION: X is any amino acid
<220> FEATURE:
<221> NAME/KEY: MISC_FEATURE
<222> LOCATION: (113)..(113)
<223> OTHER INFORMATION: X is any amino acid
<220> FEATURE:
<221> NAME/KEY: MISC_FEATURE
<222> LOCATION: (120)..(120)
<223> OTHER INFORMATION: X is any amino acid
<220> FEATURE:
<221> NAME/KEY: MISC_FEATURE
<222> LOCATION: (134)..(135)
<223> OTHER INFORMATION: X is any amino acid
<220> FEATURE:
<221> NAME/KEY: MISC_FEATURE
<222> LOCATION: (137)..(137)
<223> OTHER INFORMATION: X is any amino acid
<220> FEATURE:
<221> NAME/KEY: MISC_FEATURE
<222> LOCATION: (141)..(143)
<223> OTHER INFORMATION: X is any amino acid
<220> FEATURE:
<221> NAME/KEY: MISC_FEATURE
<222> LOCATION: (145)..(145)
<223> OTHER INFORMATION: X is any amino acid
<220> FEATURE:
<221> NAME/KEY: MISC_FEATURE
<222> LOCATION: (148)..(149)
<223> OTHER INFORMATION: X is any amino acid
<220> FEATURE:
<221> NAME/KEY: MISC_FEATURE
<222> LOCATION: (151)..(151)
<223> OTHER INFORMATION: X is any amino acid
<220> FEATURE:
<221> NAME/KEY: MISC_FEATURE
<222> LOCATION: (162)..(164)
<223> OTHER INFORMATION: X is any amino acid
<220> FEATURE:
<221> NAME/KEY: MISC_FEATURE
<222> LOCATION: (166)..(168)
<223> OTHER INFORMATION: X is any amino acid
```

```
<220> FEATURE:
<221> NAME/KEY: MISC_FEATURE
<222> LOCATION: (187)..(187)
<223> OTHER INFORMATION: X is any amino acid
<220> FEATURE:
<221> NAME/KEY: MISC_FEATURE
<222> LOCATION: (197)..(197)
<223> OTHER INFORMATION: X is any amino acid
<220> FEATURE:
<221> NAME/KEY: MISC_FEATURE
<222> LOCATION: (204)..(204)
<223> OTHER INFORMATION: X is any amino acid
<220> FEATURE:
<221> NAME/KEY: MISC_FEATURE
<222> LOCATION: (209)..(209)
<223> OTHER INFORMATION: X is any amino acid
<220> FEATURE:
<221> NAME/KEY: MISC_FEATURE
<222> LOCATION: (214)..(214)
<223> OTHER INFORMATION: X is any amino acid
<220> FEATURE:
<221> NAME/KEY: MISC_FEATURE
<222> LOCATION: (218)..(218)
<223> OTHER INFORMATION: X is any amino acid
<220> FEATURE:
<221> NAME/KEY: MISC_FEATURE
<222> LOCATION: (222)..(222)
<223> OTHER INFORMATION: X is any amino acid
<220> FEATURE:
<221> NAME/KEY: MISC_FEATURE
<222> LOCATION: (240)..(243)
<223> OTHER INFORMATION: X is any amino acid
<220> FEATURE:
<221> NAME/KEY: MISC_FEATURE
<222> LOCATION: (245)..(245)
<223> OTHER INFORMATION: X is any amino acid
<220> FEATURE:
<221> NAME/KEY: MISC_FEATURE
<222> LOCATION: (249)..(249)
<223> OTHER INFORMATION: X is any amino acid
<220> FEATURE:
<221> NAME/KEY: MISC_FEATURE
<222> LOCATION: (251)..(251)
<223> OTHER INFORMATION: X is any amino acid
<220> FEATURE:
<221> NAME/KEY: MISC_FEATURE
<222> LOCATION: (253)..(254)
<223> OTHER INFORMATION: X is any amino acid
<220> FEATURE:
<221> NAME/KEY: MISC_FEATURE
<222> LOCATION: (256)..(257)
<223> OTHER INFORMATION: X is any amino acid
<220> FEATURE:
<221> NAME/KEY: MISC_FEATURE
<222> LOCATION: (260)..(260)
<223> OTHER INFORMATION: X is any amino acid
<220> FEATURE:
<221> NAME/KEY: misc_feature
<222> LOCATION: (261)..(261)
<223> OTHER INFORMATION: Xaa can be any naturally occurring amino acid
<220> FEATURE:
<221> NAME/KEY: MISC_FEATURE
<222> LOCATION: (264)..(264)
<223> OTHER INFORMATION: X is any amino acid
<220> FEATURE:
<221> NAME/KEY: MISC_FEATURE
<222> LOCATION: (266)..(267)
<223> OTHER INFORMATION: X is any amino acid
<220> FEATURE:
<221> NAME/KEY: MISC_FEATURE
<222> LOCATION: (270)..(270)
<223> OTHER INFORMATION: X is any amino acid
<220> FEATURE:
<221> NAME/KEY: MISC_FEATURE
<222> LOCATION: (274)..(277)
<223> OTHER INFORMATION: X is any amino acid
<220> FEATURE:
<221> NAME/KEY: MISC_FEATURE
<222> LOCATION: (279)..(279)
```

<223> OTHER INFORMATION: X is any amino acid
<220> FEATURE:
<221> NAME/KEY: MISC_FEATURE
<222> LOCATION: (281)..(281)
<223> OTHER INFORMATION: X is any amino acid

<400> SEQUENCE: 47

Ala Gln Thr Val Pro Trp Gly Ile Pro Xaa Val Gln Ala Xaa Xaa Ala
1               5                   10                  15

Gln Xaa Xaa Gly Tyr Thr Gly Xaa Gly Val Lys Val Ala Ile Leu Asp
            20                  25                  30

Thr Gly Ile Asp Xaa Ser His Pro Asp Leu Xaa Xaa Xaa Val Xaa Gly
        35                  40                  45

Gly Xaa Ser Val Phe Xaa Asp Xaa Xaa Asn Xaa Xaa Pro Xaa Xaa Asp
    50                  55                  60

Gly Asn Gly His Gly Thr His Val Ala Gly Thr Val Ala Ala Leu Asn
65                  70                  75                  80

Asn Xaa Xaa Gly Val Leu Gly Val Ala Xaa Xaa Ala Xaa Leu Tyr Ala
                85                  90                  95

Val Lys Val Leu Xaa Asn Xaa Gly Ser Gly Ser Tyr Xaa Gly Ile Ala
            100                 105                 110

Xaa Gly Ile Glu Trp Ala Ile Xaa Asn Gly Met Asp Val Ile Asn Met
        115                 120                 125

Ser Leu Gly Gly Ser Xaa Xaa Ser Xaa Ile Leu Lys Xaa Xaa Xaa Asp
130                 135                 140

Xaa Ala Tyr Xaa Xaa Gly Xaa Leu Val Val Ala Ala Ala Gly Asn Ser
145                 150                 155                 160

Gly Xaa Xaa Xaa Gly Xaa Xaa Xaa Thr Val Gly Tyr Pro Ala Lys Tyr
                165                 170                 175

Asp Ser Val Ile Ala Val Gly Ala Val Asp Xaa Asn Asn Asn Arg Ala
            180                 185                 190

Ser Phe Ser Ser Xaa Gly Pro Ala Val Glu Ile Xaa Ala Pro Gly Val
        195                 200                 205

Xaa Ile Leu Ser Thr Xaa Pro Gly Asn Xaa Tyr Ala Ser Xaa Asn Gly
210                 215                 220

Thr Ser Met Ala Ser Pro His Val Ala Gly Val Ala Ala Leu Val Xaa
225                 230                 235                 240

Xaa Xaa Xaa Pro Xaa Leu Ser Asn Xaa Gln Xaa Arg Xaa Xaa Leu Xaa
                245                 250                 255

Xaa Thr Ala Xaa Xaa Leu Gly Xaa Ser Xaa Xaa Tyr Gly Xaa Gly Leu
            260                 265                 270

Val Xaa Xaa Xaa Xaa Ala Xaa Gln Xaa
        275                 280

<210> SEQ ID NO 48
<211> LENGTH: 280
<212> TYPE: PRT
<213> ORGANISM: Bacillus pseudofirmus

<400> SEQUENCE: 48

Gln Asn Val Pro Trp Gly Ile Pro Arg Val Gln Gly Thr Asp Ala Gln
1               5                   10                  15

Asn Ala Gly Tyr Thr Gly Asn Gly Val Lys Val Ala Ile Leu Asp Thr
            20                  25                  30

Gly Ile Asp Arg Ser His Pro Asp Leu Thr Ala Asn Val Gln Gly Gly
        35                  40                  45

His Ser Val Phe Thr Asp Ser Ala Asn Arg Asp Pro Phe Phe Asp Gly
    50                  55                  60

Asp Gly His Gly Thr His Val Ala Gly Thr Val Ala Ala Val Asn Asn
65                  70                  75                  80

Asp Ile Gly Val Val Gly Val Ala Ser Glu Ala Asp Leu Tyr Ala Val
                85                  90                  95

Lys Val Leu Asn Asn Ala Gly Ser Gly Ser Tyr Ala Gly Ile Ala Glu
                100                 105                 110

Gly Ile Glu Trp Ser Ile Asn Asn Gly Met Asp Ile Ile Asn Met Ser
                115                 120                 125

Leu Gly Gly Ser Gln Ser Ser Ala Ile Leu Lys Glu Phe Ser Asp Leu
    130                 135                 140

Ala Tyr Ala Glu Gly Leu Leu Val Val Ala Ala Gly Asn Ser Gly
145                 150                 155                 160

Asn Arg Gly Gly Asn Asn Asp Thr Val Gly Tyr Pro Ala Lys Tyr Glu
                165                 170                 175

Ser Val Ile Ala Val Ala Ala Thr Asp Gln Asn Asn Gln Arg Ala Thr
                180                 185                 190

Phe Ser Ser Thr Gly Pro Ala Val Glu Ile Ser Ala Pro Gly Ala Gly
                195                 200                 205

Ile Leu Ser Thr Thr Pro Asn Asn Asn Tyr Ala Ser Phe Asn Gly Thr
                210                 215                 220

Ser Met Ala Ser Pro His Val Ala Gly Val Ala Ala Gln Val Trp Gln
225                 230                 235                 240

Ala Lys Pro His Leu Ser Asn Val Glu Leu Arg Asn Leu Leu Asn Asp
                245                 250                 255

Thr Ala Leu Pro Leu Gly Gly Ser Asn Gln Phe Gly Asn Gly Leu Val
                260                 265                 270

Gln Ser Met Ala Ala Ile Gln Gln
                275                 280

<210> SEQ ID NO 49
<211> LENGTH: 280
<212> TYPE: PRT
<213> ORGANISM: unknown
<220> FEATURE:
<223> OTHER INFORMATION: Bacillus sp. 18N1

<400> SEQUENCE: 49

Gln Thr Thr Pro Trp Gly Ile Pro Arg Val Gln Gly Thr Ala Ala Gln
1               5                   10                  15

Asn Ala Gly Tyr Thr Gly Asn Gly Val Lys Val Ala Ile Leu Asp Thr
                20                  25                  30

Gly Ile Asp Arg Asn His Pro Asp Leu Ser Ala Asn Val Lys Gly Gly
            35                  40                  45

His Ser Val Phe Thr Asp Ser Ala Asn Ser Asp Pro Phe Phe Asp Gly
    50                  55                  60

Asp Gly His Gly Thr His Val Ala Gly Thr Val Ala Ala Val Asn Asn
65                  70                  75                  80

Asp Ile Gly Val Ile Gly Val Ala Ser Glu Ala Ser Leu Tyr Ala Val
                85                  90                  95

Lys Val Leu Asn Asn Ala Gly Ser Gly Ser Tyr Ala Gly Ile Ala Glu
                100                 105                 110

Gly Ile Glu Trp Ala Ile Asn Asn Asp Ile Asp Ile Ile Asn Met Ser
                115                 120                 125

```
Leu Gly Gly Ser Gln Ser Ser Ala Ile Leu Lys Gln Phe Ser Asp Leu
        130                 135                 140

Ala Tyr Ala Glu Gly Leu Leu Val Val Ala Ala Gly Asn Ser Gly
145                 150                 155                 160

Thr Arg Ser Gly Arg Asn Asp Thr Val Gly Tyr Pro Ala Lys Tyr Asp
                165                 170                 175

Ser Val Ile Ala Val Ala Ala Thr Asp Gln Asn Asn Gln Arg Ala Thr
                180                 185                 190

Phe Ser Ser Thr Gly Pro Ala Val Glu Ile Ser Ala Pro Gly Val Gly
                195                 200                 205

Ile Leu Ser Thr Thr Pro Asn Asn Tyr Val Ser Phe Asn Gly Thr
    210                 215                 220

Ser Met Ala Ser Pro His Val Ala Gly Val Ala Ala Gln Val Trp Gln
225                 230                 235                 240

Ala Lys Pro His Leu Ser Asn Ile Glu Leu Arg Asn Leu Leu Asn Asp
                245                 250                 255

Thr Ala Ile Asp Leu Gly Ser Ser Thr Gln Tyr Gly Asn Gly Leu Val
                260                 265                 270

Gln Ser Leu Glu Ala Ile Gln Gln
            275                 280

<210> SEQ ID NO 50
<211> LENGTH: 280
<212> TYPE: PRT
<213> ORGANISM: unknown
<220> FEATURE:
<223> OTHER INFORMATION: Bacillus sp. WDG291

<400> SEQUENCE: 50

Gln Thr Val Pro Trp Gly Ile Pro His Val Gln Gly Thr Ala Ala Gln
1               5                   10                  15

Asp Ala Gly Tyr Thr Gly Ala Gly Leu Lys Val Ala Ile Leu Asp Thr
                20                  25                  30

Gly Ile Asp Arg Asn His Glu Asp Leu Phe Ala Asn Val Lys Gly Gly
            35                  40                  45

His Ser Val Phe Thr Asp Ser Ala Asn Ser Asp Pro Tyr Asp Ala
    50                  55                  60

Asp Gly His Gly Thr His Val Ala Gly Thr Val Ala Ala Val Asp Asn
65                  70                  75                  80

Asp Leu Gly Val Val Gly Val Ala Ser Gln Ala Glu Leu Tyr Ala Val
                85                  90                  95

Lys Val Leu Asn Asn Ser Gly Ser Gly Ser Tyr Ala Gly Ile Ala Glu
                100                 105                 110

Gly Ile Glu Trp Ser Ile Asn Asn Gly Met Asp Ile Ile Asn Met Ser
            115                 120                 125

Leu Gly Gly Ser Gln Ser Ser Ser Ile Leu Lys Gln Phe Ser Asp Leu
        130                 135                 140

Ala Tyr Glu Glu Gly Leu Leu Val Val Ala Ala Gly Asn Ser Gly
145                 150                 155                 160

Asn Arg Gly Gly Asn Asn Asp Thr Val Gly Tyr Pro Ala Lys Tyr Asp
                165                 170                 175

Ser Val Ile Ala Val Ala Ala Val Asp Gln Asn Asn Asn Arg Ala Thr
                180                 185                 190

Phe Ser Ser Thr Gly Pro Ala Val Glu Ile Ser Ala Pro Gly Val Ser
                195                 200                 205
```

```
Ile Leu Ser Thr Thr Pro Gly Asn Asn Tyr Ala Ala Phe Asn Gly Thr
210                 215                 220

Ser Met Ala Ser Pro His Val Ala Gly Val Ala Ala Gln Val Trp Gln
225                 230                 235                 240

Ala Lys Pro Glu Leu Ser Asn Val Glu Leu Arg Asn Leu Leu Asn Glu
                245                 250                 255

Thr Ala Val Asn Leu Gly Gly Ser Asn Gln Phe Gly His Gly Leu Val
                260                 265                 270

Gln Ser Leu Asp Ala Ile Gln His
                275                 280

<210> SEQ ID NO 51
<211> LENGTH: 280
<212> TYPE: PRT
<213> ORGANISM: unknown
<220> FEATURE:
<223> OTHER INFORMATION: Bacillus sp. WDG290

<400> SEQUENCE: 51

Gln Thr Val Pro Trp Gly Ile Pro His Val Gln Gly Thr Ala Ala Gln
1               5                   10                  15

Asp Ala Gly Phe Thr Gly Ala Gly Leu Lys Val Ala Ile Leu Asp Thr
                20                  25                  30

Gly Ile Glu Ala Ser His Glu Asp Leu Ser Ala Asn Val Lys Gly Gly
            35                  40                  45

His Ser Val Phe Thr Asp Ser Ala Asn Ser Asp Pro Phe Tyr Asp Pro
        50                  55                  60

Asn Gly His Gly Thr His Val Ala Gly Thr Ala Ala Val Asp Asn
65                  70                  75                  80

Asp Leu Gly Val Ile Gly Val Ala Pro Glu Ala Asp Leu Tyr Ala Val
                85                  90                  95

Lys Val Leu Ser Asn Ala Gly Ser Gly Ser Ile Ala Gly Ile Ala Glu
                100                 105                 110

Gly Ile Glu Trp Ser Ile Asp Asn Gly Met Asp Ile Ile Asn Met Ser
            115                 120                 125

Leu Gly Ala Ser Gln Gly Ser Ser Ile Leu Glu Gln Phe Ser Asn Leu
        130                 135                 140

Ala Tyr Asp Glu Gly Leu Leu Val Val Ala Ala Gly Asn Ser Gly
145                 150                 155                 160

Asn Arg Gly Gly Asn Asn Thr Val Gly Tyr Pro Ala Ala Tyr Asp
                165                 170                 175

Ser Val Ile Ala Val Ala Ala Val Asp Gln Asn Asn Arg Ala Thr
                180                 185                 190

Phe Ser Ser Thr Gly Pro Ala Val Glu Ile Ser Ala Pro Gly Val Asn
            195                 200                 205

Val Leu Ser Thr Thr Pro Gly Asn Asn Tyr Ala Ser Tyr Asn Gly Thr
210                 215                 220

Ser Met Ala Ser Pro His Val Ala Gly Val Ala Ala Gln Val Trp Gln
225                 230                 235                 240

Ala Asn Pro Gly Leu Ser Asn Thr Glu Leu Arg Gln Leu Leu Asn Asp
                245                 250                 255

Thr Ala Val Asn Leu Gly Pro Ala His Gln Tyr Gly His Gly Leu Val
                260                 265                 270

Gln Ser Leu Asp Ala Ile Asn Gln
                275                 280
```

<210> SEQ ID NO 52
<211> LENGTH: 274
<212> TYPE: PRT
<213> ORGANISM: Bacillus amyloliquefaciens

<400> SEQUENCE: 52

| Gln | Ser | Val | Pro | Tyr | Gly | Val | Ser | Gln | Ile | Lys | Ala | Pro | Ala | Leu | His |
|---|---|---|---|---|---|---|---|---|---|---|---|---|---|---|---|
| 1 | | | | 5 | | | | | 10 | | | | | 15 | |

| Ser | Gln | Gly | Tyr | Thr | Gly | Ser | Asn | Val | Lys | Val | Ala | Val | Ile | Asp | Ser |
| | | | 20 | | | | | 25 | | | | | 30 | | |

| Gly | Ile | Asp | Ser | Ser | His | Pro | Asp | Leu | Lys | Val | Ala | Gly | Gly | Ala | Ser |
| | | | 35 | | | | 40 | | | | | 45 | | | |

| Met | Val | Pro | Ser | Glu | Thr | Asn | Pro | Phe | Gln | Asp | Asn | Asn | Ser | His | Gly |
| | 50 | | | | | 55 | | | | | 60 | | | | |

| Thr | His | Val | Ala | Gly | Thr | Val | Ala | Ala | Leu | Asn | Asn | Ser | Ile | Gly | Val |
| 65 | | | | | 70 | | | | | 75 | | | | | 80 |

| Leu | Gly | Val | Ala | Pro | Ser | Ala | Ser | Leu | Tyr | Ala | Val | Lys | Val | Leu | Gly |
| | | | | 85 | | | | | 90 | | | | | 95 | |

| Ala | Asp | Gly | Ser | Gly | Gln | Tyr | Ser | Trp | Ile | Ile | Asn | Gly | Ile | Glu | Trp |
| | | | 100 | | | | | 105 | | | | | 110 | | |

| Ala | Ile | Ala | Asn | Asn | Met | Asp | Val | Ile | Asn | Met | Ser | Leu | Gly | Gly | Pro |
| | | | 115 | | | | 120 | | | | | 125 | | | |

| Ser | Gly | Ser | Ala | Ala | Leu | Lys | Ala | Ala | Val | Asp | Lys | Ala | Val | Ala | Ser |
| | 130 | | | | | 135 | | | | | 140 | | | | |

| Gly | Val | Val | Val | Ala | Ala | Ala | Gly | Asn | Glu | Gly | Thr | Ser | Gly | Ser | Ser |
| 145 | | | | | 150 | | | | | 155 | | | | | 160 |

| Ser | Ser | Thr | Val | Gly | Tyr | Pro | Gly | Lys | Tyr | Pro | Ser | Val | Ile | Ala | Val |
| | | | | 165 | | | | | 170 | | | | | 175 | |

| Gly | Ala | Val | Asp | Ser | Ser | Asn | Gln | Arg | Ala | Ser | Phe | Ser | Ser | Val | Gly |
| | | | 180 | | | | | 185 | | | | | 190 | | |

| Pro | Glu | Leu | Asp | Val | Met | Ala | Pro | Gly | Val | Ser | Ile | Gln | Ser | Thr | Leu |
| | | | | 195 | | | | | 200 | | | | | 205 | |

| Pro | Gly | Asn | Lys | Tyr | Gly | Ala | Tyr | Asn | Gly | Thr | Ser | Met | Ala | Ser | Pro |
| | 210 | | | | | 215 | | | | | 220 | | | | |

| His | Val | Ala | Gly | Ala | Ala | Ala | Leu | Ile | Leu | Ser | Lys | His | Pro | Asn | Trp |
| 225 | | | | | 230 | | | | | 235 | | | | | 240 |

| Thr | Asn | Thr | Gln | Val | Arg | Ser | Ser | Leu | Glu | Asn | Thr | Thr | Thr | Lys | Leu |
| | | | | 245 | | | | | 250 | | | | | 255 | |

| Gly | Asp | Ser | Phe | Tyr | Tyr | Gly | Lys | Gly | Leu | Ile | Asn | Val | Gln | Ala | Ala |
| | | | 260 | | | | | 265 | | | | | 270 | | |

| Ala | Gln |
| | |

<210> SEQ ID NO 53
<211> LENGTH: 268
<212> TYPE: PRT
<213> ORGANISM: Bacillus lentus

<400> SEQUENCE: 53

| Gln | Ser | Val | Pro | Trp | Gly | Ile | Ser | Arg | Val | Gln | Ala | Pro | Ala | Ala | His |
|---|---|---|---|---|---|---|---|---|---|---|---|---|---|---|---|
| 1 | | | | 5 | | | | | 10 | | | | | 15 | |

| Asn | Arg | Gly | Leu | Thr | Gly | Ser | Gly | Val | Lys | Val | Ala | Val | Leu | Asp | Thr |
| | | | 20 | | | | | 25 | | | | | 30 | | |

| Gly | Ile | Ser | Thr | His | Pro | Asp | Leu | Asn | Ile | Arg | Gly | Gly | Ala | Ser | Phe |
| | | | 35 | | | | 40 | | | | | 45 | | | |

| Val | Pro | Gly | Glu | Pro | Ser | Thr | Gln | Asp | Gly | Asn | Gly | His | Gly | Thr | His |

```
                50                  55                  60
Val Ala Gly Thr Ile Ala Ala Leu Asn Asn Ser Ile Gly Val Leu Gly
65                  70                  75                  80

Val Ala Pro Ser Ala Glu Leu Tyr Ala Val Lys Val Leu Gly Ala Ser
                    85                  90                  95

Gly Ser Gly Ser Val Ser Ser Ile Ala Gln Gly Leu Glu Trp Ala Gly
                100                 105                 110

Asn Asn Gly Met His Val Ala Asn Leu Ser Leu Gly Ser Pro Ser Pro
            115                 120                 125

Ser Ala Thr Leu Glu Gln Ala Val Asn Ser Ala Thr Ser Arg Gly Val
        130                 135                 140

Leu Val Val Ala Ala Ser Gly Asn Ser Gly Ala Gly Ser Ile Ser Tyr
145                 150                 155                 160

Pro Ala Arg Tyr Ala Asn Ala Met Ala Val Gly Ala Thr Asp Gln Asn
                165                 170                 175

Asn Asn Arg Ala Ser Phe Ser Gln Tyr Gly Ala Gly Leu Asp Ile Val
            180                 185                 190

Ala Pro Gly Val Asn Val Gln Ser Thr Tyr Pro Gly Ser Thr Tyr Ala
        195                 200                 205

Ser Leu Asn Gly Thr Ser Met Ala Thr Pro His Val Ala Gly Ala Ala
        210                 215                 220

Ala Leu Val Lys Gln Lys Asn Pro Ser Trp Ser Asn Val Gln Ile Arg
225                 230                 235                 240

Asn His Leu Lys Asn Thr Ala Thr Ser Leu Gly Ser Thr Asn Leu Tyr
            245                 250                 255

Gly Ser Gly Leu Val Asn Ala Glu Ala Ala Thr Arg
        260                 265
```

We claim:

1. A composition comprising a surfactant and a subtilisin comprising a DTGIXXXHXDLXXXXXGGXSVFXDXXXXXXXXXDXXGH (SEQ ID NO:22) motif, wherein X is any amino acid, and wherein said subtilisin comprises an amino acid sequence having at least 80% amino acid sequence identity to the amino acid sequence of SEQ ID NO: 9, wherein said subtilisin has protease activity in the presence of a surfactant.

2. The composition of claim 1, wherein the surfactant is selected from the group consisting of an anionic surfactant, a cationic surfactant, a zwitterionic surfactant, an ampholytic surfactant, a semi-polar non-ionic surfactant, and a combination thereof.

3. The composition of claim 1, wherein the composition is a detergent composition.

4. The composition of claim 3, wherein the detergent composition is selected from the group consisting of a laundry detergent, a fabric softening detergent, a dishwashing detergent, and a hard-surface cleaning detergent.

5. The composition of claim 1, wherein said composition further comprises at least one calcium ion and/or zinc ion; at least one stabilizer; from about 0.001% to about 1.0 weight % of said subtilisin or recombinant polypeptide; at least one bleaching agent; at least one adjunct ingredient; and/or one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

6. The composition of claim 1, wherein said composition contains phosphate or is phosphate-free and/or contains borate or is borate-free.

7. The composition of claim 1, wherein said composition is a granular, powder, solid, bar, liquid, tablet, gel, paste or unit dose composition.

8. The composition of claim 1, wherein said composition is formulated at a pH of from about 8 to about 12.

* * * * *